(12) United States Patent
Soyao et al.

(10) Patent No.: US 10,791,930 B2
(45) Date of Patent: *Oct. 6, 2020

(54) SYSTEMS, DEVICES, AND METHODS FOR ANALYZING AND ENHANCING PATIENT HEALTH

(71) Applicant: SELF CARE CATALYSTS INC., Toronto (CA)

(72) Inventors: Grace Castillo Soyao, Oakville (CA); Jared Ring Adams, San Francisco, CA (US); Zenon Harley, Waterloo (CA)

(73) Assignee: SELF CARE CATALYSTS INC., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/263,462

(22) Filed: Jan. 31, 2019

(65) Prior Publication Data

US 2019/0159677 A1    May 30, 2019

Related U.S. Application Data

(63) Continuation of application No. 14/614,940, filed on Feb. 5, 2015, now Pat. No. 10,231,622.

(Continued)

(51) Int. Cl.
*H04L 29/08* (2006.01)
*G06F 19/00* (2018.01)
(Continued)

(52) U.S. Cl.
CPC ............ *A61B 5/0022* (2013.01); *G06F 19/34* (2013.01); *G06F 19/3418* (2013.01);
(Continued)

(58) Field of Classification Search
CPC . H04L 67/02; H04L 67/1002; H04L 67/1008; G06Q 20/20; G06Q 50/22;
(Continued)

(56) References Cited

U.S. PATENT DOCUMENTS 8,447,285 B1 * 5/2013 Bladon .................. H04L 51/32
455/414.4
8,818,903 B2 * 8/2014 Dulin ...................... G06F 21/33
705/64

(Continued)

OTHER PUBLICATIONS

USPTO, Office Action for U.S. Appl. No. 14/614,940, dated Feb. 27, 2018.

(Continued)

*Primary Examiner* — Ninos Donabed
(74) *Attorney, Agent, or Firm* — Norton Rose Fulbright Canada LLP

(57) ABSTRACT

There are disclosed systems, devices, and methods for generating insights relating to patient health using a social networking platform interconnecting a patient with a plurality of care givers. The patient is provided access to a computer application configured to solicit and collect patient data from the patient, the computer application selected based on at least one characteristic of the patient. First patient data reflective of the health condition of the patient, as collected by the computer application, are received through the social networking platform. A communication from a care giver is transmitted to the patient through the social networking platform. Second patient data reflective of the health condition responsive to the transmitted communication are received through the social networking platform. The first and second patient data are analyzed to determine at least one insight relating to health of the patient; and a report is generated to present the insight.

21 Claims, 51 Drawing Sheets

Related U.S. Application Data

(60) Provisional application No. 61/936,283, filed on Feb. 5, 2014.

(51) Int. Cl.

| | | |
|---|---|---|
| *A61B 5/00* | (2006.01) | |
| *G16H 15/00* | (2018.01) | |
| *G16H 10/60* | (2018.01) | |
| *G16H 40/67* | (2018.01) | |
| *G16H 50/20* | (2018.01) | |
| *G16H 20/10* | (2018.01) | |
| *G16H 20/60* | (2018.01) | |
| *A61B 5/021* | (2006.01) | |
| *G01G 19/44* | (2006.01) | |
| *G16H 20/30* | (2018.01) | |

(52) U.S. Cl.
CPC ...... *G06F 19/3456* (2013.01); *G06F 19/3475* (2013.01); *G16H 10/60* (2018.01); *G16H 15/00* (2018.01); *G16H 20/10* (2018.01); *G16H 20/60* (2018.01); *G16H 40/67* (2018.01); *G16H 50/20* (2018.01); *H04L 67/12* (2013.01); *A61B 5/021* (2013.01); *A61B 5/4833* (2013.01); *A61B 5/4848* (2013.01); *G01G 19/44* (2013.01); *G06F 19/3481* (2013.01); *G16H 20/30* (2018.01)

(58) Field of Classification Search
CPC ........ G06Q 10/10; G06Q 20/40; G06Q 30/02; G06Q 20/401; G06Q 2220/00; G06F 17/30752; G06F 17/30772; G06F 17/30566; G06F 9/54
See application file for complete search history.

(56) References Cited

U.S. PATENT DOCUMENTS

| | | | | |
|---|---|---|---|---|
| 9,262,612 | B2* | 2/2016 | Cheyer | G06F 21/32 |
| 9,538,962 | B1* | 1/2017 | Hannaford | G16H 20/40 |
| 2002/0015480 | A1* | 2/2002 | Daswani | G06F 17/30867 |
| | | | | 379/88.17 |
| 2002/0059425 | A1* | 5/2002 | Belfiore | G06F 9/54 |
| | | | | 709/226 |
| 2003/0216919 | A1* | 11/2003 | Roushar | G06F 17/277 |
| | | | | 704/260 |
| 2005/0043940 | A1* | 2/2005 | Elder | G06F 17/3043 |
| | | | | 704/9 |
| 2006/0095331 | A1* | 5/2006 | O'Malley | G06F 17/30902 |
| | | | | 705/22 |
| 2006/0149558 | A1* | 7/2006 | Kahn | G10L 15/063 |
| | | | | 704/278 |
| 2006/0161457 | A1* | 7/2006 | Rapaport | G06Q 10/10 |
| | | | | 705/2 |
| 2006/0168259 | A1* | 7/2006 | Spilotro | H04L 63/102 |
| | | | | 709/229 |
| 2008/0021731 | A1 | 1/2008 | Rogers et al. | |
| 2010/0030578 | A1* | 2/2010 | Siddique | G06Q 10/0637 |
| | | | | 705/3 |
| 2011/0125044 | A1* | 5/2011 | Rhee | A61B 5/113 |
| | | | | 600/534 |
| 2011/0286584 | A1* | 11/2011 | Angel | G10L 15/26 |
| | | | | 379/88.02 |
| 2011/0287748 | A1* | 11/2011 | Angel | H04M 7/0054 |
| | | | | 455/414.1 |
| 2011/0288380 | A1* | 11/2011 | Inciardi | G01M 3/165 |
| | | | | 600/301 |
| 2012/0323574 | A1* | 12/2012 | Wang | G10L 15/22 |
| | | | | 704/246 |
| 2012/0323576 | A1* | 12/2012 | Wang | G10L 15/26 |
| | | | | 704/251 |
| 2012/0323597 | A1* | 12/2012 | Woolford | G06Q 50/22 |
| | | | | 705/2 |
| 2012/0323938 | A1* | 12/2012 | Skeen | G06F 17/30752 |
| | | | | 707/754 |
| 2013/0035946 | A1 | 2/2013 | Ratan et al. | |
| 2013/0073306 | A1 | 3/2013 | Shlain et al. | |
| 2013/0080184 | A1* | 3/2013 | Streat | G06Q 50/24 |
| | | | | 705/2 |
| 2013/0090749 | A1 | 4/2013 | Oswald et al. | |
| 2013/0124218 | A1 | 5/2013 | Masloski et al. | |
| 2013/0124523 | A1 | 5/2013 | Rogers et al. | |
| 2013/0215116 | A1* | 8/2013 | Siddique | G06Q 30/0643 |
| | | | | 345/420 |
| 2013/0226608 | A1* | 8/2013 | Di Lascia | G06F 19/3431 |
| | | | | 705/2 |
| 2013/0339877 | A1* | 12/2013 | Skeen | G06F 3/0484 |
| | | | | 715/753 |
| 2014/0032234 | A1 | 1/2014 | Anderson | |
| 2014/0149599 | A1* | 5/2014 | Krishna | H04L 69/08 |
| | | | | 709/232 |

OTHER PUBLICATIONS

USPTO, Office Action for U.S. Appl. No. 14/614,940, dated Sep. 21, 2017.
USPTO, Office Action for U.S. Appl. No. 14/614,940, dated Mar. 3, 2017.
USPTO, Office Action for U.S. Appl. No. 14/614,940, dated Aug. 11, 2016.
International Searching Authority, International Search Report dated May 11, 2015, issued in International Application No. PCT/CA2015/000064.
International Searching Authority, Written Opinion dated May 7, 2015, issued in International Application No. PCT/CA2015/000064.

* cited by examiner

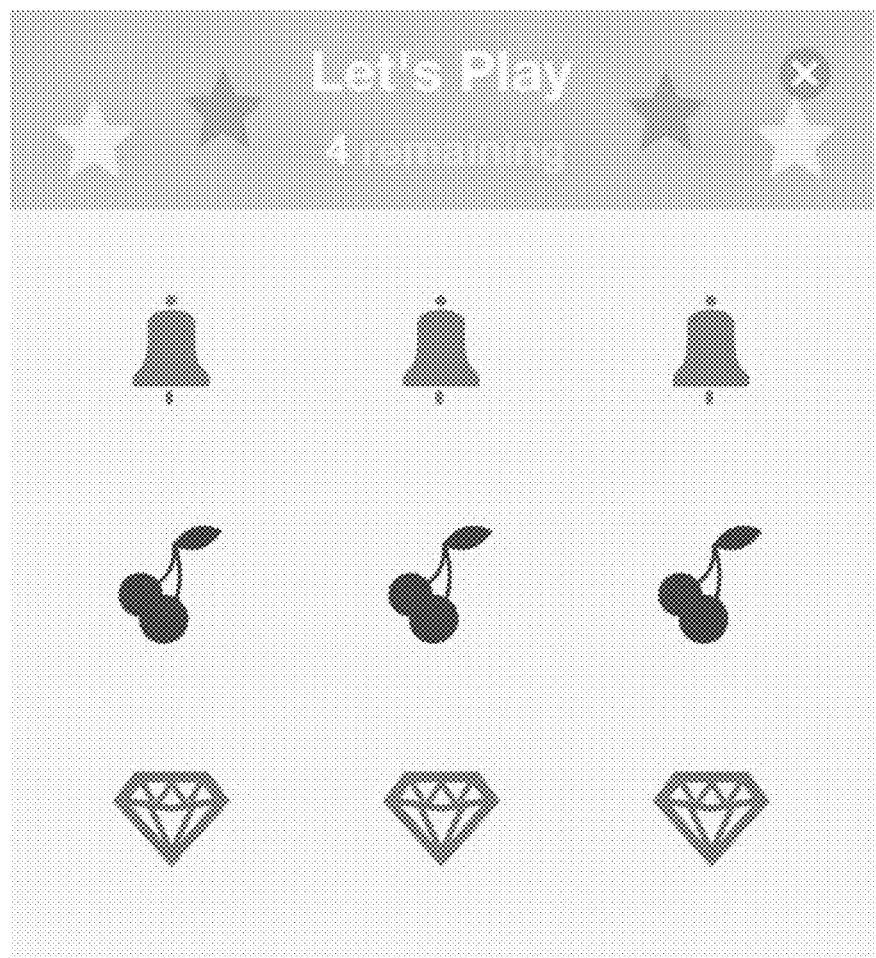
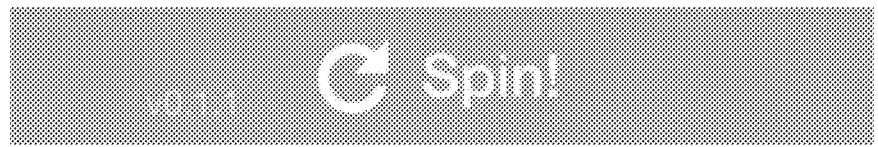
FIG. 9b

| Socio-economic | Intrapersonal Factors | Interpersonal Factors | Environment |
|---|---|---|---|
| • Cost of care<br>• Employment<br>• Economic status<br>• Religion: S, EMR<br>• Ethnicity: S, EMR<br>• Education: S, EMR<br>• Locality: S, EMR | • Age: S, EMR<br>• Gender: S<br>• Self-esteem: S<br>• Self-efficacy: S<br>• Attitudes: S<br>• Perceived social norms: S<br>• Beliefs: S<br>• Stress: S<br>• Depression: S, EMR<br>• Alcohol abuse: S | • Relationship with provider: CC, S<br>• Social Support: CC, S | • High Risk Situations: GPS<br>• Availability of fast food: GPS<br>• Unstable work/life environment: S |

| Treatment Characteristics | Disease Characteristics | Healthcare System | Behavioral Patterns |
|---|---|---|---|
| • Complexity: EMR, S | • Duration: EMR, S | • PCP vs. specialists: EMR<br>• Involvement of nurse, caregiver: CC<br>• Intensity of education: EMR | • Past adherence, Q<br>• Activity level, M7<br>• Quest completion, Q<br>• Goal setting, Q<br>• Goals met, Q<br>• Emotions, Q |

LEGEND: S: Survey | EMR: Blue Button EMR pull | CC: Patient entered circle of care | Q: Quests | M7: iPhone activity sensor | GPS: GPS data

SYSTEMS, DEVICES, AND METHODS FOR ANALYZING AND ENHANCING PATIENT HEALTH

CROSS-REFERENCE TO RELATED APPLICATION

This is a continuation stemming from U.S. patent application Ser. No. 14/614,940, filed Feb. 5, 2015, which claims the benefit of U.S. Provisional Application No. 61/936,283, filed Feb. 5, 2014, all of which are incorporated by reference in their entirety.

FIELD

The present disclosure relates generally to patient health care, and more particularly to systems, devices, and methods for analyzing and enhancing patient health using a social networking platform interconnecting patients with care givers.

BACKGROUND

Patients often feel alone and isolated as they try to manage their health condition, especially once they leave the care of their physician or health care professional (HCP). Saddled with a long list of things to do (e.g. interventions, medications, health monitoring, lifestyle changes, diet modifications, symptom tracking, and so on), patients are often overwhelmed and ill-equipped to perform self-care upon discharge from a hospital or leaving the physician's office.

Once a patient has come home, the at-home environment is completely different from the hospital environment and lacks the critical care tools and most importantly the HCP who could monitor them on a regular basis.

Access to integrated, direct and reliable communication between patients and their support network (e.g. physicians, nurses, social workers, family members, psychologists, etc.) is no longer present once patients leave hospitals.

In addition, the patient's illness itself, interventions required, expectations to complete activities they were never trained for and lack of immediate support are often the barriers to good health outcomes.

Further, patients are increasingly not given ample time by physicians to articulate their day to day health issues. For example, average consult time with physicians is 10 minutes which prevents patients from disclosing an extensive review or update about their state of health. This situation pushed the traditional view and practice that patients are essentially recipients of health care and advice. In reality, patients can be an enormous source of health information from recording their day to day activities in real world, real time which capture broader and deeper health information beyond what clinicians capture inside the clinical, hospital or laboratory settings. Patient-driven data can provide enormous supplementary knowledge and insights that could influence the course and timing of patient care.

Studies reveal that storytelling or the ability of patients to share their health experiences to others is comforting and healing. Traditionally, patients use paper and pencil to record important information or track certain health metrics that only patients know because they experience it daily, beyond the usual bioinformatics that are tracked by healthcare professionals. Some patients find it helpful to monitor their mood, their diet, exercise or other activities relevant to their specific conditions but current modalities are either still dependent on paper or are not integrated, making it a challenge for patients or even their care providers to get a holistic picture of the patient experience outside the clinical setting. A more holistic understanding of the full, real world, real time patient journey and experiences could potentially improve the course and timing of patient care. Furthermore, today's pharmaceutical marketers are faced with a new competitive landscape characterized by an increasing shift of decision-making power on brand choice from the traditional promotional targets (the physicians and pharmacists) to the actual consumers—the empowered patients.

Patients' knowledge, experiences, psychosocial dispositions and self-care cultures have been progressively brought into their conversations with physicians and have had the power to reaffirm, revise, or completely alter the physicians' brand choices.

Marketing efforts designed around influencing physician behaviors have given diminishing returns in recent years, as differentiated campaigns have been harder to mount, and physician choices have encountered increasing pressure from both payors and patients.

Understanding the mindsets, behaviors and decision-making framework of patients is becoming indispensable for marketers to determine the critical factors influencing patient's opinions that they bring into conversations with their physicians and pharmacists. As patients become more medically-informed and assertive about their care, patient insights and sentiments increasingly shape the final prescription and thereafter the final brand choice at point of purchase.

Traditional data available to marketers focuses on actual and projected point-of-prescription and point-of-sale metrics such as physician prescription habits and pharmacy dispensing data. Commercial leaders have for years relied mostly on permutations of these audits to track marketing and sales effectiveness, making do with the limited parameters and supplementing understanding with more in-depth primary research among doctors and pharmacists.

In between doctors' prescription and purchases at the pharmacies, however, is the critical area of patient decision-making, which can explain gaps in prescription fulfillment as well as motivations to stop, continue, or modify adherence to the prescribed drug regimen.

For pharmaceutical marketers, it is of significant value to measure the levers that influence patient behavior towards treatment adoption, adherence and advocacy. Programs targeting patient-centric metrics may help with driving brand recognition, acceptance and loyalty, which is now only marginally increased with physician-centered campaigns.

Therefore, improved solutions are desired to address one or more of the above-mentioned problems.

SUMMARY

In accordance with an aspect, there is provided a computer-implemented method for generating insights relating to patient health using a social networking platform interconnecting a patient with a plurality of care givers. The method includes: receiving at least one characteristic of the patient, the at least one characteristic comprising a health condition of the patient; providing at least one computer application for access by the patient by way of the social networking platform, the at least one computer application configured to solicit and collect patient data from the patient, the at least one computer application selected from amongst a library of computer applications based on the at least one characteristic of the patient; receiving, by way of at the social networking platform, first patient data reflective of the health condition of the patient, as collected by the at least one computer application; transmitting, by way of at the social networking platform, a communication from at least one of the care givers to the patient; receiving, by way of the social networking platform, second patient data reflective of the health condition of the patient, the second patient data responsive to the transmitted communication; analyzing, using at least one processor, the first and second patient data to determine at least one insight relating to health of the patient; and generating, using the at least one processor, a report for presenting the at least one insight.

In accordance with another aspect, there is provided a system for generating insights relating to patient health. The system includes a social networking platform interconnecting a patient with a plurality of care givers; a library of computer applications, each configured to solicit and collect patient data from the patient; and at least one processor configured: receive at least one characteristic of the patient, the at least one characteristic comprising a health condition of the patient; providing at least one computer application for access by the patient by way of the social networking platform, the at least one computer application selected from the library of computer applications based on the at least one characteristic of the patient; receive, by way of at the social networking platform, first patient data reflective of the health condition of the patient, as collected by the at least one computer application; transmit, by way of at the social networking platform, a communication from at least one of the care givers to the patient; receive, by way of the social networking platform, second patient data reflective of the health condition of the patient, the second patient data responsive to the transmitted communication; analyze the first and second patient data to determine at least one insight relating to health of the patient; and generate a report for presenting the at least one insight.

In this respect, before explaining at least one embodiment of the invention in detail, it is to be understood that the invention is not limited in its application to the details of construction and to the arrangements of the components set forth in the following description or the examples provided therein, or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

In the drawings, embodiments of the invention are illustrated by way of example. It is to be expressly understood that the description and drawings are only for the purpose of illustration and as an aid to understanding, and are not intended as a definition of the limits of the invention.

FIGS. 9a-9c, 10-18, 19a, 19b, 20a and 20b illustrate example user interfaces of a system for analyzing and enhancing patient health, in accordance with an embodiment.

FIGS. 23a-23f illustrate sample patient reports generated by the system of FIG. 3, in accordance with an embodiment.

FIGS. 24a-24d illustrate sample aggregated reports by the system of FIG. 3, in accordance with an embodiment.

FIG. 25 illustrates channels for collecting patient data, in accordance with an embodiment.

FIGS. 35 and 36 illustrate example user interfaces for presenting patient data to a case manager, in accordance with an embodiment.

DETAILED DESCRIPTION

Figure 1:
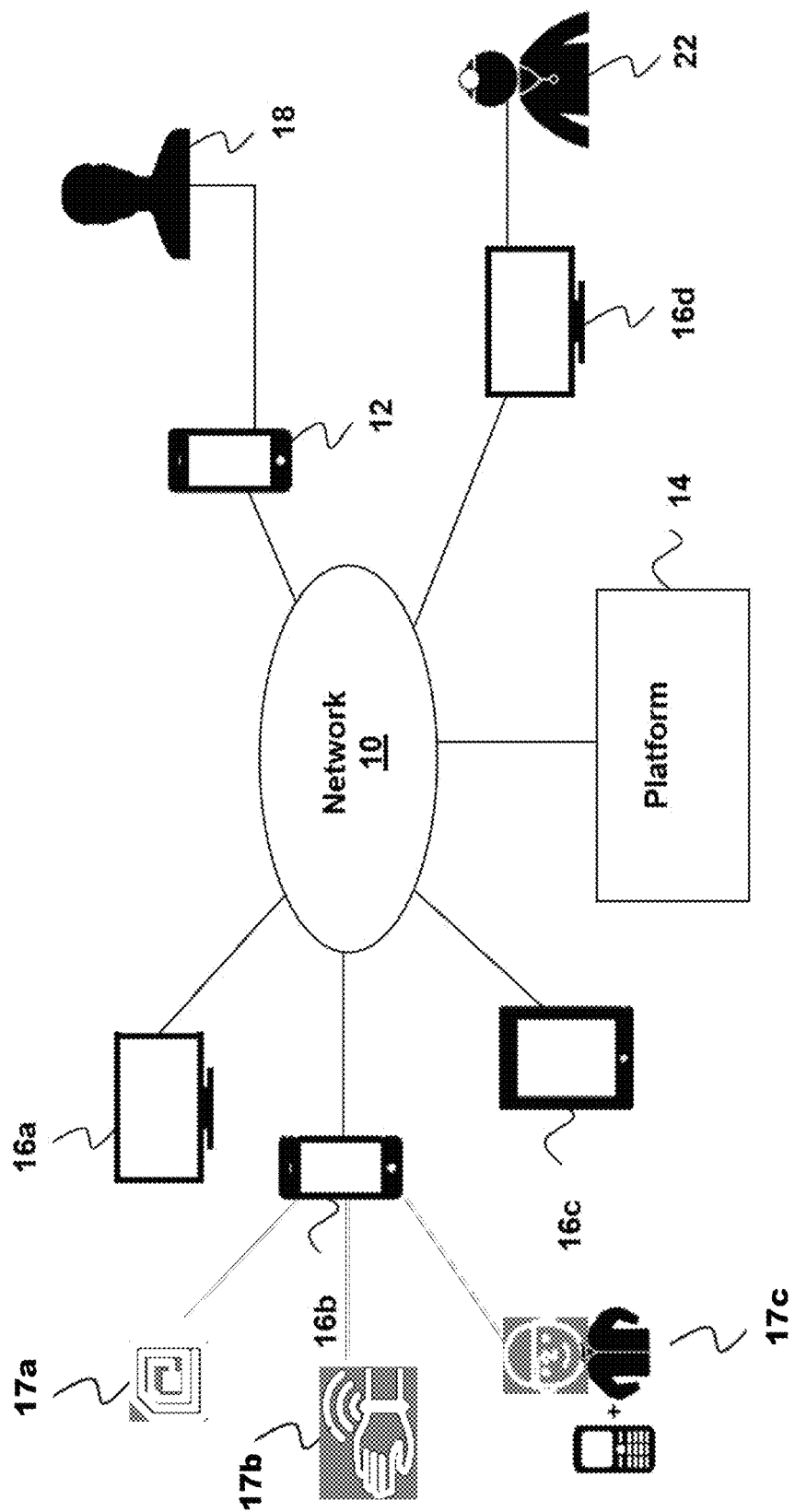
FIG. 1 illustrates a system for analyzing and enhancing patient health, in accordance with an embodiment.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example, and without limitation, the various programmable computers may be a server, network appliance, set-top box, embedded device, computer expansion module, personal computer, laptop, personal data assistant, cellular telephone, smartphone device, UMPC tablets and wireless hypermedia device or any other computing device capable of being configured to carry out the methods described herein.

Program code is applied to input data to perform the functions described herein and to generate output information. The output information is applied to one or more output devices, in known fashion. In some embodiments, the communication interface may be a network communication interface. In embodiments in which elements of the invention are combined, the communication interface may be a software communication interface, such as those for interprocess communication. In still other embodiments, there may be a combination of communication interfaces implemented as hardware, software, and combination thereof.

Each program may be implemented in a high level procedural or object oriented programming or scripting language, or a combination thereof, to communicate with a computer system. However, alternatively the programs may be implemented in assembly or machine language, if desired. The language may be a compiled or interpreted language. Each such computer program may be stored on a storage media or a device (e.g., ROM, magnetic disk, optical disc), readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the systems and methods of the described embodiments are capable of being distributed in a computer program product including a physical, non-tranisitory computer readable medium that bears computer usable instructions for one or more processors. The medium may be provided in various forms, including one or more diskettes, compact disks, tapes, chips, magnetic and electronic storage media, volatile memory, non-volatile memory and the like. Non-transitory computer-readable media may include all computer-readable media, with the exception being a transitory, propagating signal. The term non-transitory is not intended to exclude computer readable media such as primary memory, volatile memory, RAM and so on, where the data stored thereon may only be temporarily stored. The computer useable instructions may also be in various forms, including compiled and non-compiled code.

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable media storing the instructions that cause a processor to execute the disclosed steps. One should appreciate that the systems and methods described herein may transform electronic signals of various data objects into three dimensional representations for display on a tangible screen configured for three dimensional displays. One should appreciate that the systems and methods described herein involve interconnected networks of hardware devices configured to receive data using receivers, transmit data using transmitters, and transform electronic data signals for various three dimensional enhancements using particularly configured processors, where the three dimensional enhancements are for subsequent display on three dimensional adapted display screens.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used herein, a patient may be any person having at least one health condition. For example, a patient may be an individual in need of recovering from an illness or a medical procedure. The condition may be an acute or short-term condition. The condition may also be a chronic or long-term condition. For example, a patient may be an individual who has been diagnosed with Type II diabetes and discharged from a hospital. Such an individual often needs to rely on community nurses, social workers or family members to continue meeting the demands of post-consult and post-hospitalization care requirements.

Once discharged from a hospital or from a physician's office, patients often rely on community nurses, social workers or family members to meet post-consult and post-hospitalization care requirements. However, access to integrated, direct, and reliable communication between patients and a network of supporters and health care professionals (e.g. physicians, nurses, social workers, family members, psychologists, etc.) is no longer present once patients leave hospitals. In the present disclosure, such supporters and healthcare professionals may collectively be referred to as care givers.

Figure 4:
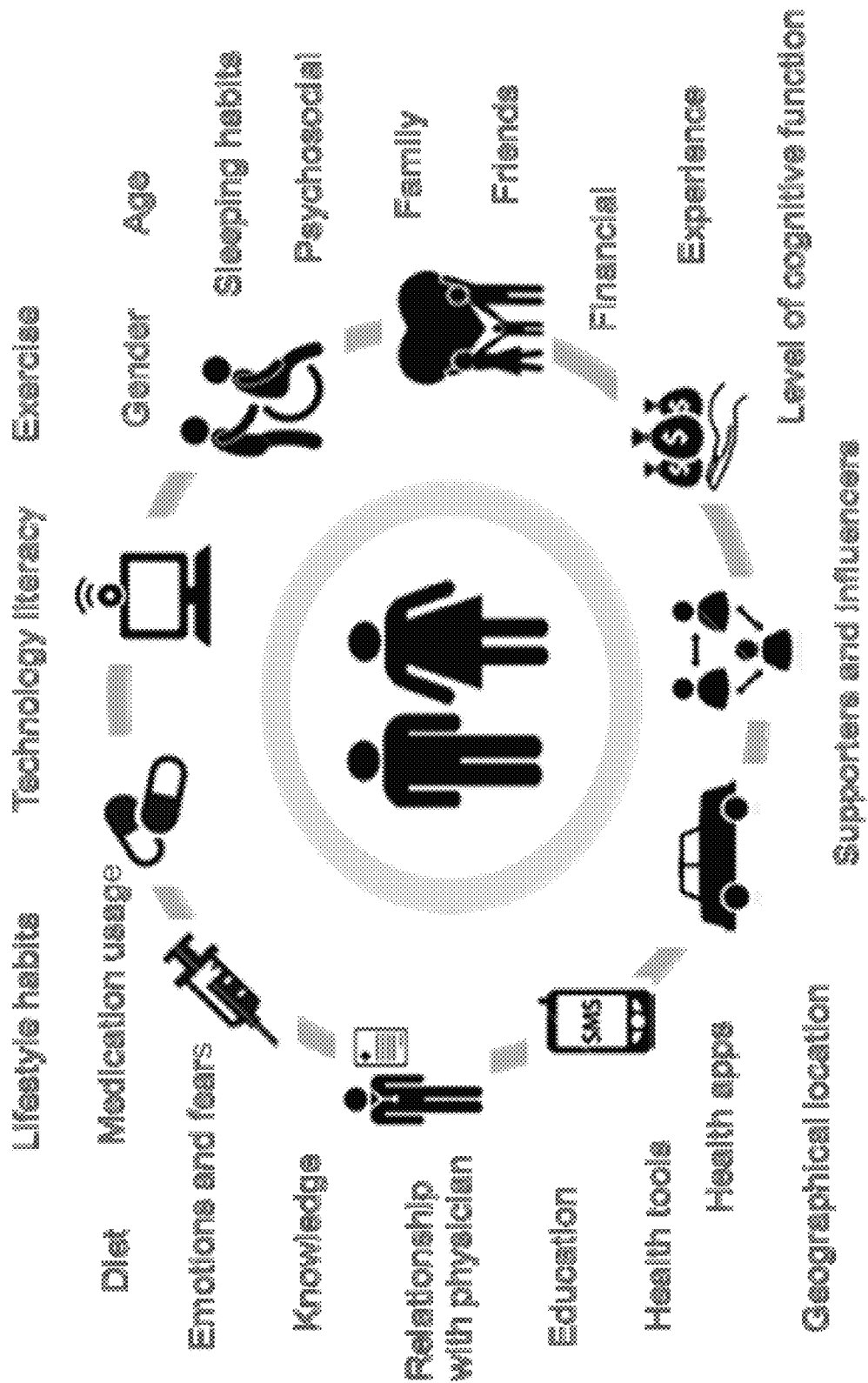
FIG. 4 illustrates a plurality of factors relevant in patient self-care, in accordance with an embodiment.

Self-care management is often multi-dimensional. It can require information, knowledge, planning, organization, prioritization, execution of interventions and activities that patients are never trained to do and often compete with patient's psychosocial and emotional interests. A variety of factors may prevent a patient from properly managing his or her self-care, such as lifestyle habits, financial state, education, geographical location, sleeping habits, gender, age, sleeping habits, family and friends, level of cognitive functions, technology literacy, medication use, diet, emotions and fears, knowledge, and so on (e.g. as shown in FIG. 4).

Specifically, patients often struggle in the following aspects of disease management:

Medication adherence (compliance) and reconciliation—patients may not take medications as directed, in terms of timing of administration, dosage, frequency, wrong drug combination and medication errors.

Medication persistence—patients may not take drugs for the prescribed duration (e.g. 5 days instead of 1 full week, 3 months instead of 6 months, etc.), often leading to discontinuation of medication before the end of the prescribed period.

Diet and nutrition interventions—changing patient's diet is often difficult because it involves breaking long-term habits, including planning, purchasing, preparing, cooking and eating. Doing these activities is a challenge especially when there is no support system at home.

Monitoring—health monitoring requires full awareness of symptoms to watch out for and to record or document changes. Traditionally, patients recognize symptoms when they are out of the norm or when they are impacting patient's daily lives. Upon hospital discharge, patients are expected to monitor symptoms and report those that may indicate risks or danger.

Psychosocial/emotional—patients undergo several levels of emotions during their journey, from diagnosis, to treatment management and all the way to post treatment. Patients experience a wide range of emotional and psychosocial challenges (e.g. denial, depression, anxiety, feelings of isolation, frustration, disappointment, regret, fear, loss of self-esteem, etc.). Patients may need a platform to journal, share and seek help during such difficult periods.

Support—research also reveals that patients who know that they are being followed and monitored perform well in self-care management, specifically in documenting symptoms, sharing their feelings and emotions and executing certain tasks against health goals that were pre-established for them.

Complexity—relief from the complexity of illness management often requires an environment that will enable patients to ask questions, share information, record feelings, seek help and support from a wide range of people, even geographically distant ones.

Patient engagement and ability to sustain disease interventions—it is not easy to sustain all activities expected from patients on a daily or regular basis. Along the way, they experience fatigue, lack of interest, feeling that they no longer need medication because they feel better, face competition with their other life priorities which some deem as far more important and urgent. A platform or means to ignite interest, excitement, motivation to sustain self-care and disease management is crucial to achieving better health outcomes.

Conflict—Patients experience decision conflicts because choosing and prioritizing health interventions (e.g. taking medication, amidst their other life activities). Maintaining existing professional and social connections requires high-level decision making.

In an aspect, there is provided a system configured to collect and analyze patient data, e.g., reflective of a patient's health condition. As will be detailed herein, the system may use a variety of channels and mechanisms to solicit and collect patient data. For example, the system may include a social networking platform configured to connect patients with a network of supporters and care givers. The system may utilize this social networking platform to establish a variety of channels and mechanisms to solicit and collect patient data. The system may analyze the collected data to generate insights relating to patient health. Such insights may include, for example, insights regarding patient behaviour (e.g., adherence to drug regimens, moods, selection of particular brands of pharmaceuticals, etc.). The insights may be used to influence a patient's behaviour (e.g., to promote adherence to a drug regime, to lift mood, etc.), which may in turn promote self-care. The insights may be provided to third-parties for use, e.g., in association with market research or clinical research.

The system may utilize the social networking platform to engage the patient's network of supporters and care givers (e.g. physicians, nurses, social workers, family members, psychologists, etc.), hereinafter referred to as a "Circle of Support" or a "Circle of Care", and facilitate and encourage the involvement of the Circle of Support in the patient's self-care through activities, interventions, and interactions.

A patient's Circle of Support may include a close, trusted group of people that communicate with and support the patient, e.g., during a recovery process. The Circle of Support may consist of a patient's closest supporters and allies. Members of Circle of Support may also be referred to as Health Allies.

Figure 5:
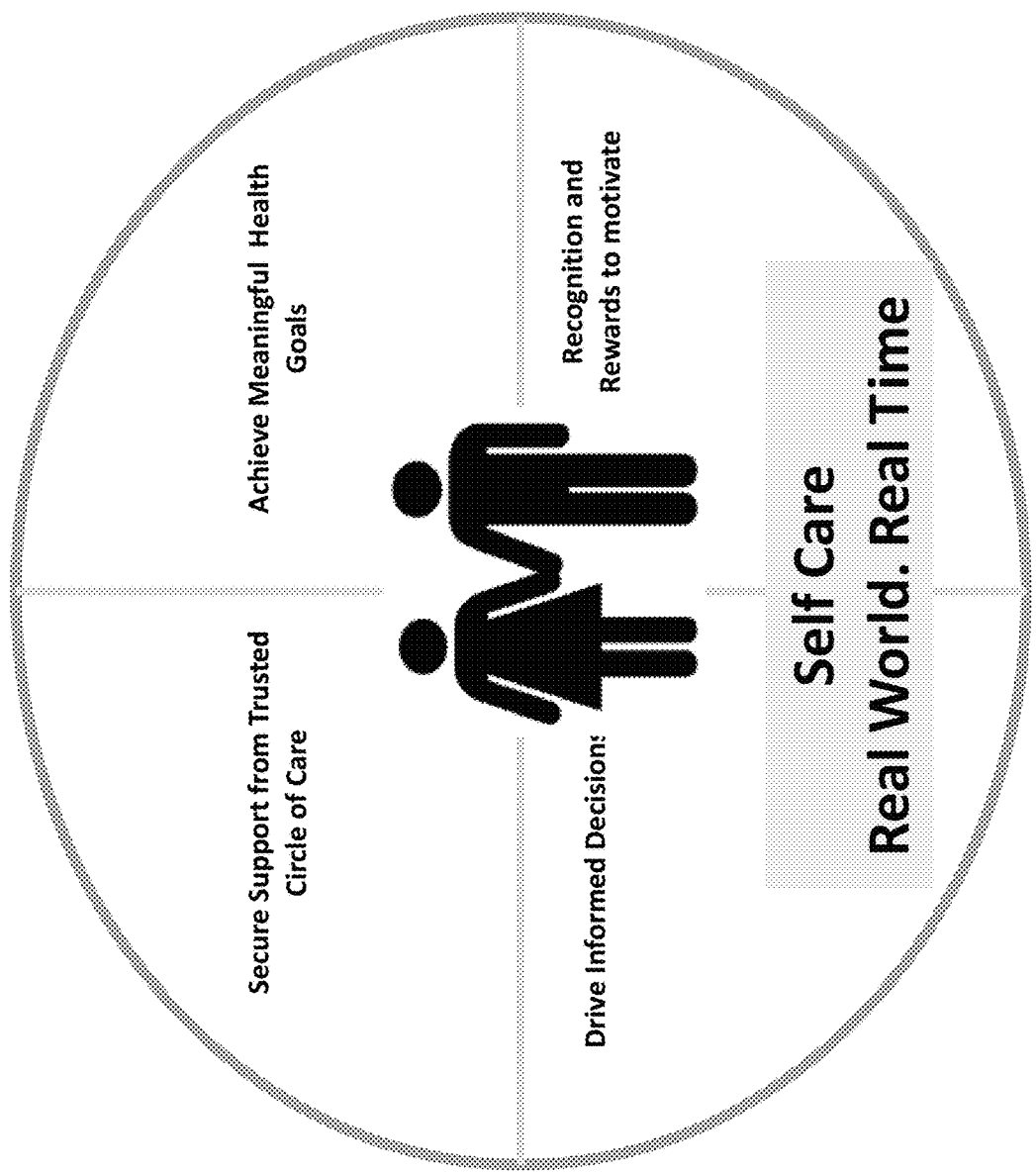
FIG. 5 shows exemplary features of system for analyzing and enhancing patient health, in accordance with an embodiment.

In other aspects, there are disclosed systems, devices, and methods that provide a self-care and journaling solution and platform that may inform, comfort, and support a patient who is recovering from an illness or chronic condition, and may be suffering, isolated, or anxious, etc. Such a solution and platform may help the patient perform self-care (e.g., during a recovery process) in various manners. For example, help may be automatically provided by the solution and platform by obtaining support from members of a patient's Circle of Support, helping patients to achieve health goals, driving informed decision-making, giving recognition and rewards to motivate the patient, and so on, as depicted for example in FIG. 5.

As will be described below, the system includes a special purpose social network configured to enable communication between patients and selected individuals who are likely to be able to help those patients meet health objectives, e.g., their Circle of Support. The health objectives may relate to rehabilitation, disease management, disease prevention, and so on. An application and a platform are provided to implement and configure such social networks, and to facilitate communications amongst patients and Circle of Support members around health objectives, in a way that produces results relative to the health objectives.

Referring now to FIG. 1, an example system in accordance with an embodiment is shown. Network 10 may be one or more networks in any suitable form, including as a local area network or a wide area network, such as an enterprise network or the Internet. Such networks may be based on any suitable technology and may operate according to any suitable protocol and may include wireless networks, wired networks or fiber optic networks. For example, network 10 may be any network capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

Computing device 12 provides one or more patients 18 with access to a patient self-care solution application 100 executing at device 12, and a platform 14 by way of network 10. In an embodiment, computing device 12 may be a mobile device (e.g. an iPhone™ or Android™ device). In an embodiment, computing device 12 may be another type of networked computing device, such as a personal computer, workstation, server, portable computer, mobile device, personal digital assistant, laptop, tablet, WAP phone, an interactive television, video display terminals, gaming consoles, electronic reading device, and portable electronic devices or a combination of these.

For simplicity only one device 12 is shown, but the system may include one or more devices 12 operable by patients 18 or other uses to access remote network resources (e.g., at platform 14).

It is to be appreciated that even though mobile devices such as a phone or a tablet may be illustrated in the drawings and referred to in the description, they may also be substituted with any type of computing device capable of providing the functionalities described herein. For example, a mobile phone may also be a tablet device or a desktop device, and vice versa.

Application 100 may be particularly configured with hardware and software to interact with platform 14 via network 10 to implement the functionalities described herein. Application 100 may be implemented using one or more processors and one or more data storage devices configured with database(s) or file system(s), or using multiple devices or groups of storage devices distributed over a wide geographic area and connected via a network (which may be referred to as "cloud services").

As will be described below, application 100 is configured to interoperate with platform 14 to motivate patients 18 to engage in self-care through connections with members of their Circle of Support and/or other patients 18. For example, application 100 and platform 14 may be configured to allow Circle of Support members to assign and motivate patients 18 to complete customized and interactive Health Quests 26 (customized health-related tasks, as described below). Application 100 and platform 14 may be configured to allow communication amongst patients 18 and members of their Circle of Support, which may be automatically directed to focus on health-related topics or issues. Such issues may be automatically selected based on insights generated for a particular patient 18. Recognition, games, and rewards may also be provided in order to encourage the patients 18 to complete Health Quests 26.

Each of devices 12 and platform 14 may include any type of processor, such as, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof. Platform 14 may include any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each of platform 14 and application 100 may include one or more input devices, such as a keyboard, mouse, camera, touch screen, sensors, and a microphone, and may also include one or more output devices such as a display screen (with three dimensional capabilities) and a speaker. Platform 14 has a network interface in order to communicate with other components, to access and connect to network resources, to serve an application and other applications, and perform other computing applications by connecting to a network (e.g., network 10 or multiple networks).

Each of devices 16a, 16b, 16c, and 16d (which may be referred to individually as a device 16 or collectively as devices 16) provides one or more members of a patient's Circle of Support (e.g., a physician 22) with access to application 100 (executing at a device 16), and platform 14 by way of network 10. Each device 16 may be substantially similar to device 12.

Each device 16 may optionally communicate with one or more external devices 17a, 17b, and 17c (which may be referred to individually as an external device 17 or collectively as external devices 17). External devices 17 may include, for example, various devices having sensors for detecting patient data, such as smart watches, sleep and fitness trackers, weight scales, blood pressure cuffs, pulse oximeters, etc. Such devices may be worn, carried, or used by the patient 18. Such devices may be used in patients' homes. External devices 17 may also include, for example, various medical devices or instrumentation used by healthcare professionals, e.g., in a medical setting such as a hospital or other care facility. External devices 17 may also include data entry devices (e.g., computers, smart phones, tablets, etc.) used by healthcare professionals for entering patient data, e.g., for logging data collected in a checkup. External devices 17 may also include, for example, radio-frequency identification (RFID) tags attached to objects with which a patient may interact (e.g., pill bottles, fitness equipment, etc.). Patient interactions with such objects may be detected by way of such tags, and these interactions may be received and recorded as patient data, as detailed below.

Each device 16 may receive patient data from one or more external devices 17. Patient data may be received by way of various communication interfaces such as WFi, Bluetooth, infra-red, Near-field communication (NFC), or the like. Such patient data may be provided to application 100, and may be relayed to platform 14.

One or both of application 100 and platform 14 may be configured to register and authenticate users (using a login, unique identifier, and password for example) prior to providing access to applications, a local network, network resources, other networks and network security devices. Platform 14 may concurrently serve multiple users.

As detailed below, platform 14 includes an analytics utility configured to analyze patient data (e.g. data collected through application 100) to generate insights. Such insights may be generated using health behavior-driven analytics. Such insights may be used to inform, predict and influence healthcare decisions. Some insights may also be used for market research, or clinical research purposes.

Application 100 and platform 14 may be configured to interoperate in manners disclosed herein, e.g., to collect patient data, encourage patients 18 to achieve their health goals, and to influence patient behaviour.

In an example, application 100 and platform 14 may be configured to collect patient data via one or more computer applications (or widgets). As will be detailed below, these computer applications may present various tasks to patients 18 (e.g., to log their activities, moods, etc., and/or to perform particular activities). These tasks may be referred to herein as Health Quests 26. In an embodiment, the widgets may present one or more tasks in the form of a game for a patient 18 to play. In an embodiment, the widgets may offer and provide rewards (e.g., points) for completion of certain tasks, to thereby incentivize a patient 18 to complete those tasks.

In another example, application 100 and platform 14 may be configured to collect patient data from communications between patients 18 and members of their Circle of Support. In an embodiment, platform 14 may be configured to encourage communication between patients and members of their Circle of Support, e.g., by suggesting particular messages for transmission. The particular messages may be tailored according to insights generated for a particular patient, e.g., to reflect a reported or inferred condition or event. In an embodiment, platform 14 may be configured to assist communication between patients 18 and members of their Circle of Support, e.g., by providing automatic translation between technical language (including medical terms) and plain language.

Platform 14 may analyze collected data and generate insights relating to patient health. Platform 14 may generate documents (e.g., reports, agendas, memorandums, SOAP notes) including collected data and/or one or more generated insights. Such documents may also be used to automate and/or simplify data collection/entry for health care professionals (e.g., physicians or nurses). Such documents may also present actionable health intelligence data for patients 18, members of their Circle of Support, or third-parties such as, for example, clinical researchers and marketers.

In an embodiment, platform 14 may be configured to maintain a library of computer applications (which may also be referred to as widgets). A widget within this library may be configured to encourage or instruct a patient 18 to perform certain tasks. Tasks may include, for example, logging patient activity (e.g., taking medication), logging moods, logging patient metrics (e.g., weight, blood pressure, etc.). So, a widget may be configured to solicit and collect this patient data. Tasks may also include, for example, communicating with members of patient's Circle of Support, or performing certain activities (e.g., taking medication). Tasks may include a set of actions (e.g. 26a, 26b, 26c of FIG. 7), to be performed over time by a patient 18, with the aim of achieving specific health or wellness outcomes. Tasks presented by way of such a widget may be referred to herein as a Health Quest 26.

Figure 27:
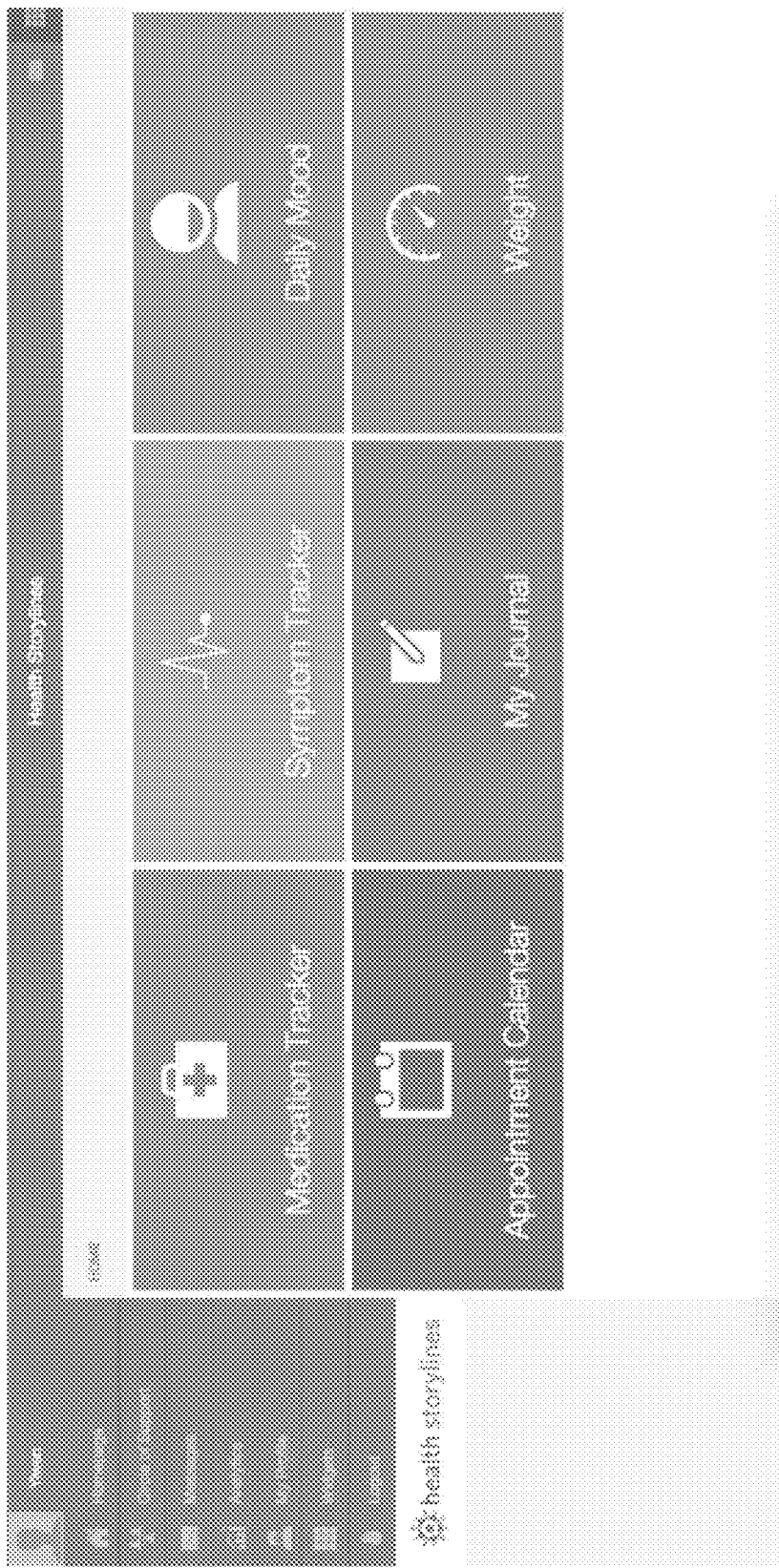
FIG. 27 illustrates an example user interface for providing access to a plurality of widgets, in accordance with an embodiment.

FIG. 27 depicts an example interface presented to a patient 18 showing a selection of widgets for the patient 18 to use. As shown, the widgets include a medication tracker widget, a symptom tracker widget, a mood tracker widget, an appointment calendar widget, a journal widget, and a weight tracker widget.

Figure 28:
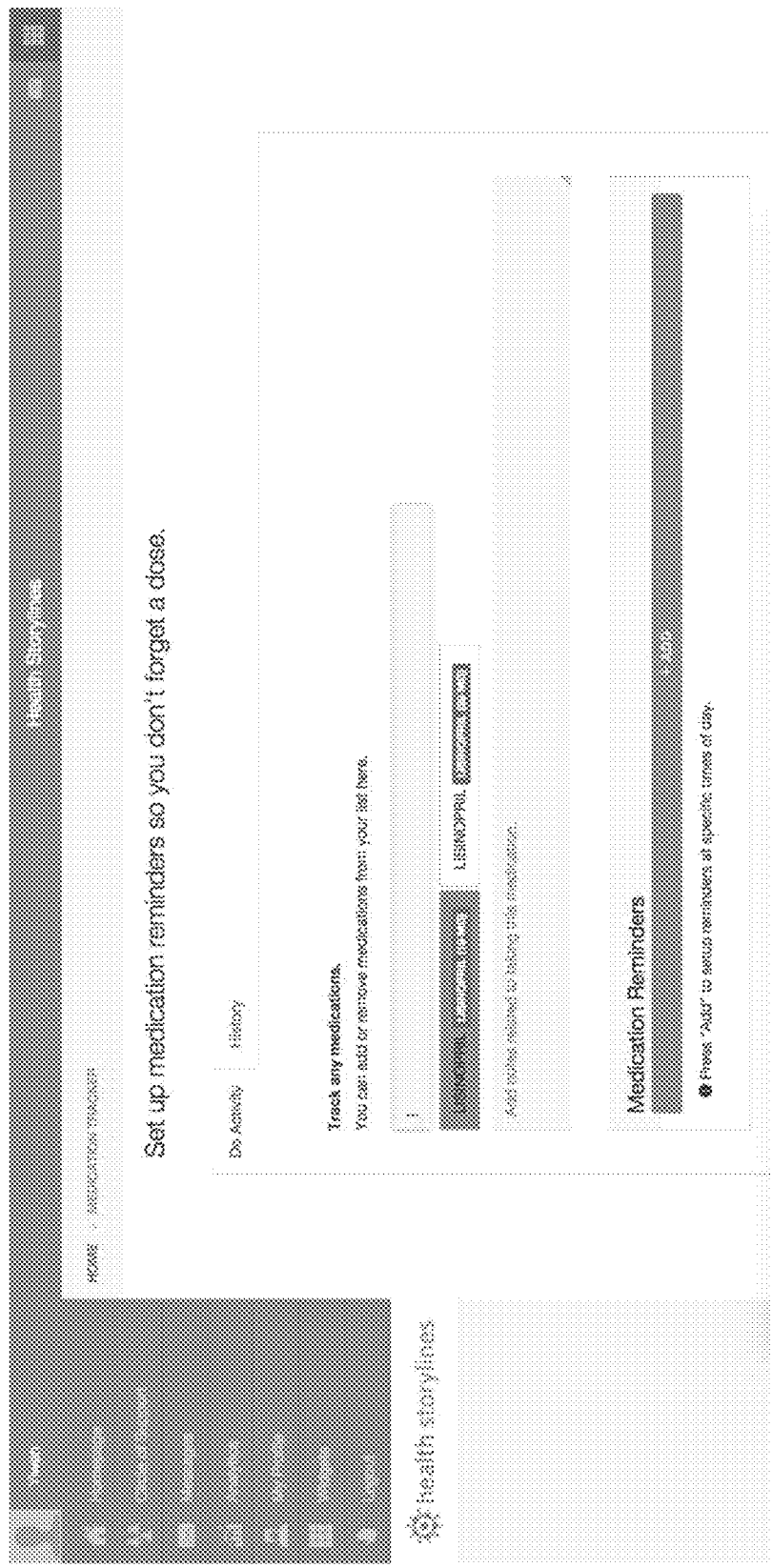
FIGS. 28-33 illustrate example user interfaces of the widges of FIG. 27, in accordance with an embodiment.

As shown in FIG. 28, the medication tracker widget asks a patient 18 to record their medications and a dosage schedule. A patient 18 may enter medications by searching within a database of medications stored at platform 14. Conveniently, platform 14 may be configured to transmit reminders to patients 18 to take medications according to the entered schedule. Patients 18 may confirm that they have taken the medication, which will be logged by platform 14.

Figure 29:
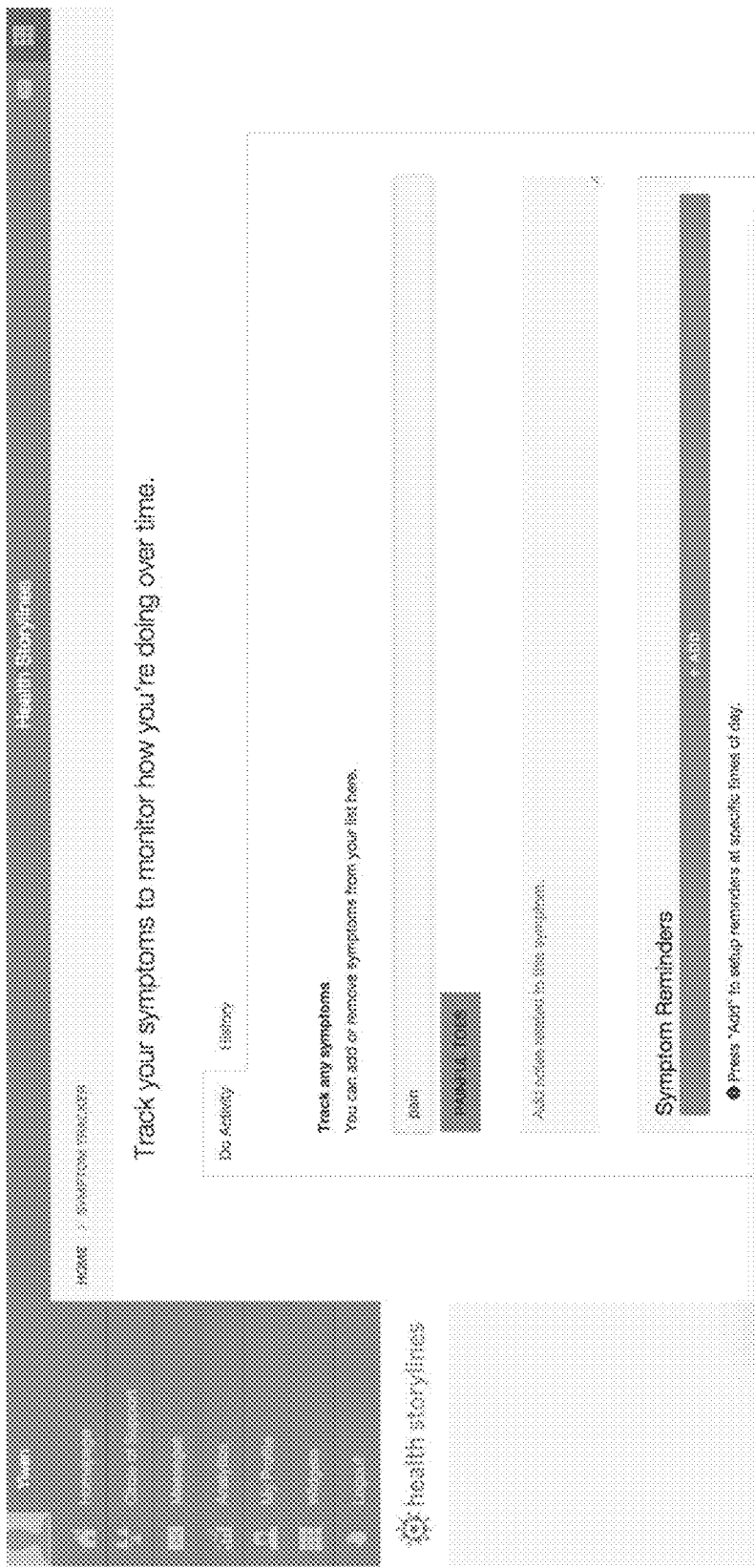

As shown in FIG. 29, the symptom tracker widget asks a patient 18 to record their symptoms, and optionally a degree to which the symptom is presented (e.g., a degree of pain or discomfort). A patient 18 may enter symptoms by searching within a database of symptoms, stored at platform 14.

Figure 30:
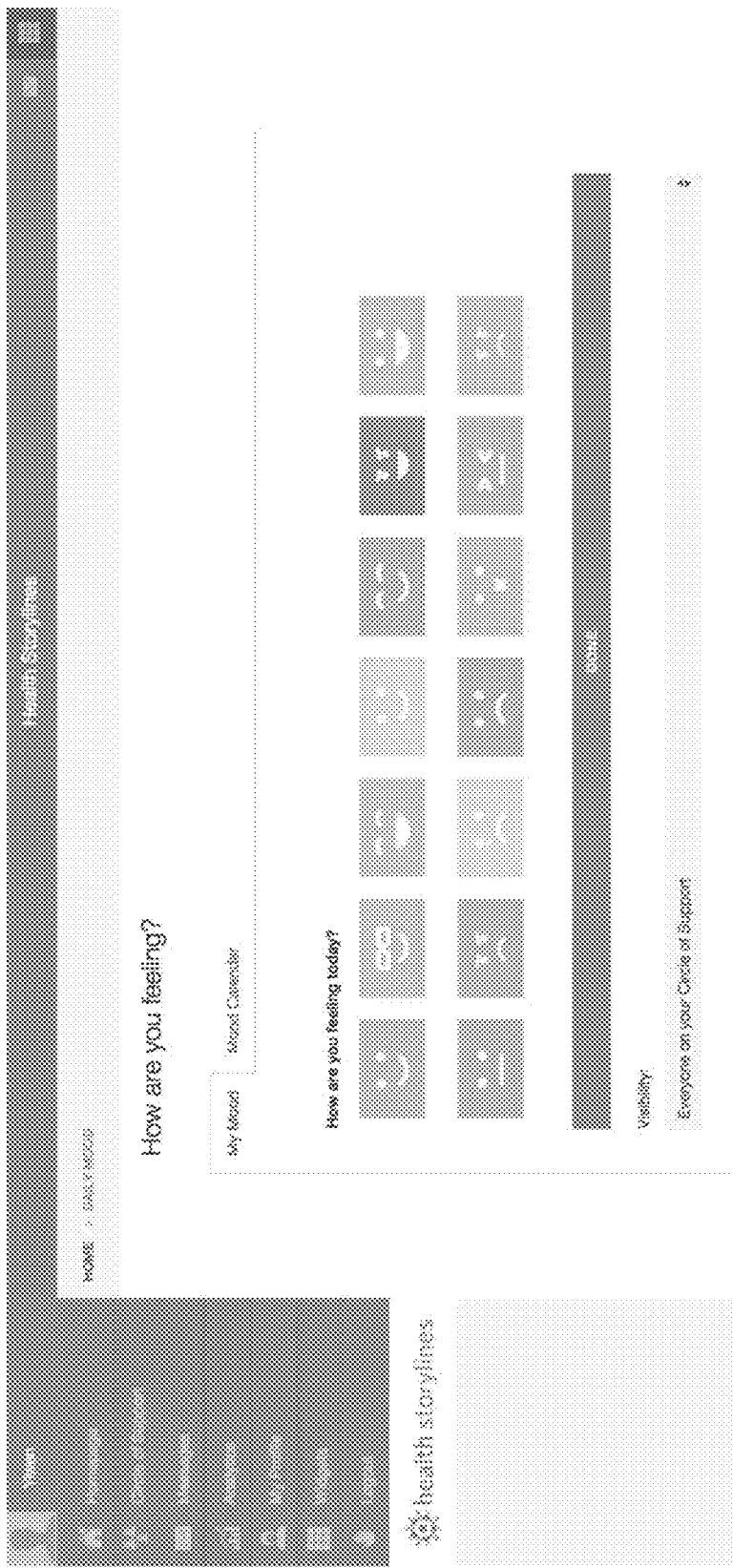

As shown in FIG. 30, the daily mood tracker widget asks a patient 18 to record their mood. The mood may be selected by the patient from a pre-defined set of moods, as represented using icons or other types of images. The patient 18 may also select the desired level of visibility for the recorded mood. For example, it may be visible to all members of the Circle of Support, or optionally it be visible to selected members or users.

Figure 31:
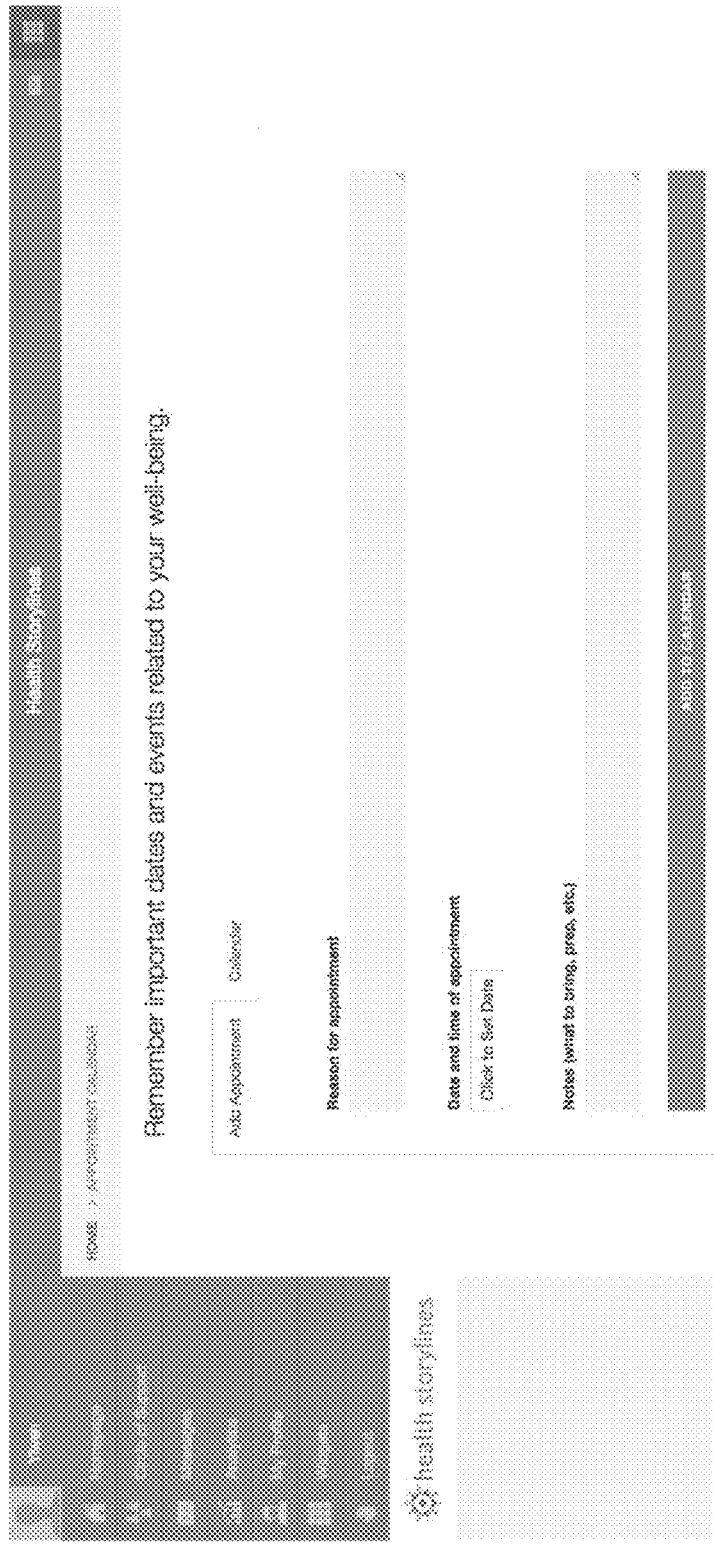

As shown in FIG. 31, the appointment calendar widget asks a patient 18 to record important dates and event related to the patient's well-being (e.g., appointments to visit a physician).

Figure 32:
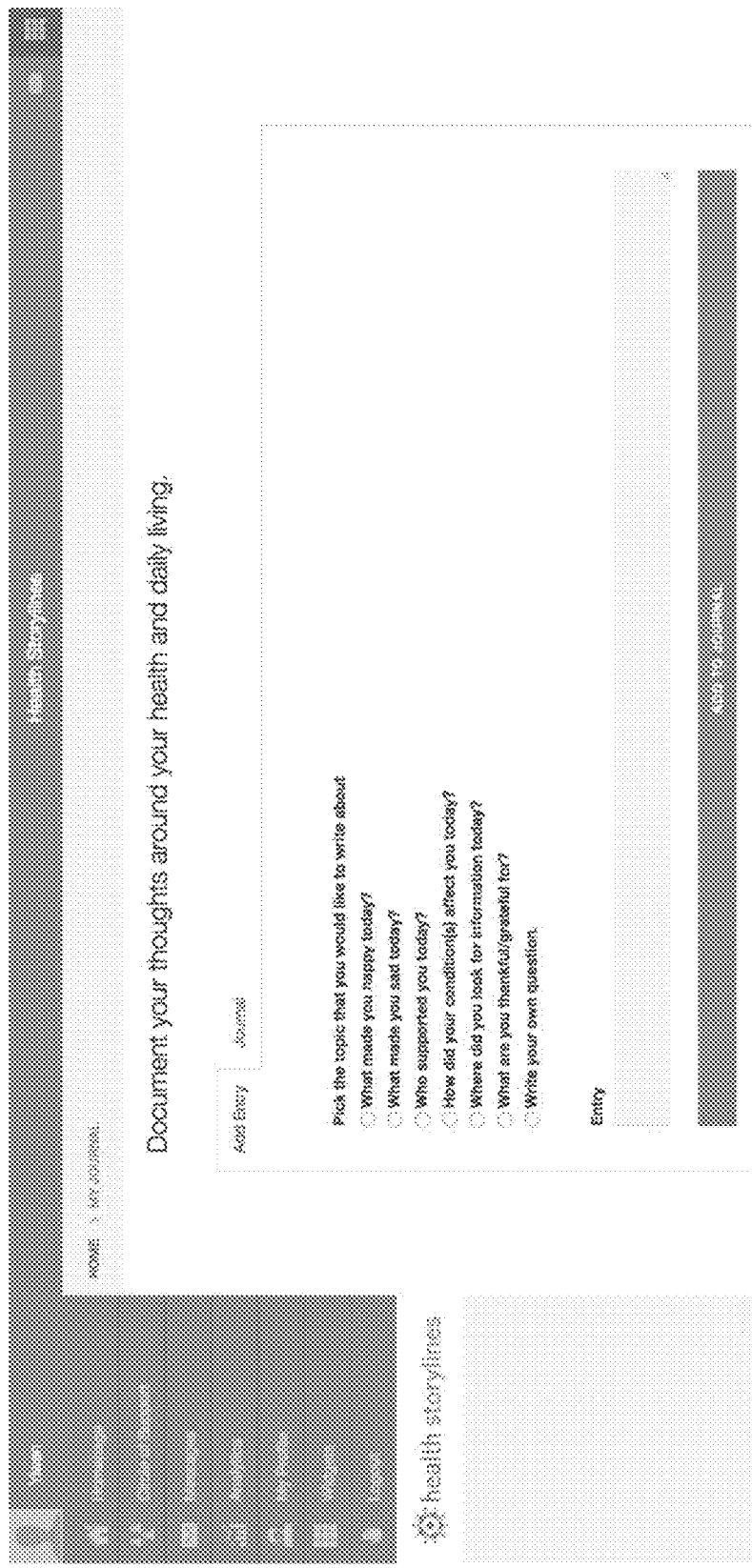
Figure 33:
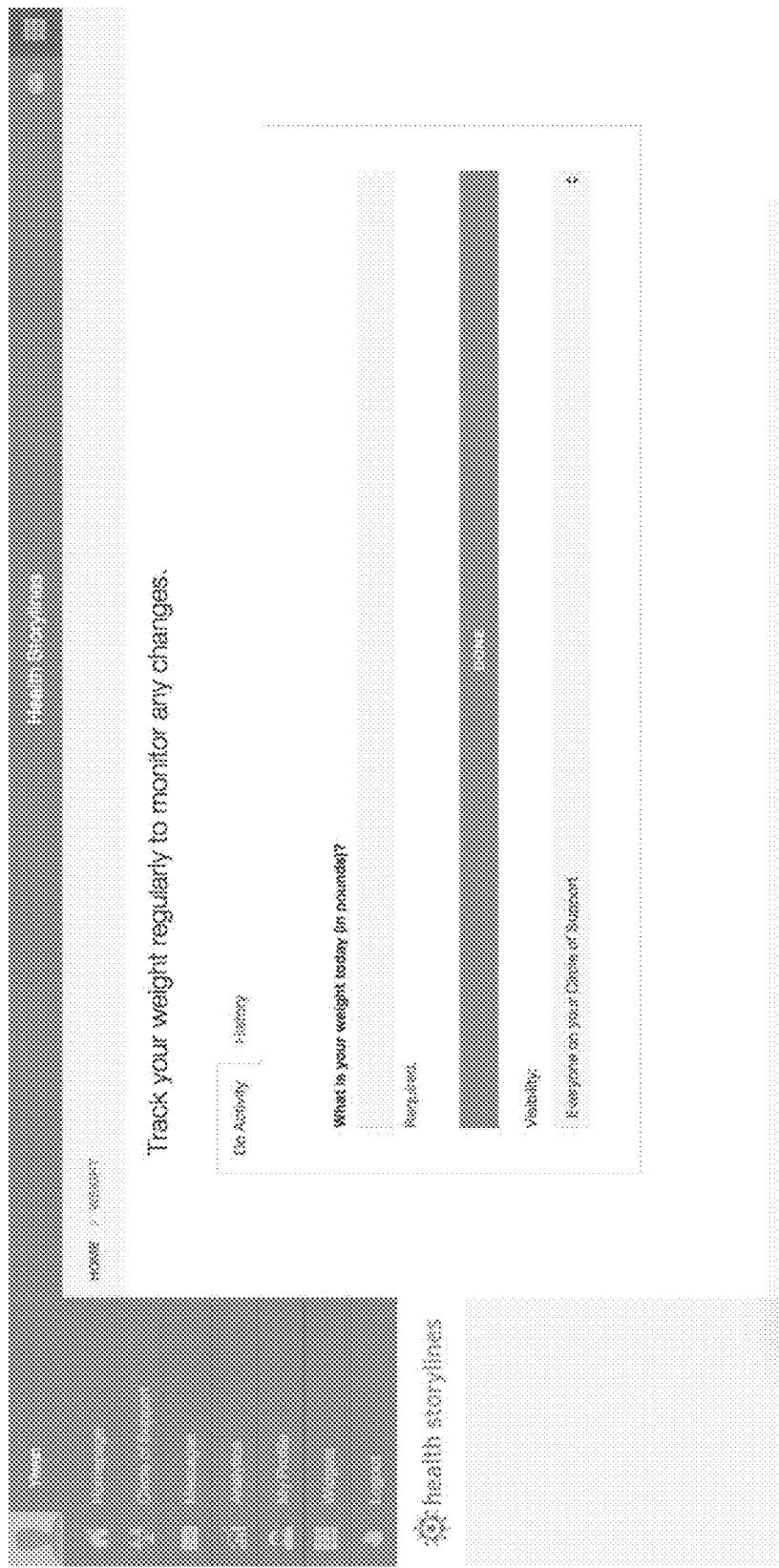

As shown in FIG. 32, the journal widget asks a patient 18 to enter his/her thoughts and feelings in a guided journal. The patient may pick from a list of suggested topics, or enter text freely. In an embodiment, platform 14 may generate guided questions based on analyzing other data collected for the patient. For example, platform 14 may guide journal entry to focus on the patient's adherence to a medical regimen if the patient has not been taking medications according to schedule. As shown in FIG. 33, the weight tracker widget asks a patient to record their weight periodically (e.g., daily).

Figure 34:
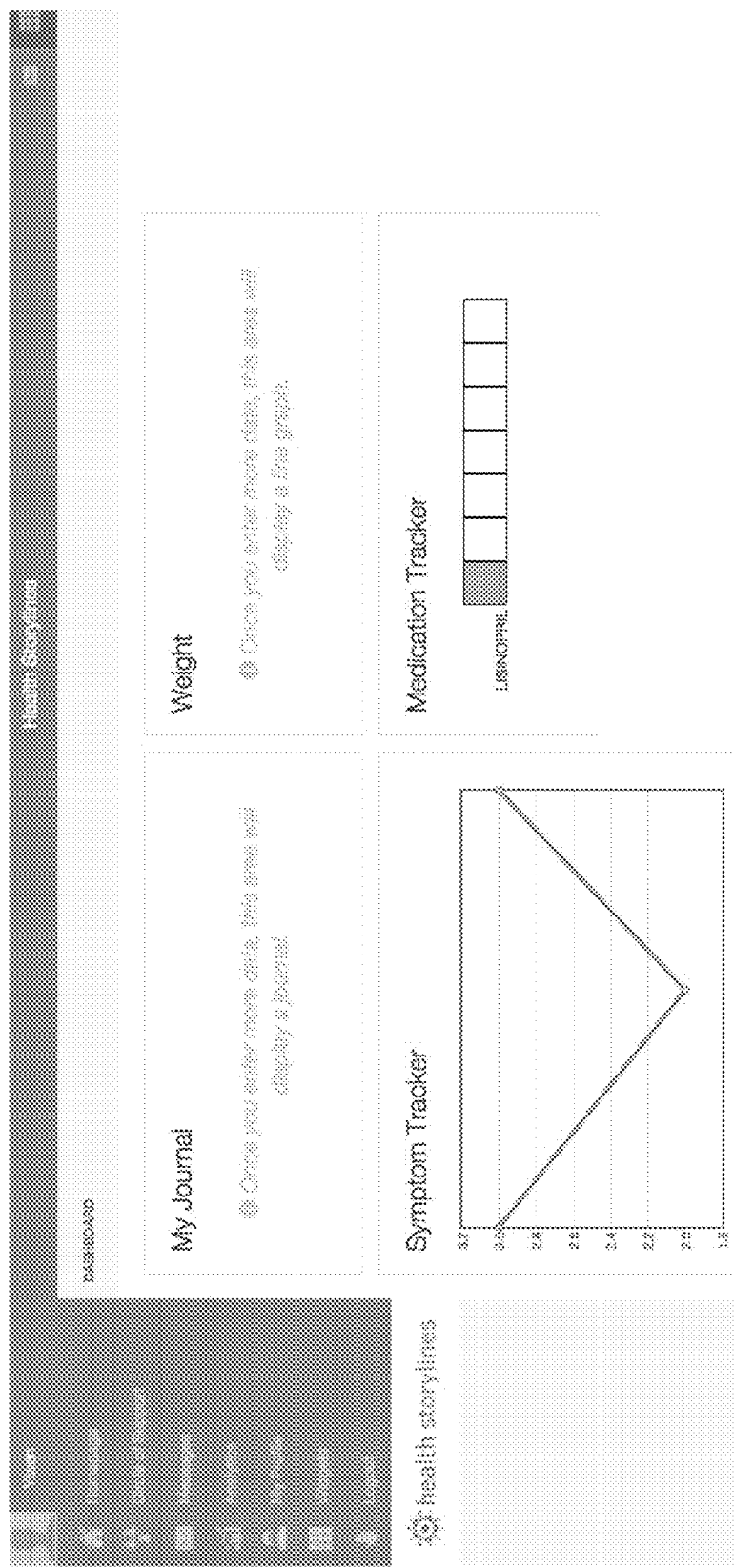
FIG. 34 illustrates an example user interface for presenting collected patient data, in accordance with an embodiment.

As shown in FIG. 34, platform 14 may present an interface allowing a patient 18 (or members of his/her Circle of Support) to view patient data collected by way of one or more widgets. The interface may be configured to show trends over time (e.g., changes in the severity of a symptom). Conveniently, this interface allows patients 18 to visualize how platform 14 is helping them manage their condition. This feedback may function as positive reinforcement and help establish a therapeutic relationship between a patient 18 and platform 14.

In an embodiment, at least some of the widgets within the library maintained at platform 14 may be categorized according to particular health conditions (e.g., Alzheimer's, an anxiety disorder, asthma, etc.). Such widgets may, for example, be configured to present tasks applicable to a particular health condition. In one example, a widget associated with an eating disorder may be configured to solicit information from a patient 18 regarding food intake. In another example, a widgets associated with Alzheimer's may present tasks relating to memory exercises. Widgets may also be categorized according to other criteria, e.g., patient demographics, particular drugs, particular health organizations, particular geographic areas, etc.

In an embodiment, platform 14 may automatically identify one or more widgets (or Health Quests 26) of interest to a particular patient 18, e.g., by matching the patient's health condition and the health condition associated with the widget, or by identifying applications popular amongst other patients 18 sharing one or more health conditions. Platform 14 may recommend identified widgets to a patient 18 for access, e.g., by way of notifications presented through application 100. Widgets may also be automatically matched and recommended to patients according other criteria (e.g., based on drugs that a patient is taking, organizations with which the patient is associated, research studies in which the patient is participating, etc.).

A widget may be executed at platform 14 and/or at device 12. A widget may be retrieved by a device 12 from platform 14 for execution at device 12. In an embodiment, application 100 may maintain a personalized library of widgets for a particular patient 18 at device 12. Patients 18 may add or remove widgets to/from this personalized library. Platform 14 and/or application 100 may automatically add or remove widgets to/from this personalized library. For example, platform 14 and/or application 100 may automatically add a widget predicted to be of interest to a particular patient 18.

In an embodiment, platform 14 and/or application 100 may be configured to allow a member of a patient's Circle of Support to recommend a particular widget. In an embodiment, platform 14 and/or application 100 may be configured to allow a member of a patient's Circle of Support to add or remove a widget from a patient's personalized library.

For example, Circle of Support members can identify a widget for use by a patient 18 based on their knowledge of that patient 18. Circle of Support members can also configure a widget and particular tasks based on their knowledge of that patient 18. For example, a Circle of Support member may know that a particular patient 18 is allergic to milk, and can thus avoid milk in his or her suggestions of healthy diet as a task (i.e., a Health Quest 26).

Figure 7:
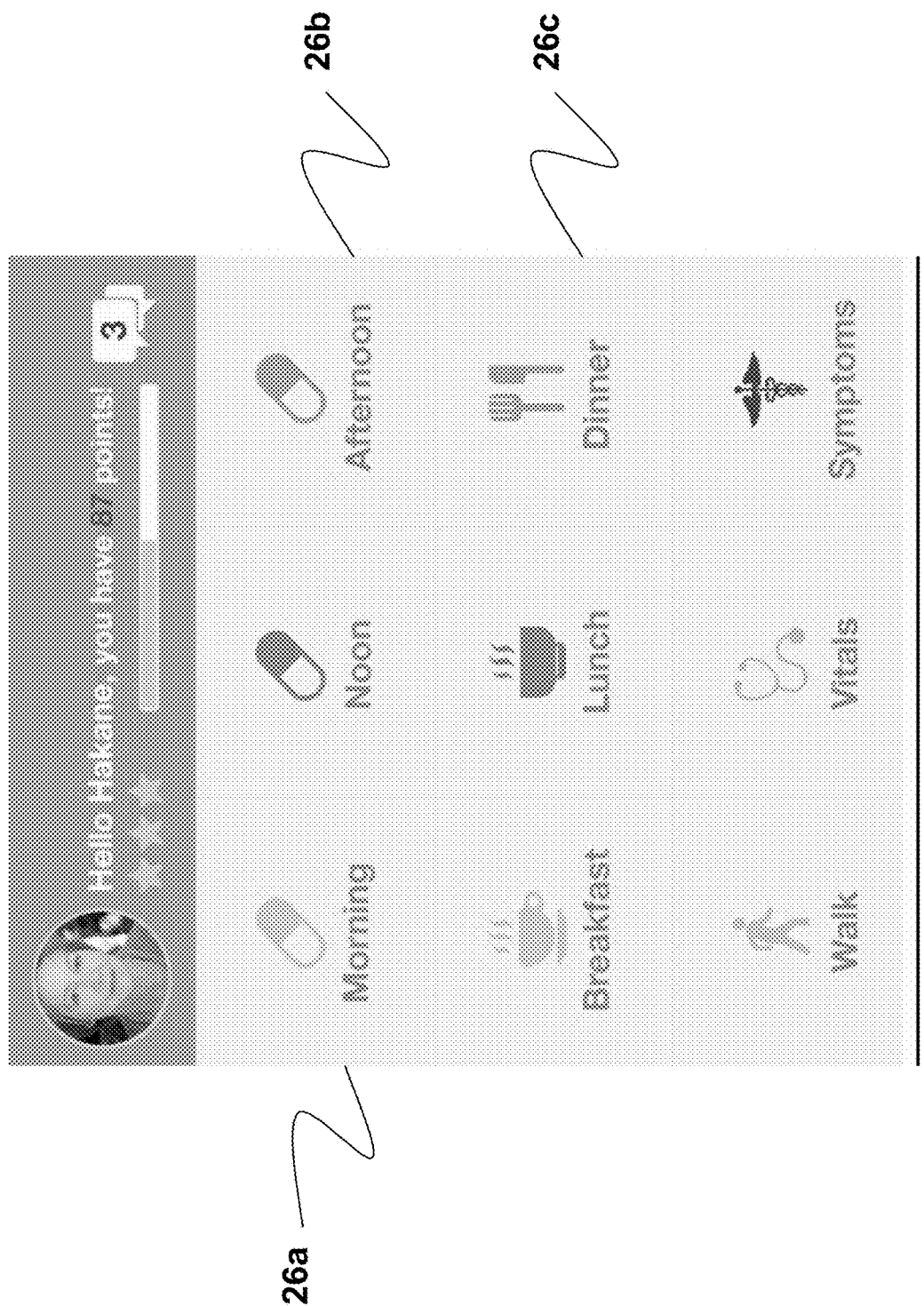
FIG. 7 illustrates several example Health Quests, in accordance with an embodiment.

In an embodiment, as shown in FIG. 7, Health Quests 26a-26c (corresponding to one or more widgets) are presented to a patient 18 via an intuitive 3×3 keypad-style grid through application 100 on a device 12. Time-sensitive Health Quests 26 can trigger the generation of one or more reminders and notifications through application 100.

A patient 18 can fulfil specific goals of the Health Quests 26 by, for example, engaging in real-life actions, and/or recording his or her actions in application 100 through various types of data entry by the patient 18, including text, photo, video, etc.

Health Quest 26 data that have been recorded by the patient 18 can be further presented to Circle of Support members for feedback, which may in turn be sent to patient 18 by way of application 100. For example, Circle of Support members can send feedback to the patient via text, image, or thumbs up/down.

In an embodiment, platform 14 may automatically monitor a patient's performance of particular Health Quests 26, and evaluate performance (e.g., based on degree of completion or timeliness of completion). On the basis of this evaluation, platform 14 may automatically notify one or more Circle of Support members and recommend particular feedback automatically tailored to the evaluation. Platform 14 may automatically select a particular Circle of Support member to receive such a notification and recommendation based on a role of the member compared to the particular nature of the Health Quest 26. For example, platform 14 may select a nutritionist from among Circle of Support members to provide feedback if the Health Quest 26 relates to a food-intake task.

Figure 9A:

At any given time, a patient 18 can communicate with any member of his/her Circle of Support (e.g. to ask for support, information), as shown in FIG. 9a. In an embodiment, communication between a Circle of Support member and patient 18 may be transmitted via a messaging platform built within application 100. In another embodiment, the messaging platform may be provided by an entity or utility outside of application 100 but coupled to application 100 via a suitable communication channel (e.g., inter-process communication).

Figure 6A:
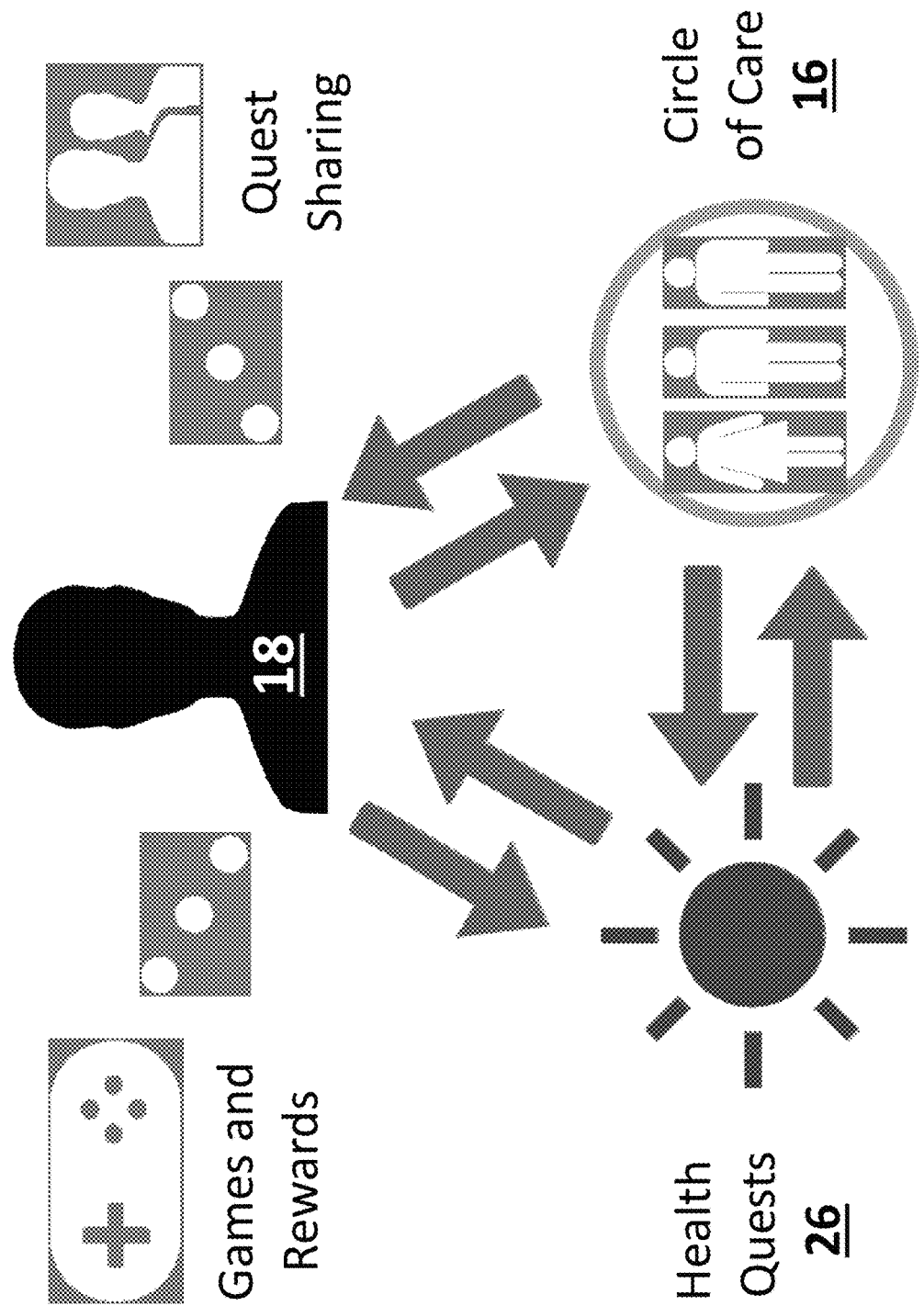
FIGS. 6a and 6b illustrate relationships between a patient, a Circle of Support, and Health Quests, in accordance with an embodiment.
Figure 6B:
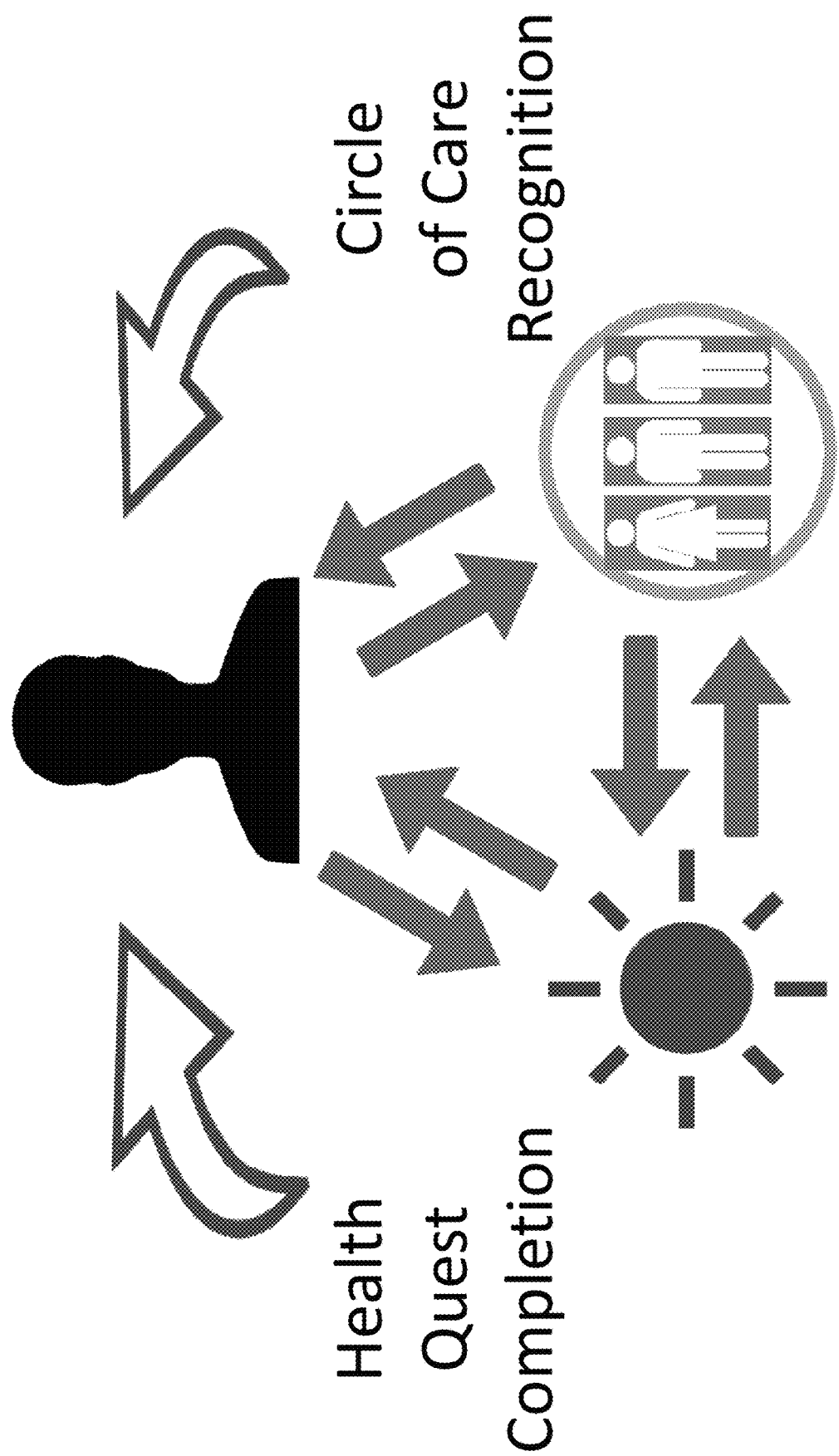

As shown in FIG. 6a, the Health Quests 26, Circle of Support members, and a patient 18 may interact in the manner of a feedback loop. In an embodiment, games, rewards, points, or quest sharing (e.g. via social network such as Facebook™) can be provided to encourage and sustain patient health activities and interactions between patient 18 and a Circle of Support member. As illustrated in FIG. 6b, regular feedback from Circle of Support members may promote sustained interest, so that the patient 18 can sustain motivation to keep completing Health Quests 26 along their journey of recovery.

Figure 2:
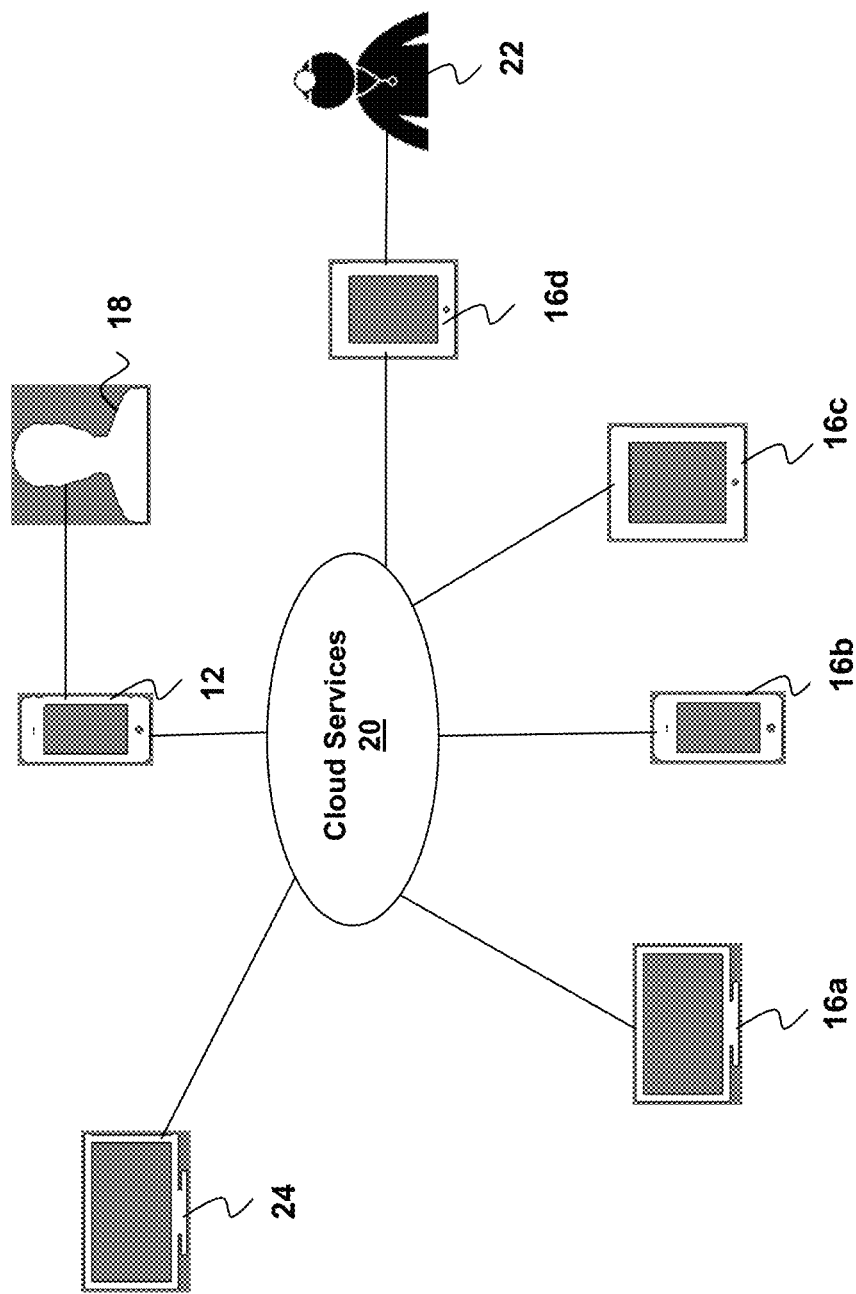
FIG. 2 illustrates a system for analyzing and enhancing patient health, in accordance with an embodiment.

FIG. 2 illustrates an exemplary system diagram in accordance with another aspect. As shown, platform 14 may be implemented as a cloud service, a cluster service or simply a cluster hosted in cloud, or a router server configured based on certain configurations.

In an embodiment, platform 14 may be remotely or closely coupled with one or more application 100 on one or more devices 12 (or devices 16), and comprise entirely of software, or entirely of hardware, or include both software and hardware components. Platform 14 may be implemented to one or more server computers, or may be implemented using an interconnected network of computer residing at the same or different physical locations, and connected to one or more application 100 and the core network through one or more trusted network connections. Application 100 can interoperate with platform 14 and/or the other components in the depicted network architectures to implement the functionalities described herein.

Application 100 and/or platform 14 may be configured to combine a set of features that work synergistically. For example, various Health Quest 26a, 26b, and 26c, related to the same health-related goal, activity or intervention may be presented to a patient 18. By supporting a variety of quests types, application 100 and/or platform 14 may enable the patient 18 to simultaneously manage diverse health and self-care needs.

Figure 8:
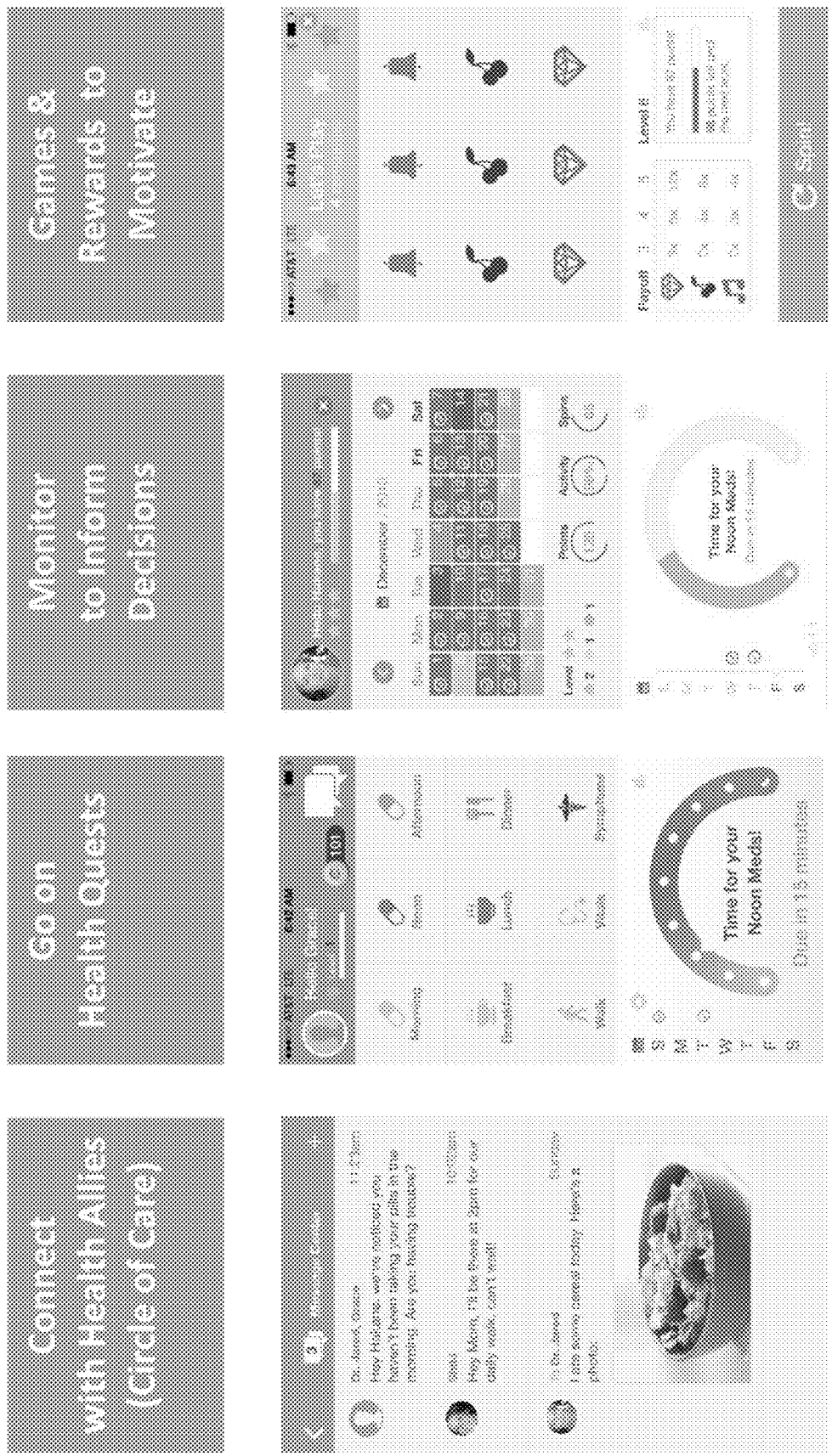
FIG. 8 illustrates example user interfaces of a system for analyzing and enhancing patient health, in accordance with an embodiment.

As shown in FIG. 8, application 100 may be configured to include other features to augment and facilitate a patient 18's completion of Health Quests 26, and in turn to help the patient 18 stay on track with recovery. For example, application 100 may be configured to provide simplified integration with external devices (e.g., external devices 17 of FIG. 1) and relevant health applications (e.g., for diabetes nutrition, counting calories, medical queries, etc.).

As noted, external devices 17 may include one or more RFID tags attached to objects with which a patient 18 may interact. Each RFID tag may encode an identifier that uniquely identifies the object to which it is attached. In one example, an RFID tag may be attached to a pill bottle of patient 18. When a patient 18 takes a pill from that bottle, he/she may present his/her device 16 to the RFID tag to receive the identifier encoded by the RFID tag. In this way, the patient 18 may notify application 100 that the pill has been taken. Any existing reminders for taking the pill configured at application 100 and/or platform 14 may be cleared, and a new reminder may be set or activated for the next time the patient is scheduled to take a pill from the bottle.

Conveniently, such features enable patients 18, as well as members of their Circle of Support to simplify and streamline the complexity of health and self-care management. Some external devices may provide data automatically to one or more widgets. For example, a weight scale may automatically provide a patient's weight to the weight tracker widget.

Health Quests 26, associated events (e.g. patient 18 taking medication on time, eating a healthy meal or measuring his or her weight), and related data may be recorded by application 100 and optionally stored elsewhere such as, e.g., at platform 14 or in a storage medium on cloud services 20.

Optionally, events or actions detected by mobile device 12 but not actively entered into application 100 by patient 18 may also be recorded. For example, an iPhone™ GPS sensor may be able to detect that a patient 18 has walked 2 kilometers and such an event may be sent to application 100. For another example, application 100 may connect with an automated drug dispenser and receive information that a medication has been dispensed to patient 18. All these events and their associated data, whether directly related to one or more Health Quests 26, may be recorded by application 100 and stored on cloud services 20 or in a local memory of mobile device 12, for later processing and/or reporting.

In an embodiment, application 100 and/or platform 14 may be configured to log information regarding communication and interactions amongst patients and Circle of Support members, such as postings, email, texting, speech and so on. For example, application 100 and/or platform 14 may be configured to allow Circle of Support members to recommend articles or other relevant information through the application 100 to each other and to the patient 18. In an embodiment, platform 14 may automatically identify information as being relevant to a particular patient 18 (e.g., scientific articles), e.g., based on analyzing data collected for that patient. For example, information may be identified as being relevant to the patient on the basis of particular drugs being taken by that patient, the patient's health condition(s), etc. Such information, upon being identified, may be automatically presented to patients 18 or Circle of Support members.

Data from multiple sources or multiple patients can be aggregated by platform 14 in a database connected locally or remotely, or using cloud services 20.

Platform 14 and/or application 100 may be configured to allow patients 18 to build their own Circle of Support by reaching out to their most trusted supporters which could include spouse, children, family physician, therapist, social worker, community nurse, friends and even peers with similar disease experience. In an embodiment, candidates for a Circle of Support may be automatically identified and suggested to patients 18. Patients can send personal invitations to their most trusted supporters, along with a link to the application 100 (e.g. via a Circle of Support interface on any one of devices 16a, 16b, 16c, 16d).

Figure 10:
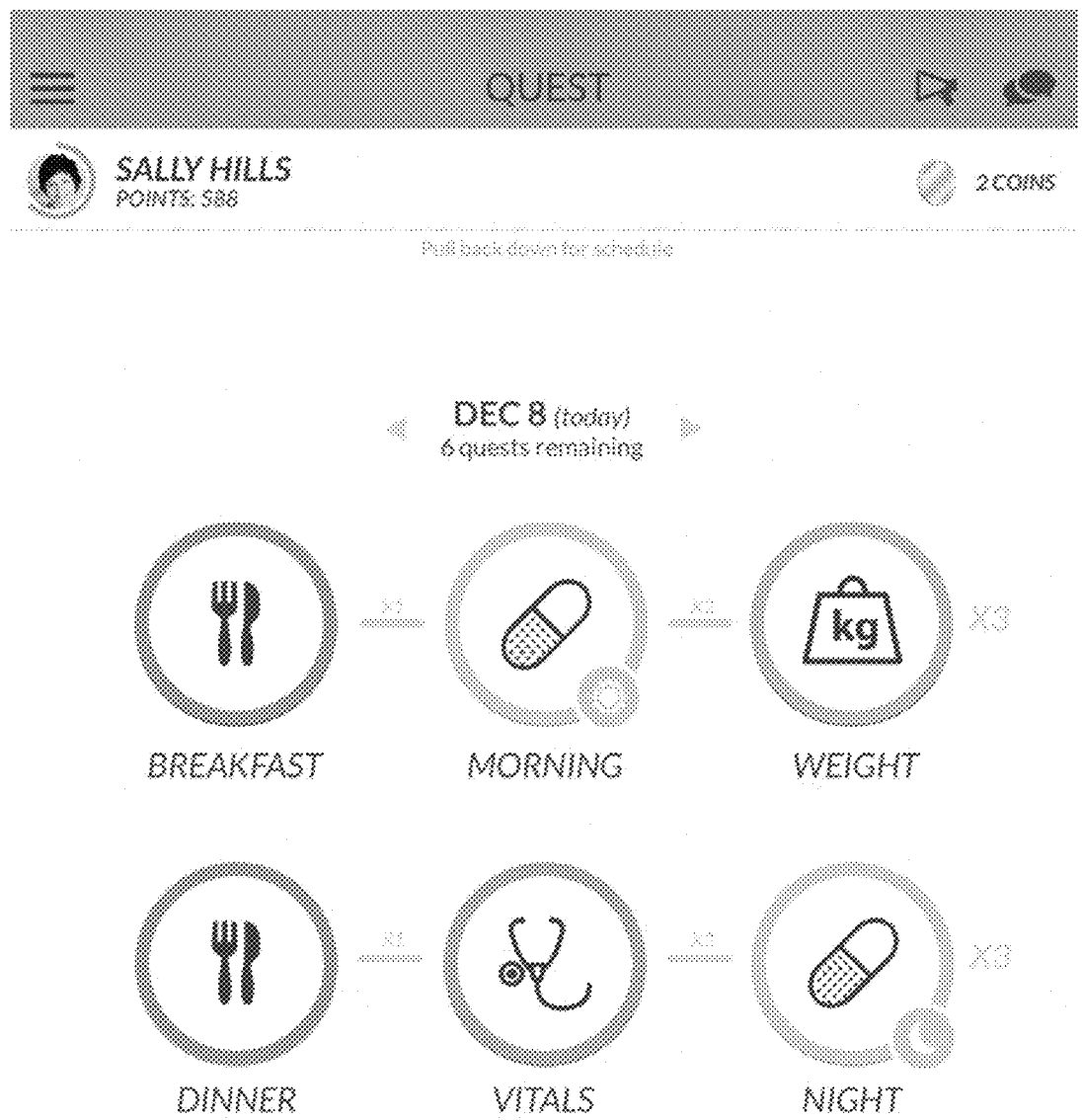

One or more Health Quest 26 (see e.g. FIGS. 7 and 10) implemented in one or more widgets may be tailored to the individual patient's circumstances and configured either by the Circle of Support members or by patients themselves based on post-discharge or post-consult instructions.

Figure 9C:
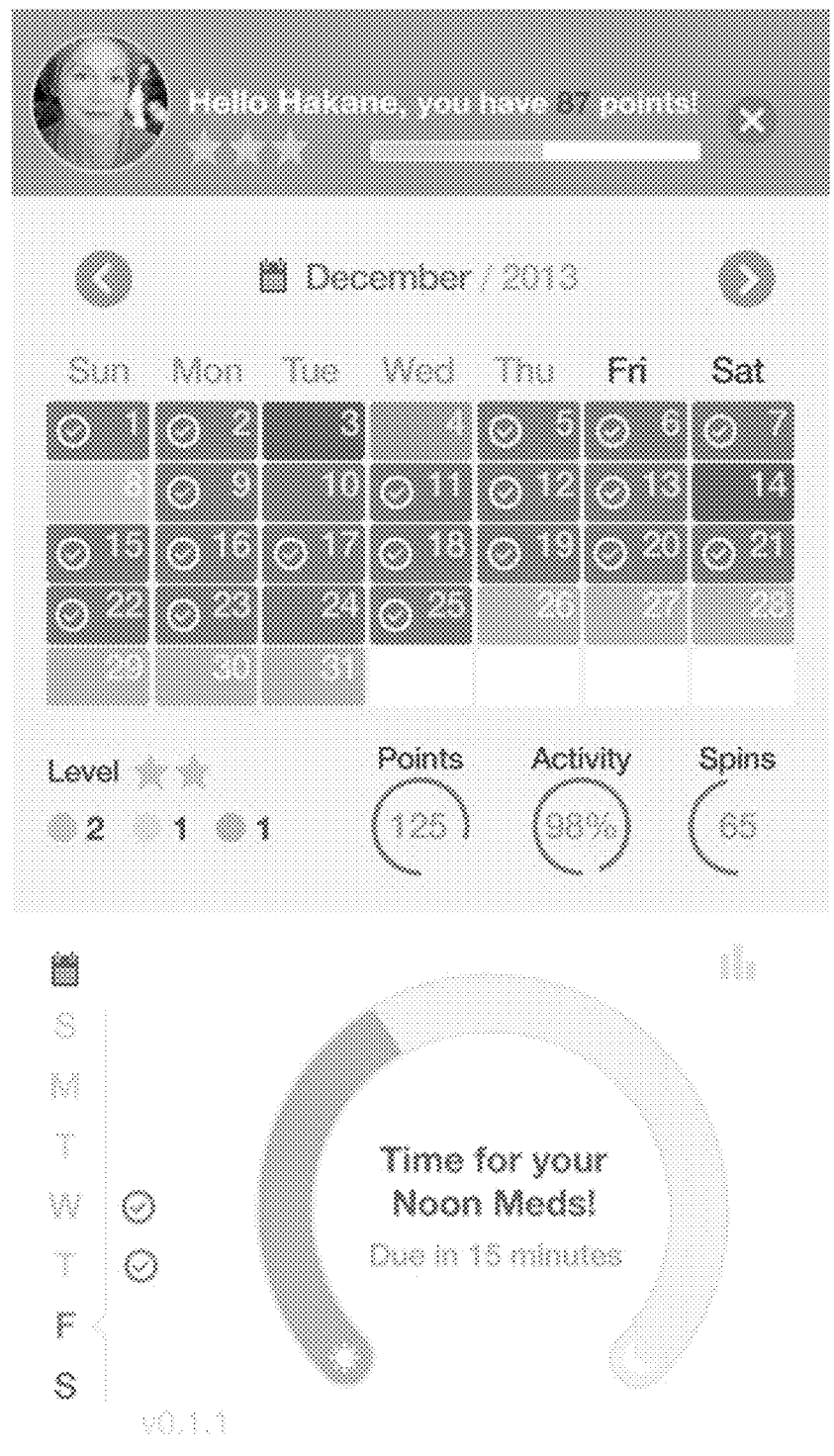

The system can support at least following Health Quest types (as may be implemented by way of one or more widgets), which may overlap with one another, and are listed here for illustrative purposes and not meant to be limiting:

Medication—Tracks adherence to prescribed medication, for example recorded by text, photo and/or dosage sliders. In one embodiment, creation of medication type of quests 26a, 26b may automatically generate alerts and/or reminders for patient 18 (see e.g. FIG. 9c).

Nutrition—Tracks food intake and diet goals, recorded by photo and/or nutrition sliders. Qualitative and quantitative metrics are extracted from submitted data.

Exercise or Fitness—Logs exercise and physical activity, including integration with wearable fitness devices.

Symptoms—Record symptoms and severity over time, plotted as a trend line.

Emotional and Spiritual—Psychosocial journal for tracking levels of motivation, happiness, satisfaction, and recording pain points.

Social—Connect and chat with Circle of Support.

Appointments—Schedule reminders for physician or healthcare provider visits, including notes and goals for follow-ups.

Education—Provide relevant links for reference and learning, including links to external websites or applications.

Lifestyle or Wellness—Provide resources on spirituality, meditation, music, art, as well as complementary and alternative medication/integrative health.

Vitals—Track vitals such as heartbeat, pulse, etc. via appropriate health-monitoring devices such as pulse oximeter, etc.

Monitoring—Track adherence to various goals such as weight, nutrition intake, exercise amount, and so on.

The types of Health Quests 26 may be customized and modified by Circle of Support members, or alternatively by a system administrator of platform 14.

As noted, the library of widgets implementing Health Quests may include widgets designed for specific diseases or conditions, and widgets may be automatically selected for a patients based on one or more characteristics of that patient. Platform 14 and/or application 100 may be configured to automate the selection and/or assignment of Health Quests 26 based on one or more of the following factors: disease, condition, selection by Circle of Support members, consensus by Circle of Support members, opinion of patient 18, recommendations by health care professionals or pharmaceutical companies, and so on.

Platform 14 and Application 100 can recognize that not all members of Circle of Support can sustain the same or consistent levels of activity, since some will be more active at certain times than others. The system (Platform 14 and Application 100) can be configured so that the other members can reach out with specific questions and so on, to make or receive suggestions. The system can facilitate efficient communications within the Circle of Support, in a way that can be specifically and expressly authorized by the patient 18 and covered by the legal agreements/consents signed by the patient(s) 18. This way the system can remove barriers to the sharing of information and support from the Circle of Support, which in turn improves the health outcomes for the patient 18.

In addition, application 100 may include mechanisms for members of Circle of Support to reach a consensus regarding the Health Quests 26 and associated incentives.

Figure 11:
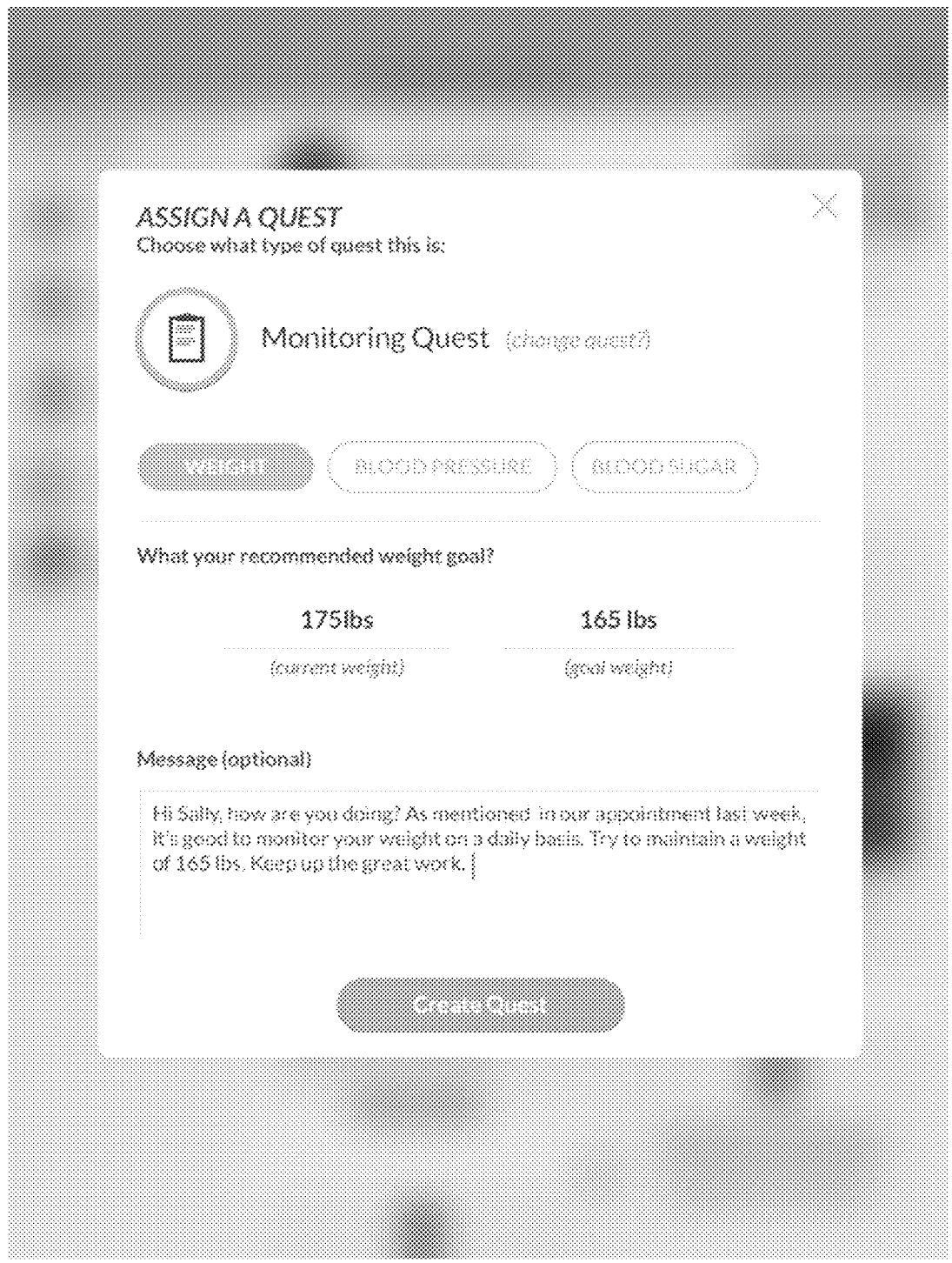

In an embodiment, as shown in FIG. 11, a Monitoring Quest 26 is being created and assigned to Sally, the patient 18. As shown, the Monitoring Quest 26 can be created for at least three subjects: weight, blood pressure and blood sugar. The creator of the Quest 26, in this case being a member of Circle of Support and Sally's doctor 16d, 22, can select weight as the monitored subject, and can further select a goal weight (e.g. 165 lbs.). The doctor 22 can also specify a current weight, or leave it to the patient 18 to fill out her current weight. The doctor 22 can further enter an optional message to the patient 18 to encourage her, for example. Even though not explicitly illustrated in the drawing, the Monitoring Quest may also be created to monitor nutrition intake, exercising amount, and all other qualities that may be monitored.

In another embodiment, Health Quests 26 may also be recommended, created and/or assigned by pharmaceutical companies who may provide a suitable medication for the patient 18 for his or her condition(s). Such recommendation, creation of assignment of Health Quests 26 may be done in collaboration with other Circle of Support members.

Once created and assigned, the Health Quests 26 may be downloaded by the patient 18 and other members of a Circle of Support. In addition, they may also be shared and rated online by friends and peers of the patient 18.

Figure 12:

As shown in FIG. 12, one or more of the assigned Health Quests 26 can be associated with a particular day or time, or location, and tracked accordingly. One or more of the Health Quests 26 may also be generated with automatic reminders. For example, if the patient 18 has Type II diabetes and is using a drug M for controlling her condition, then an automated scheduling and notifications in the forms of Health Quests 26 may be generated for the patient 18 and displayed via the user interface of application 100. As an additional feature, application 100 may be further configured to provide educational Health Quests 26 to patient 18 regarding the benefits and possible side effects of drug M for his/her condition.

Figure 13:
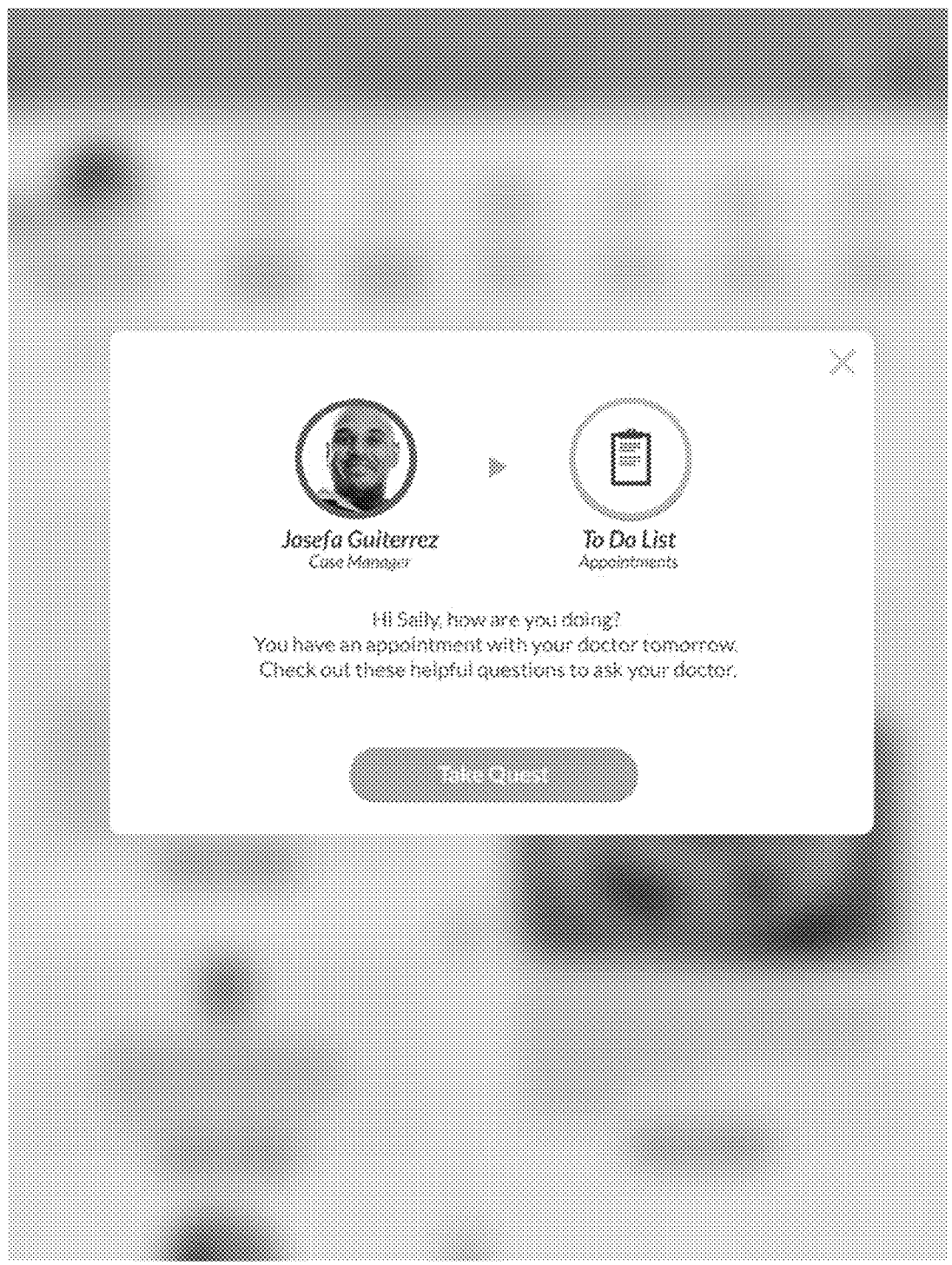
Figure 14:
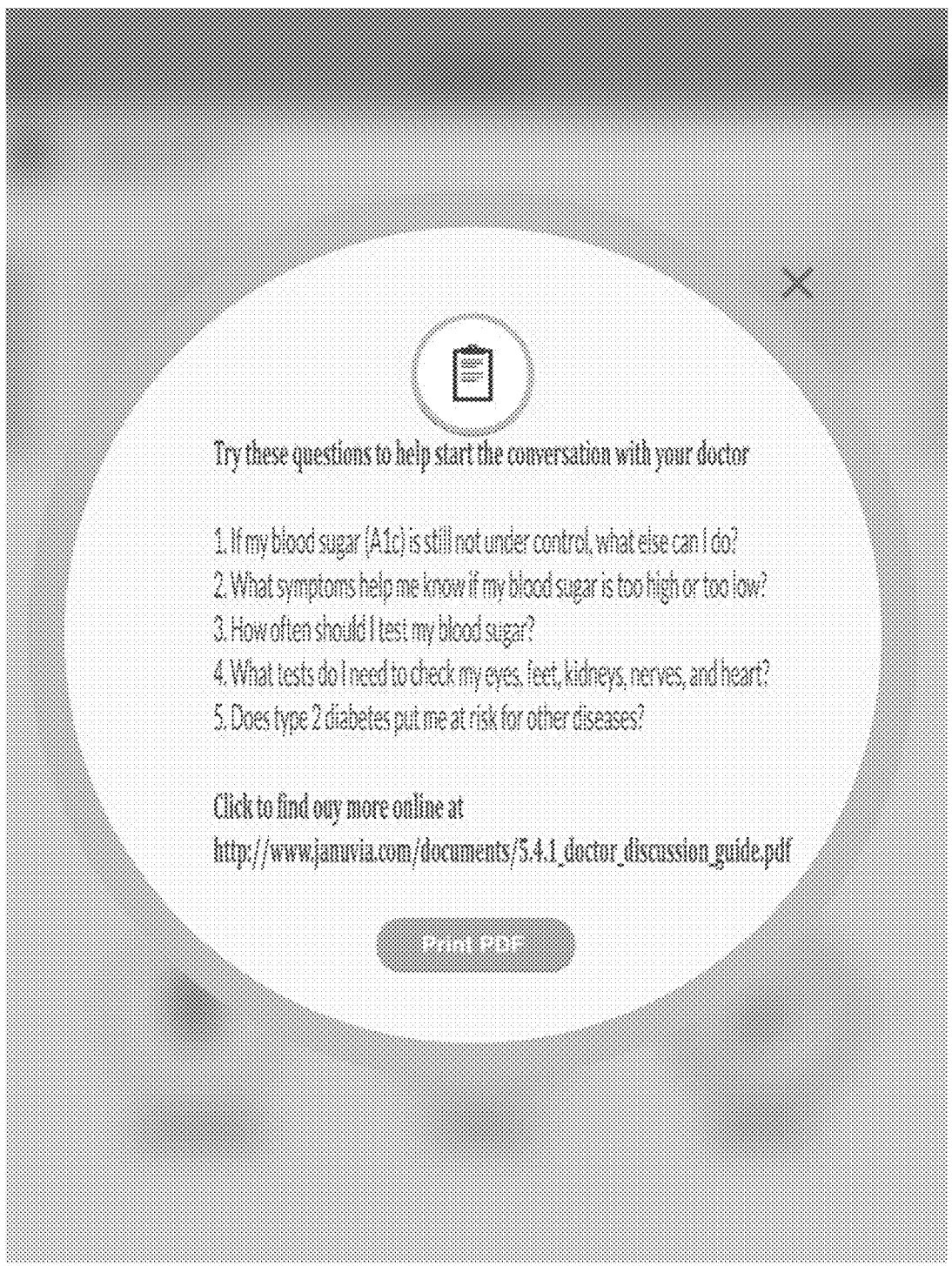

As shown in FIG. 13, an appointment Health Quest 26 may be assigned and generated with a reminder in a to-do list in application 100. At an appropriate time (e.g. 24 hours before the appointment), application 100 can deliver reminders along with the right information (e.g. suggested questions to ask a doctor, customized based on patient's condition) at the appropriate time to patient 18. FIG. 14 illustrates examples of suggested questions presented to patient 18 before an appointment.

In an embodiment, platform 14 may be configured to permit Circle of Support members to play a role in selecting the incentives, games, rewards or other parameters (collectively "incentives") that are likely to produce the best result for the patient 18. Concurrently or alternatively, application 100 can recommend and select the appropriate incentives, games, rewards or other parameters based on factors such as disease, patient profile, and so on.

Figure 15:
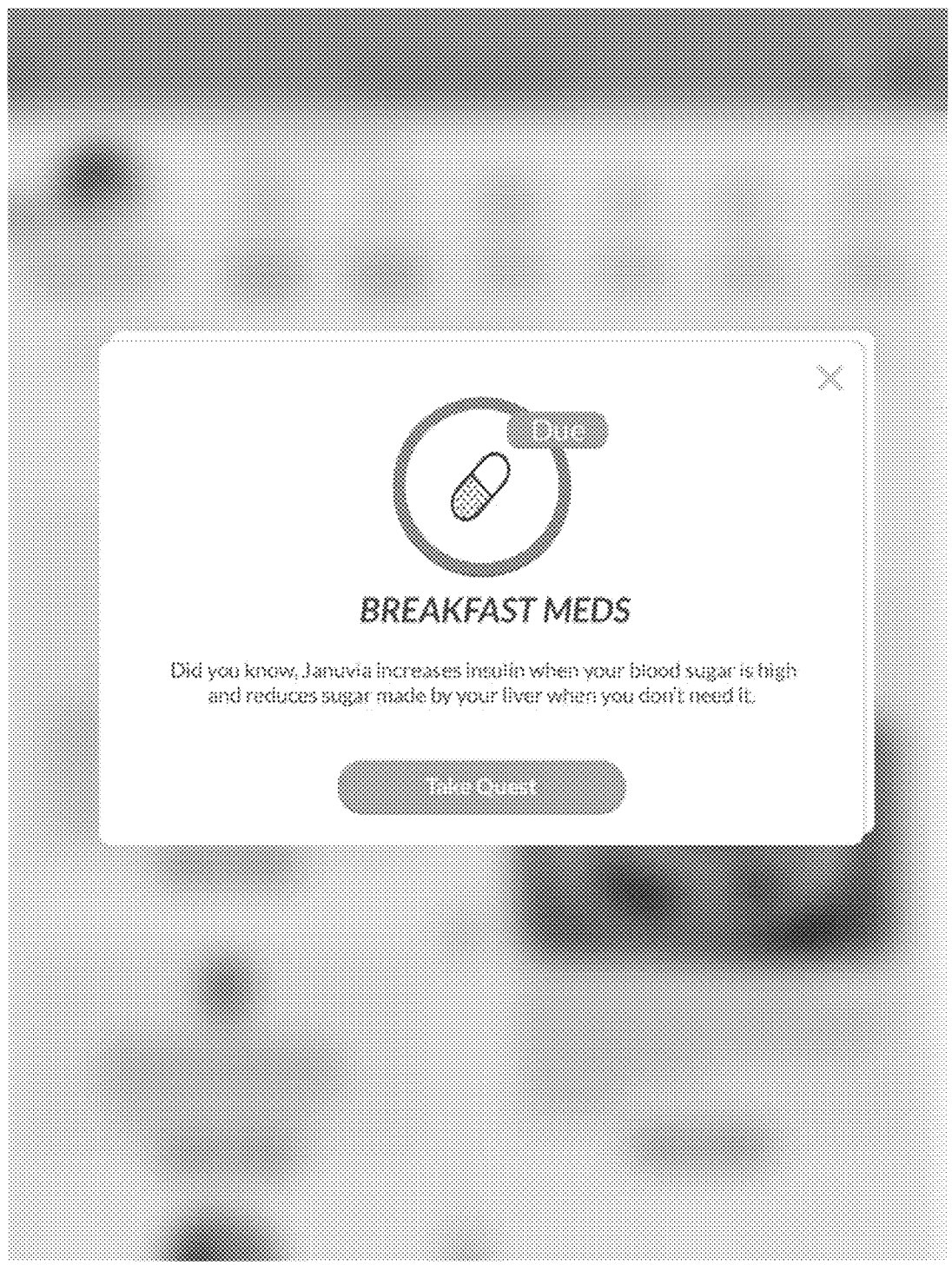

Adherence to quests, including drug or medication adherences, can be tracked by application 100 as shown in FIG. 15. This feature allows application 100 to drive adherence through push notifications. The adherence data can be tracked by application 100 and further processed by platform 14 to correlate the data with other metrics such as activity level, quest selection, doctor visits, and so on. Such data may be used to generate patient reports by platform 14.

Figure 16:
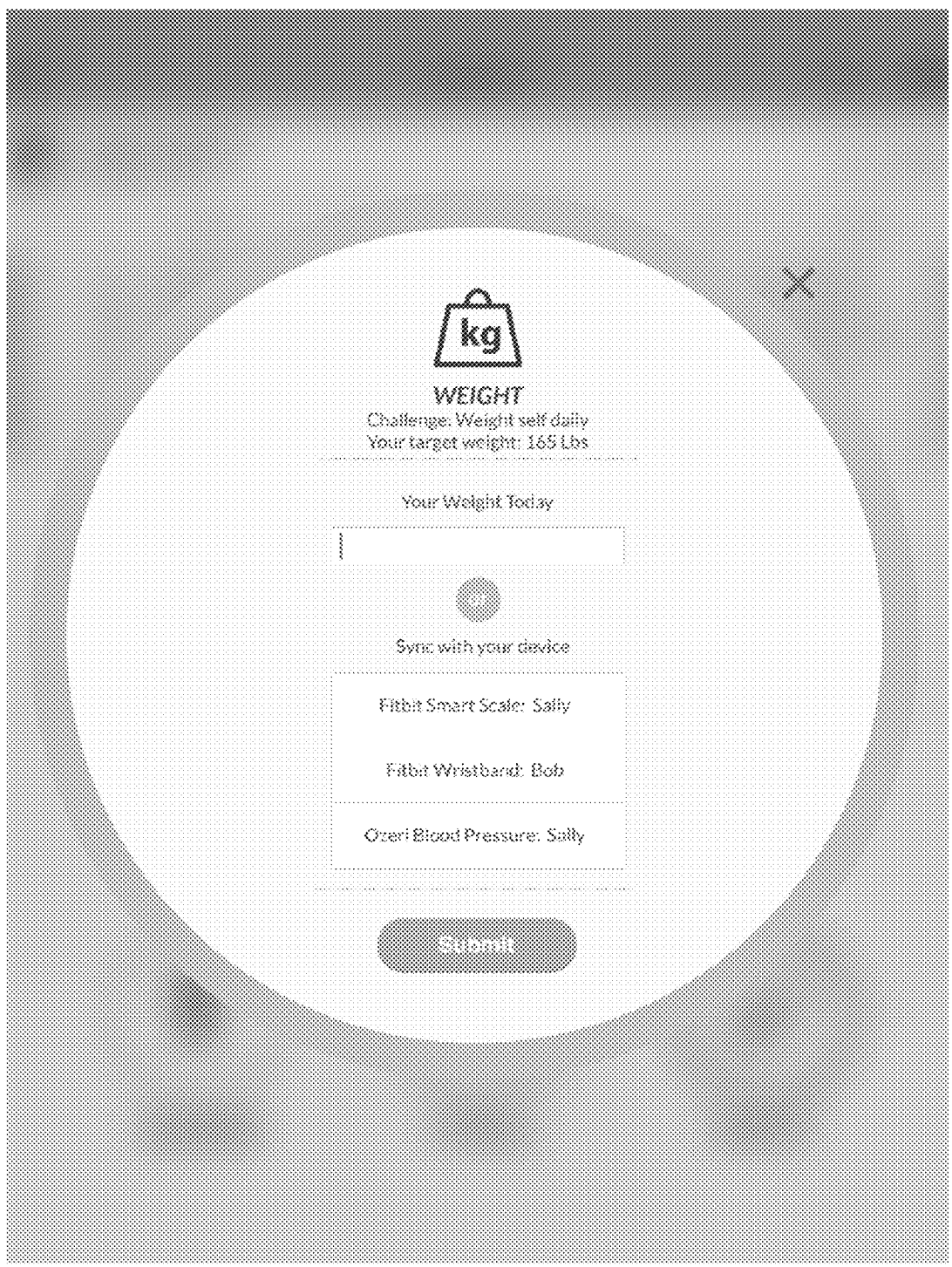

As shown in FIG. 16, application 100 can be further configured to smoothly communicate with a variety of health devices such as weight scale, heartbeat monitoring wristband, blood pressure monitor, and so on. The readings from such devices may be communicated to application 100 via a communication network 10 and recorded by application 100 as a completion of a Health Quest 26.

Figure 17:

As shown in FIG. 17, application 100 and/or platform 14 can be configured to distill the data collected by application 100 into simple reports, such as trending graphics, with action lines and automatically prompts to connect with Circle of Support member for medical advice or support when warranted, e.g., when a pre-defined event is detected (e.g., weight loss, increase in blood pressure, non-adherence to a medication regimen, etc.)

Application 100 may be configured to enable patients and their Circle of Support members to ask questions of each other, share information, feelings/emotions, secure feedback and journal about their daily tasks (e.g., Health Quests 26), both positive and negative (see FIG. 9*a*). The mechanisms enabling this communication can be for example:

Ask—Patients 18 as well as Circle of Support members can ask questions via chat (optionally using speech-to-text).

Share Information—Circle of Support members can post links, send text, chat (optionally using speech-to-text).

Motivational messaging—Circle of Support members can record or upload a media clip (e.g., a picture, audio clip, video clip, etc.) when they enroll. The media clip is kept hidden from the patient 18, but the patient 18 may gain access to the hidden media clip by completing Health Quests 26. Access to the media clip may be granted in parts such that the patient 18 gradually gains incremental access by completing Health Quests 26. Once a media clip is fully revealed, a notification may be sent to the Circle of Support member to provide a new media clip.

Feedback—Patients 18 can tap on various buttons that will enable them to express the following emotions.
Happy or Sad
Clear or Confused
Keep Going or Rest
Success or Failed (Struggle)
Better or Worse
Open feedback from both patients and Circle of Support Journal—Free-form journal for patients to record feelings, actions, accomplishments and/or struggles.

Gifts—Patients 18 as well as Circle of Support members may send gifts to one other (e.g., to express thanks or support). Such gifts may include virtual gifts (e.g., images of flowers, or media clips such as a song or video), monetary gifts (e.g., to a patient/Circle of Support member, or a donation to a charitable organization or a partnering organization in the name of a patient or Circle of Support member), or real gifts. Where the gift is a real gift (e.g., a real world object or service), an image of the gift may be presented through platform 14 to the recipient), and the real gift may be delivered to an address associated with the recipient by a partnering goods/services provider. Platform 14 may send an electronic notification to the recipient to notify them of the gift. In an embodiment, platform 14 may be configured to automatically transmit a gift to recipient (e.g., a patient) on pre-defined occasions, e.g., on a birthday, or on an enrolment anniversary.

Figure 18:
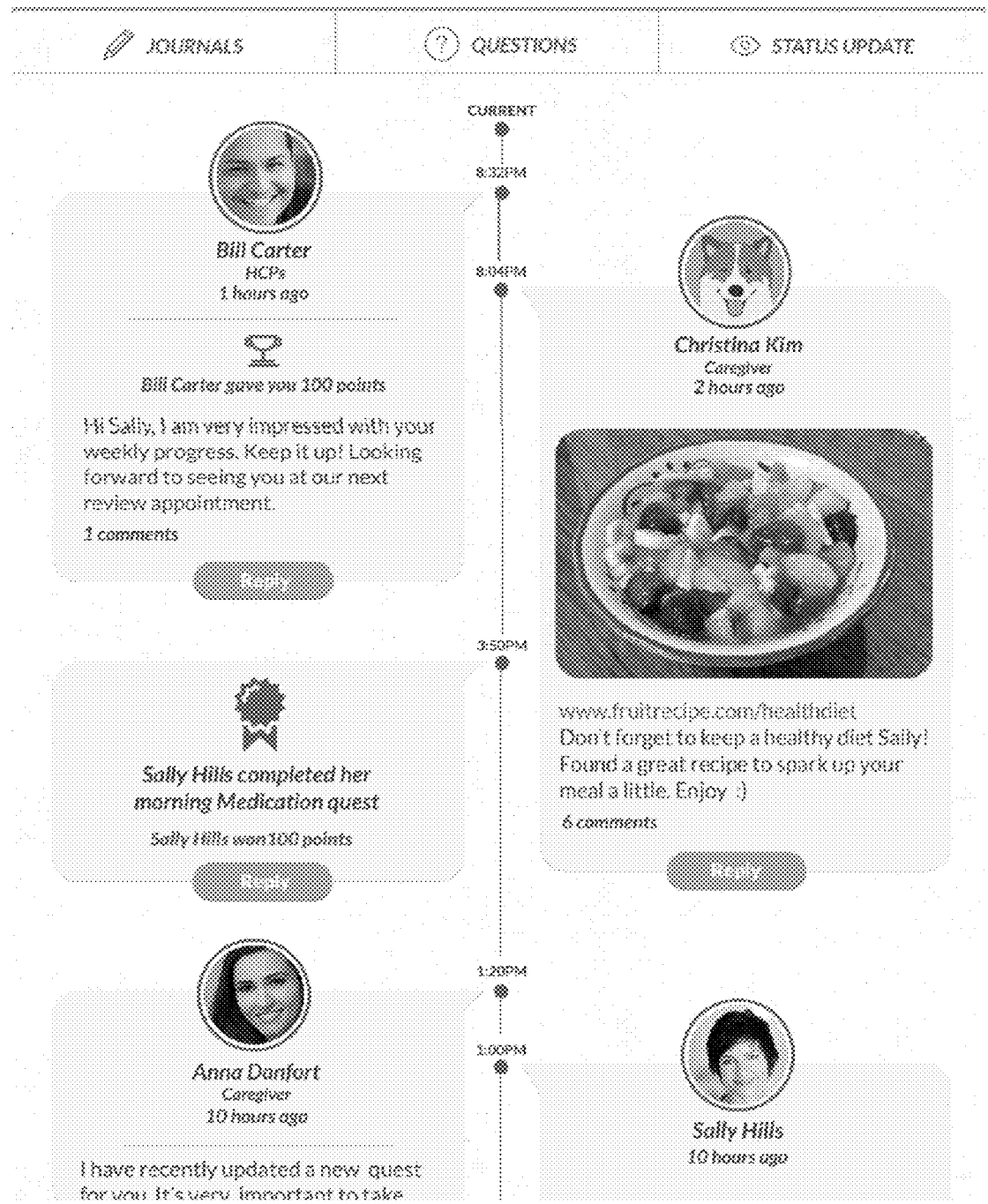

As shown in FIG. 18, a secure messaging platform may be provided by application 100 through which a patient 18 can stay connected to Circle of Support members. A patient 18 may choose to share success stories or ask questions to his or her supporters. A patient 18 may also receive feedback and support from Circle of Support members and stay encouraged and motivated in turn.

For example, a patient 18 may record their lunch for the day and show it to one or more Circle of Support members. A patient 18 can also choose to share conversations between one or more Circle of Support members with other members so that the support network is kept in loop with patient's progress. Advantageously, when a patient 18 knows he or she is being monitored, he or she may tend to adhere to the recovery regime better.

In addition, all the data entries, including completed or missed Health Quests 26 and conversations between Circle of Support members and patient 18 can be automatically tracked and later analyzed, e.g., in order to generate insights relating to patient health and/or produce patient reports such as patient journey report for a patient 18. The reports may show progress of the patient in an intuitive and easy-to-follow manner. The reports may be shared among Circle of Support members so that they may follow patient's progress in real-time efficiently.

Figure 19A:
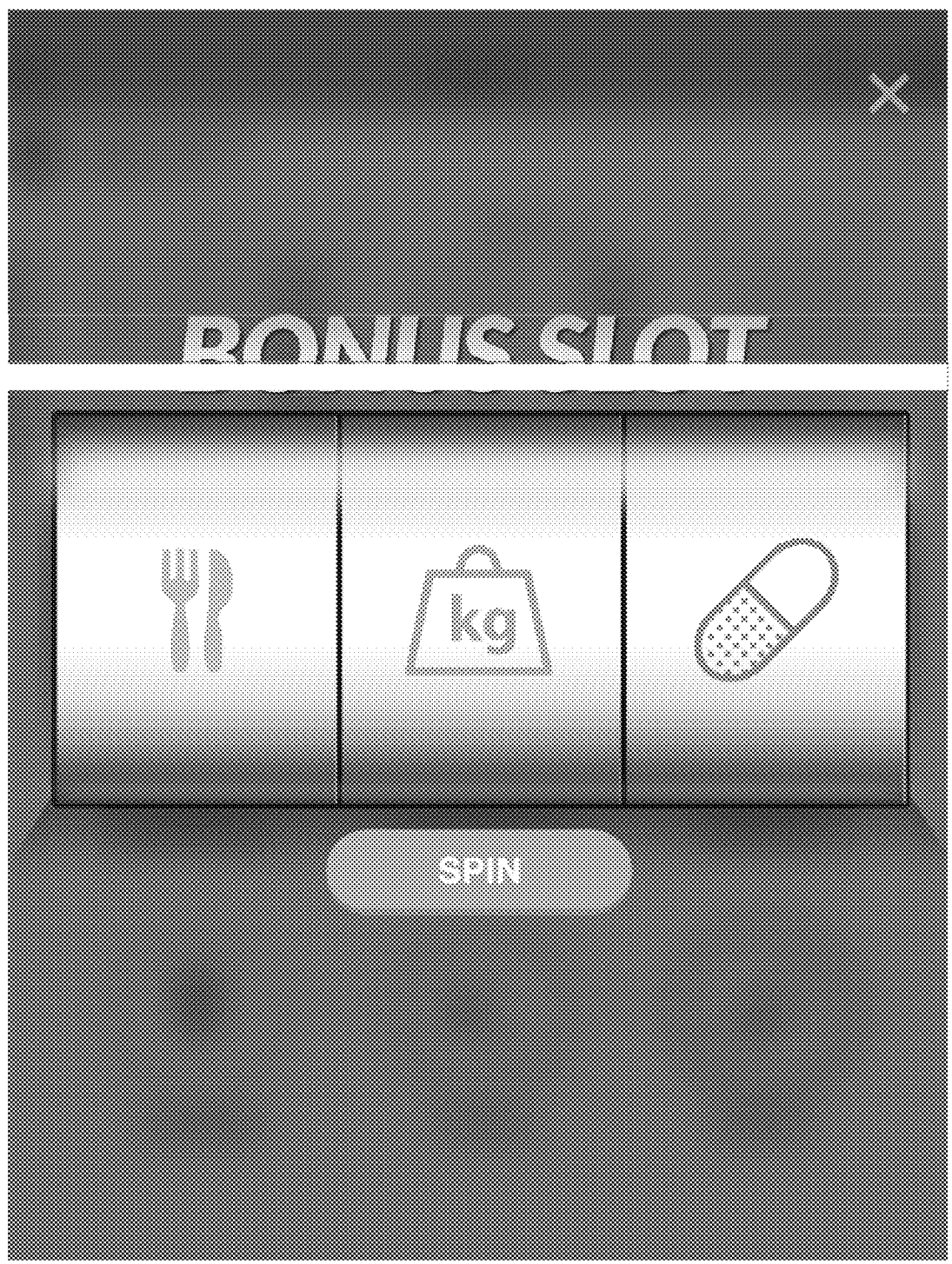
Figure 19B:
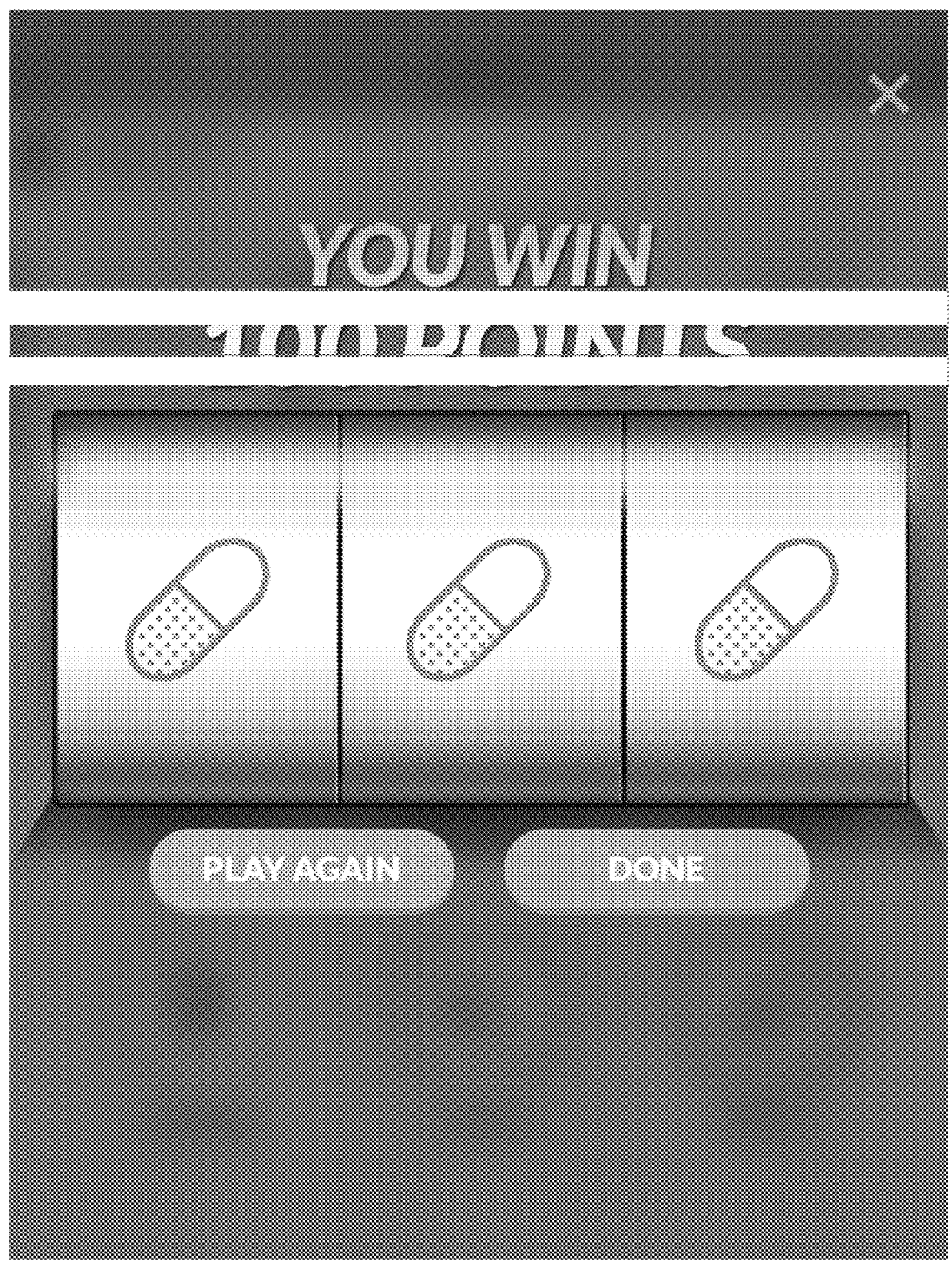

In an embodiment, a workflow of application 100 (optionally, in combination with platform 14) may include support and encouragement for successful completion of tasks (i.e., Health Quests 26). Patients 18 can be awarded different amounts of points for achieving different levels of completion. These points can be redeemed for tangible health-related rewards. In addition, points can be earned through a virtual slot machine (e.g. as shown in FIGS. 9*b*, 19*a* and 19*b*), which provides a dimension of fun, thereby encouraging patients to sustain their interest and motivation to complete their assigned tasks. On top of the points-based reward system, Circle of Support members can give recognition through plaques, which are featured on the patient's historical visualization trend.

In another embodiment, a patient 18 can be rewarded with points both for completing a Health Quest 26 and for positive feedback from the Circle of Support. Points can be gambled (and/or multiplied) on an in-app virtual slot machine (see e.g. FIGS. 9*b*, 19*a* and 19*b*), providing an addictive element of fun. As an option, points may be further redeemed for real-world health-related rewards.

Figure 20A:
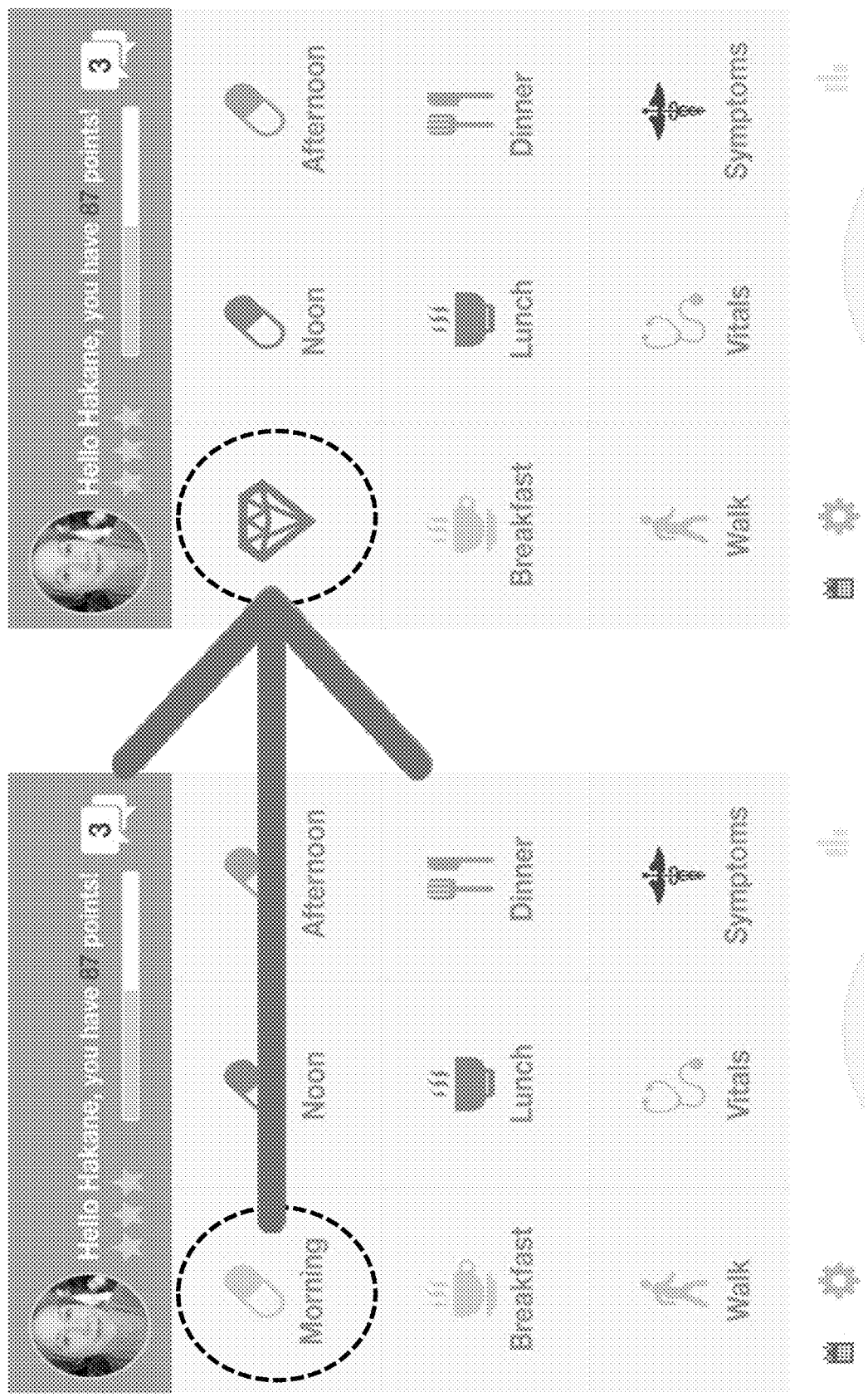
Figure 20B:
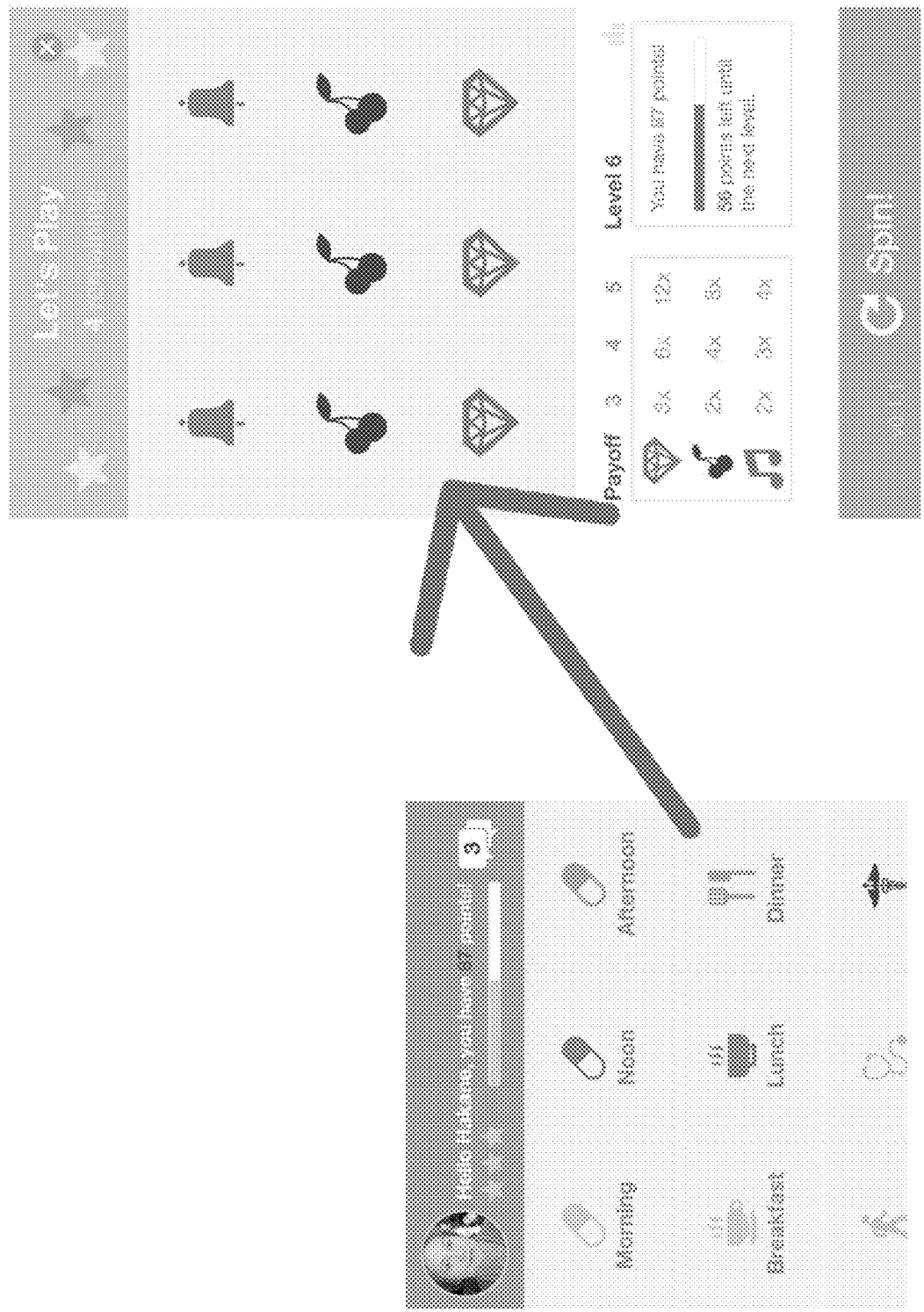

For example, as shown in FIG. 20*a*, upon completion of a Health Quest, a game play icon is revealed. Once all game play icons are revealed, the patient can play the slot machine game (see e.g. FIG. 20*b*).

Such intrinsic rewards are often regarded as more powerful than extrinsic rewards.

In an embodiment, platform 14 may be configured to monitor a patient's engagement to assess and gauge usage patterns. Platform 14 may transmit an electronic notification to the patient if engagement falls below normal usage patterns, or if the patient ceases to interact with platform 14 or application 100 for a pre-defined period of time (e.g., 2 days, a week, etc.). This threshold may be calibrated based on the patient's typical usage patterns (e.g., usage frequency) as monitored.

A Health Quest 26, although tuned to the individual patient 18, may be useful and meaningful to other patients under similar conditions or sharing other characteristics. Quest Sharing allows patients to post messages regarding their Health Quests through platform 14. In an embodiment, platform 14 may automatically identify other patients 18 having similar conditions or other characteristics, and direct the posted messages to such identified patients. Platform 14 may be configured to enable patients and other members to rank and comment on their experience in relation to particular widgets or particular Health Quests 26.

Application 100 and platform 14 can provide a source of assurance, an early warning safety net, and a source of insights for the patient, care giver and care team into patient behavior and how it affects their outcomes.

In another embodiment, application 100 can also be configured to send patient 18 surveys or daily questionnaires regarding how he or she is managing the illness or condition. Questionnaires can be designed based on principles of health psychology and other factors.

As an incentive to participate in the surveys or questionnaires, patients may be rewarded with points or compensation upon completion of a survey or questionnaire.

Figure 23A:
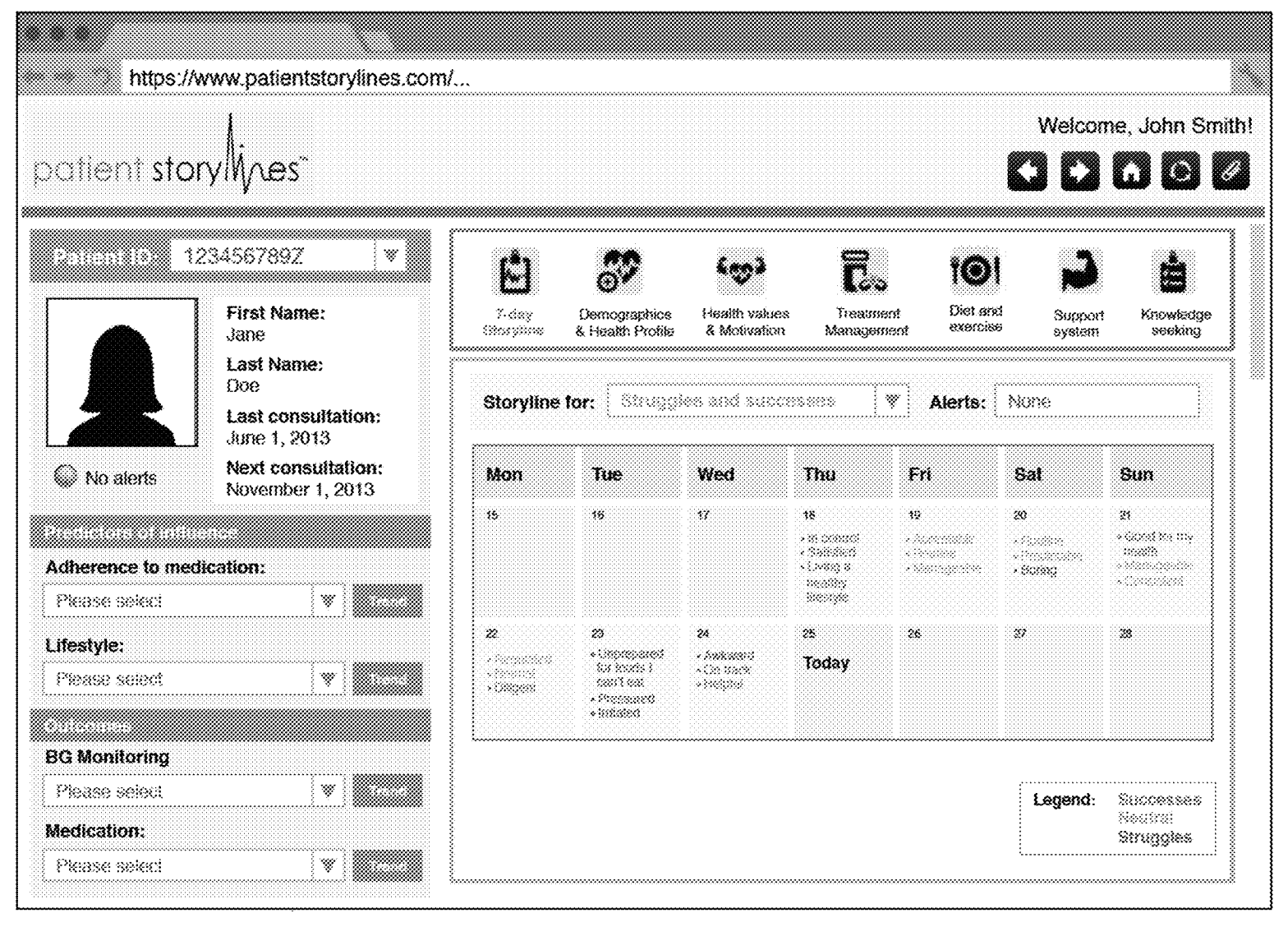
Figure 23B:
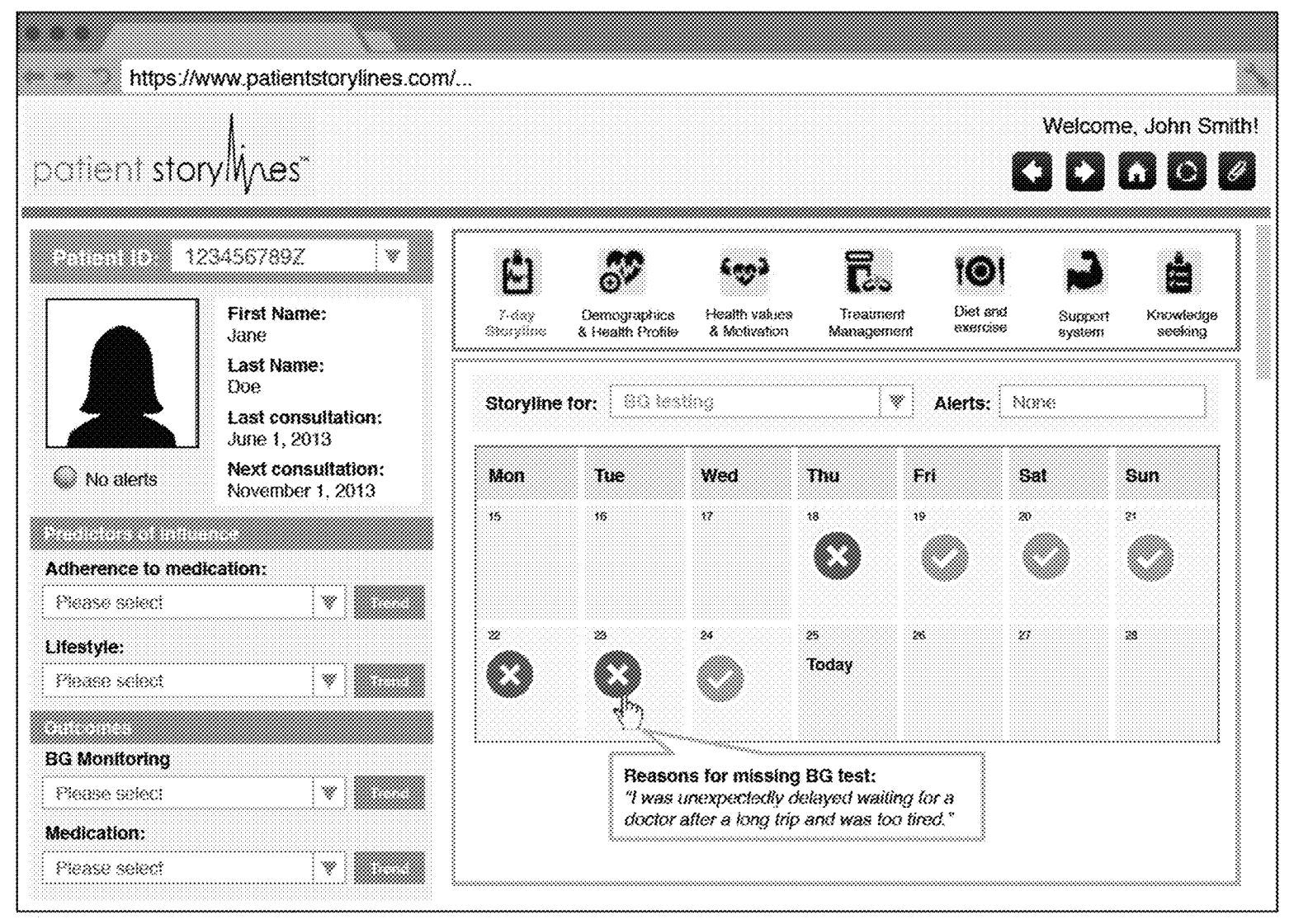
Figure 23C:
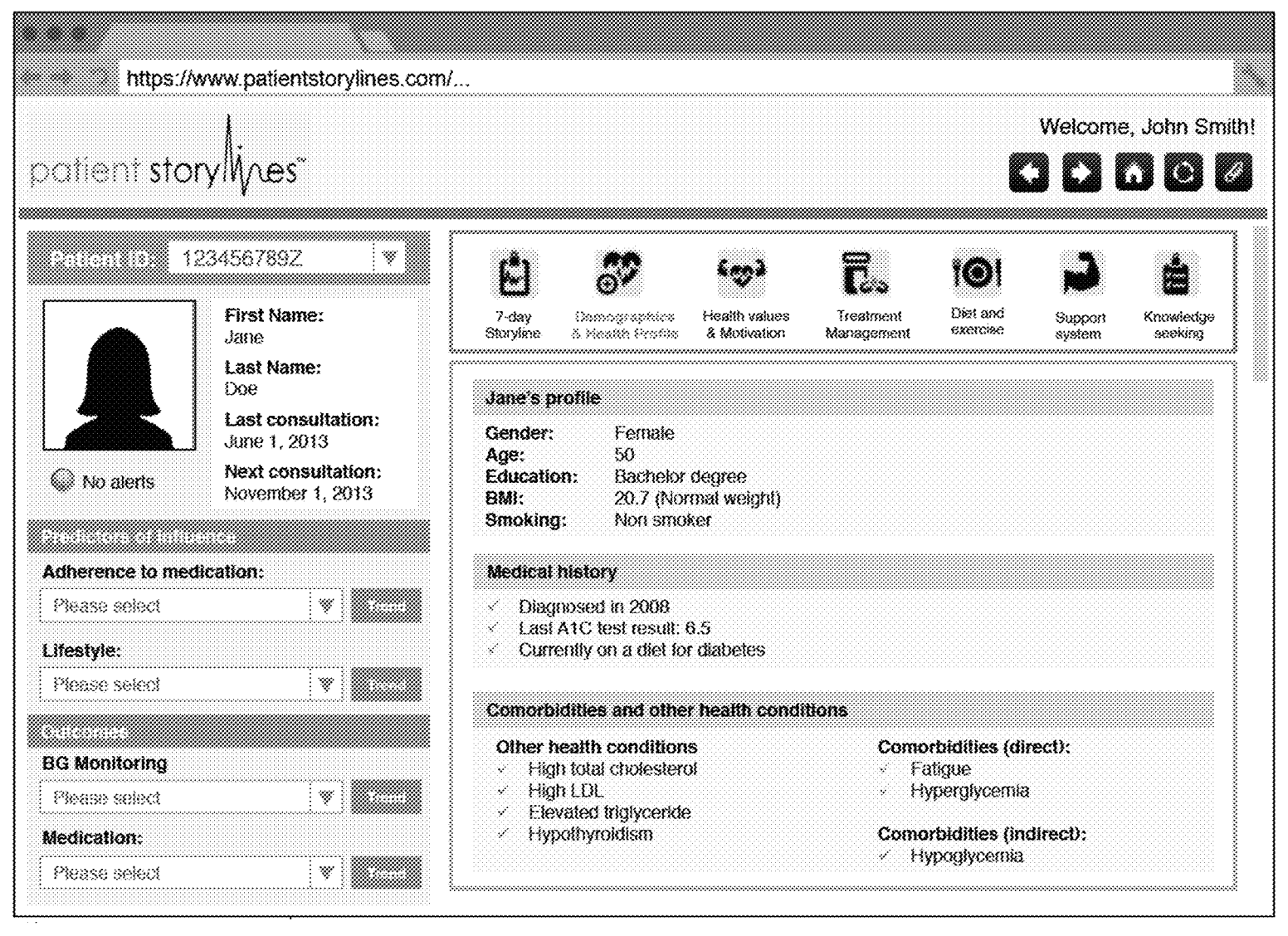
Figure 23D:
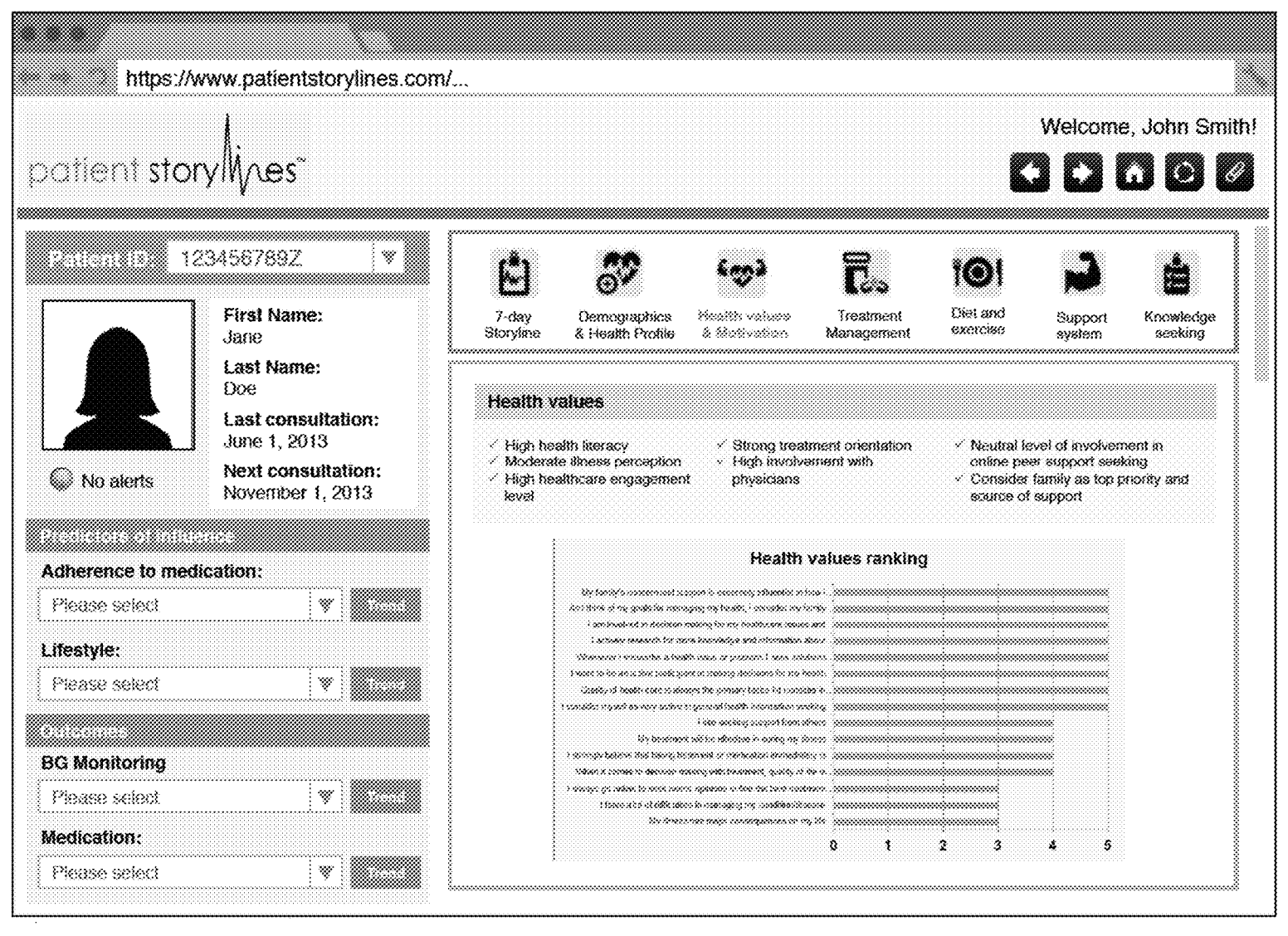
Figure 23E:
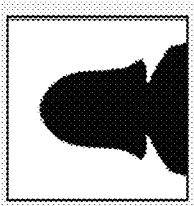
Figure 23F:
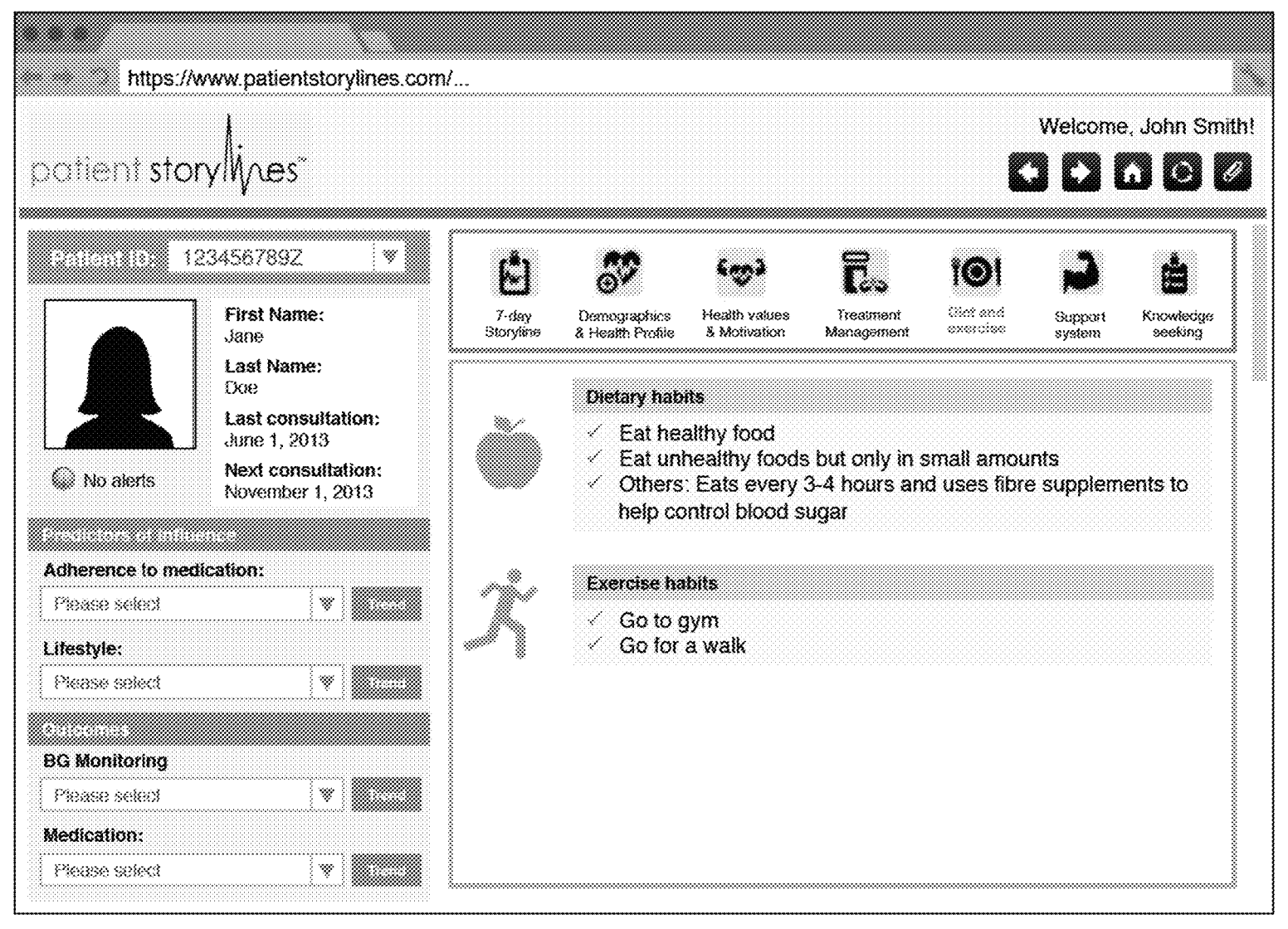
Figure 24A:
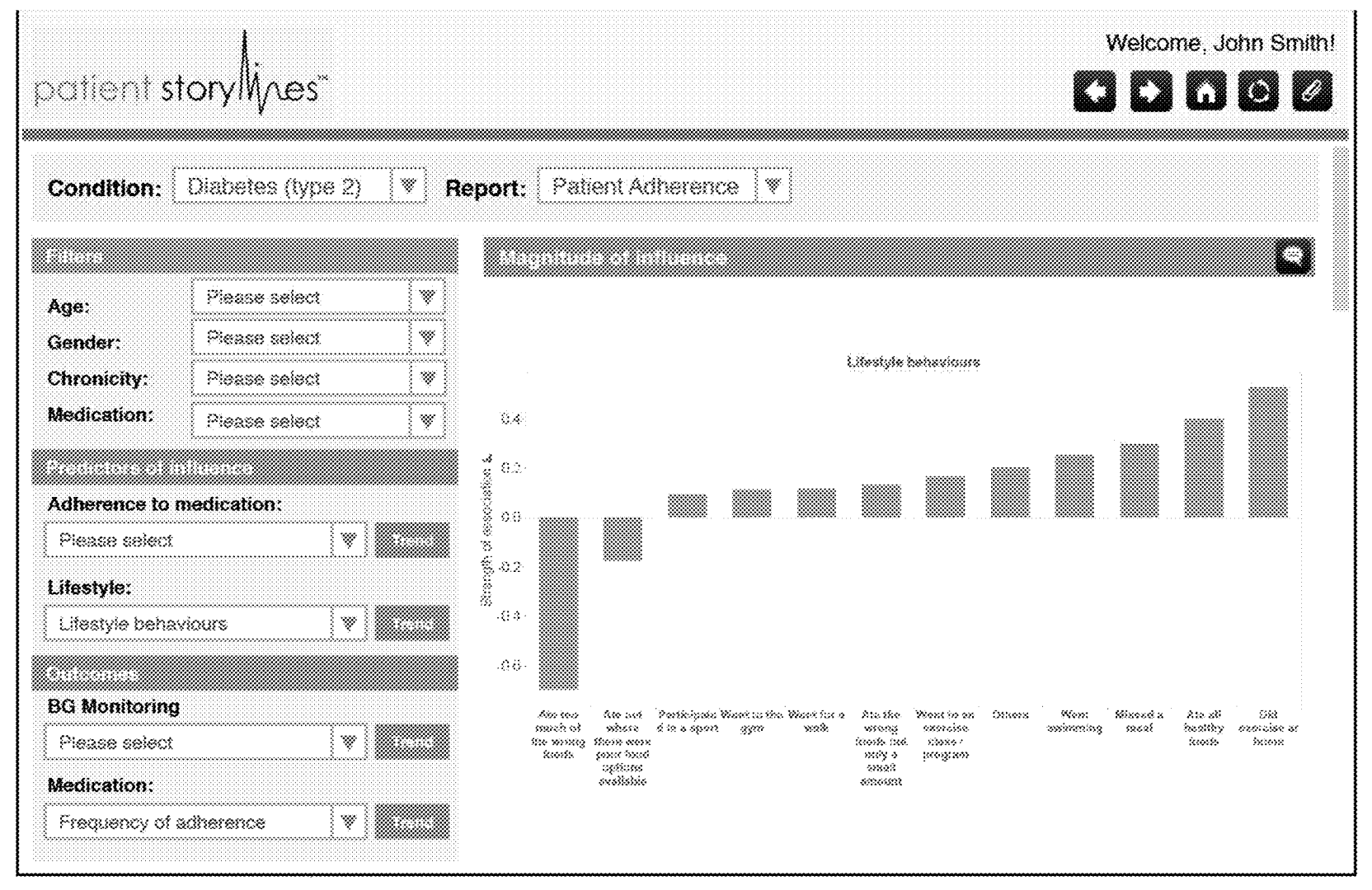
Figure 24B:
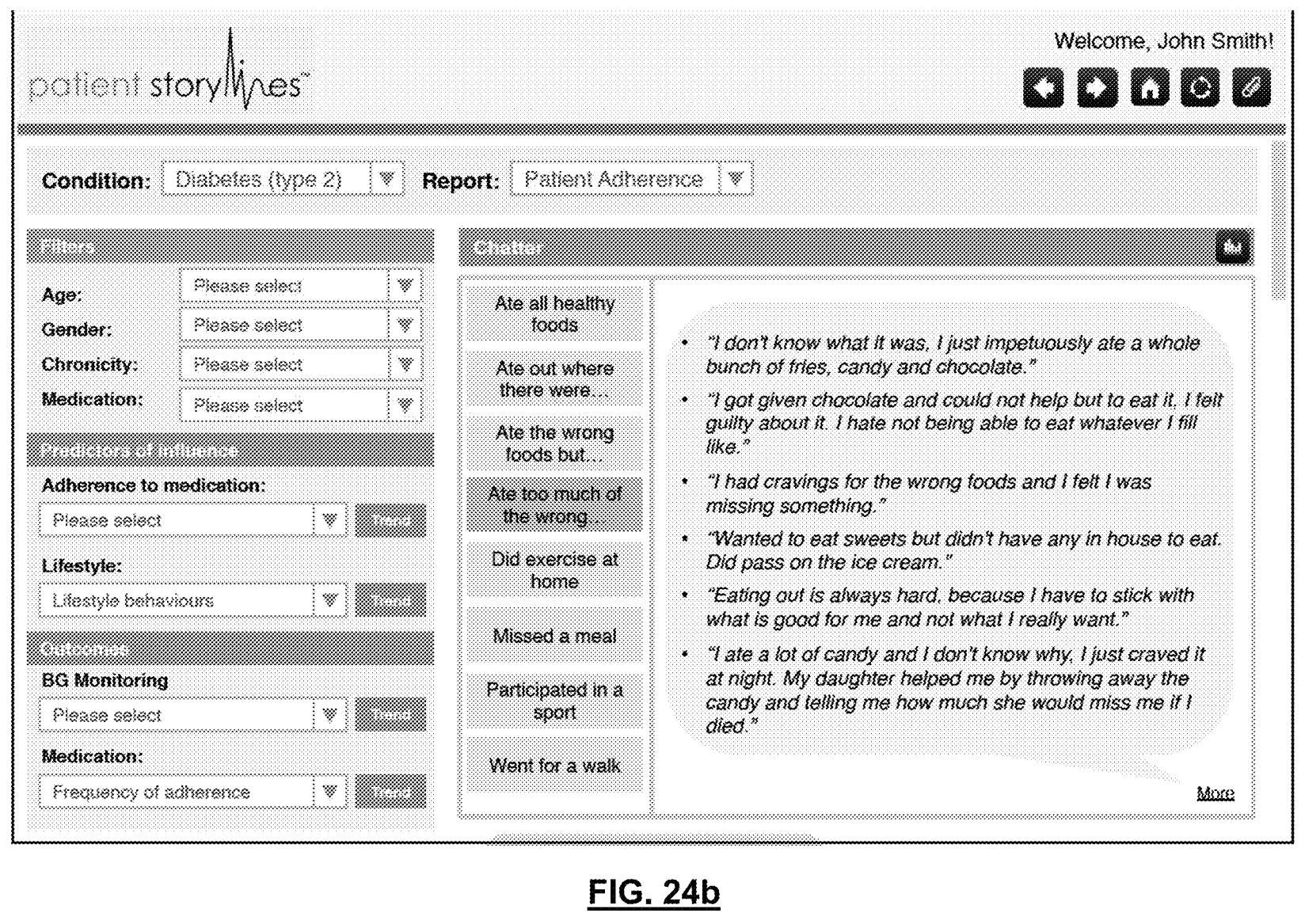
Figure 24C:
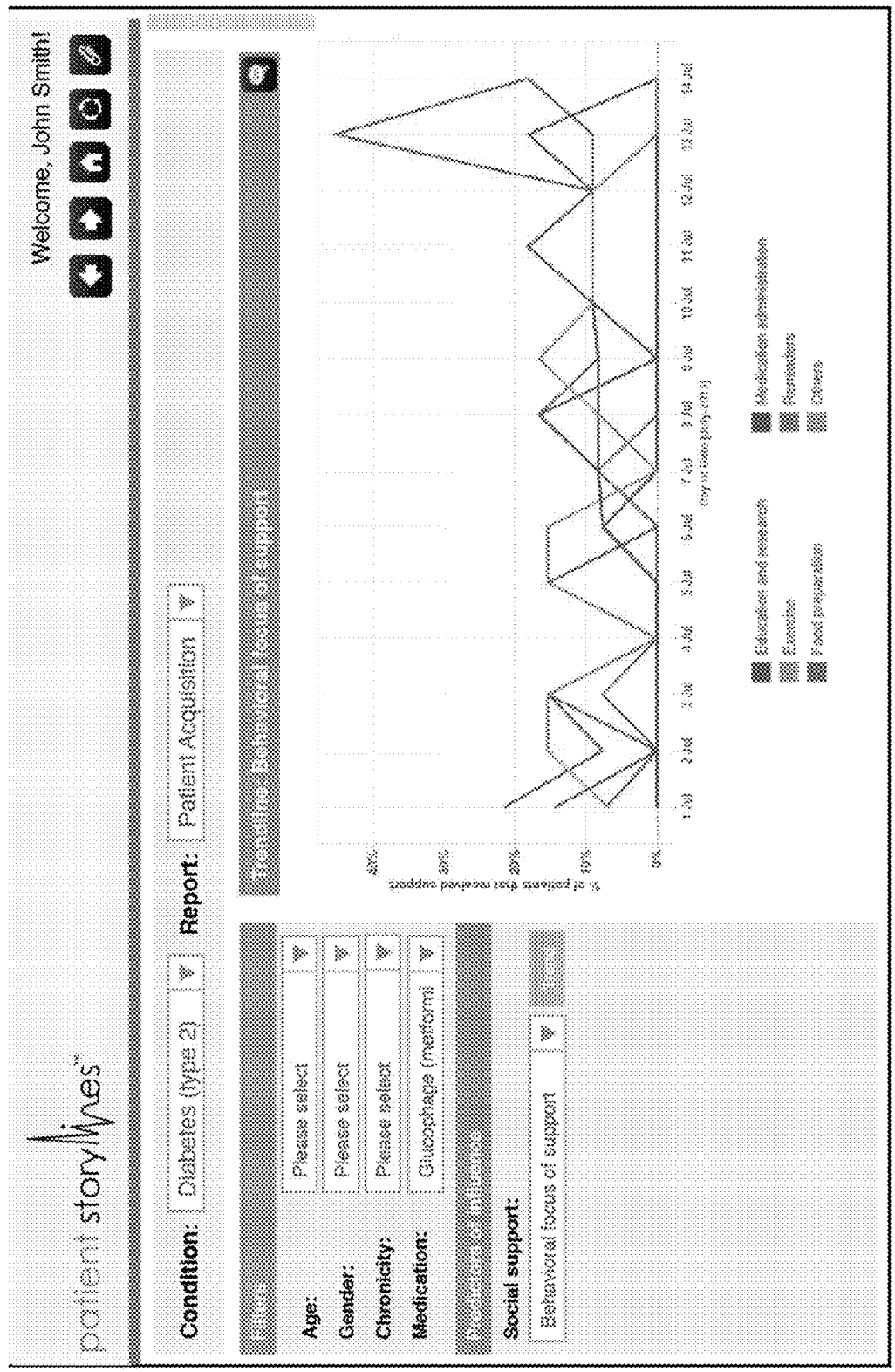
Figure 24D:
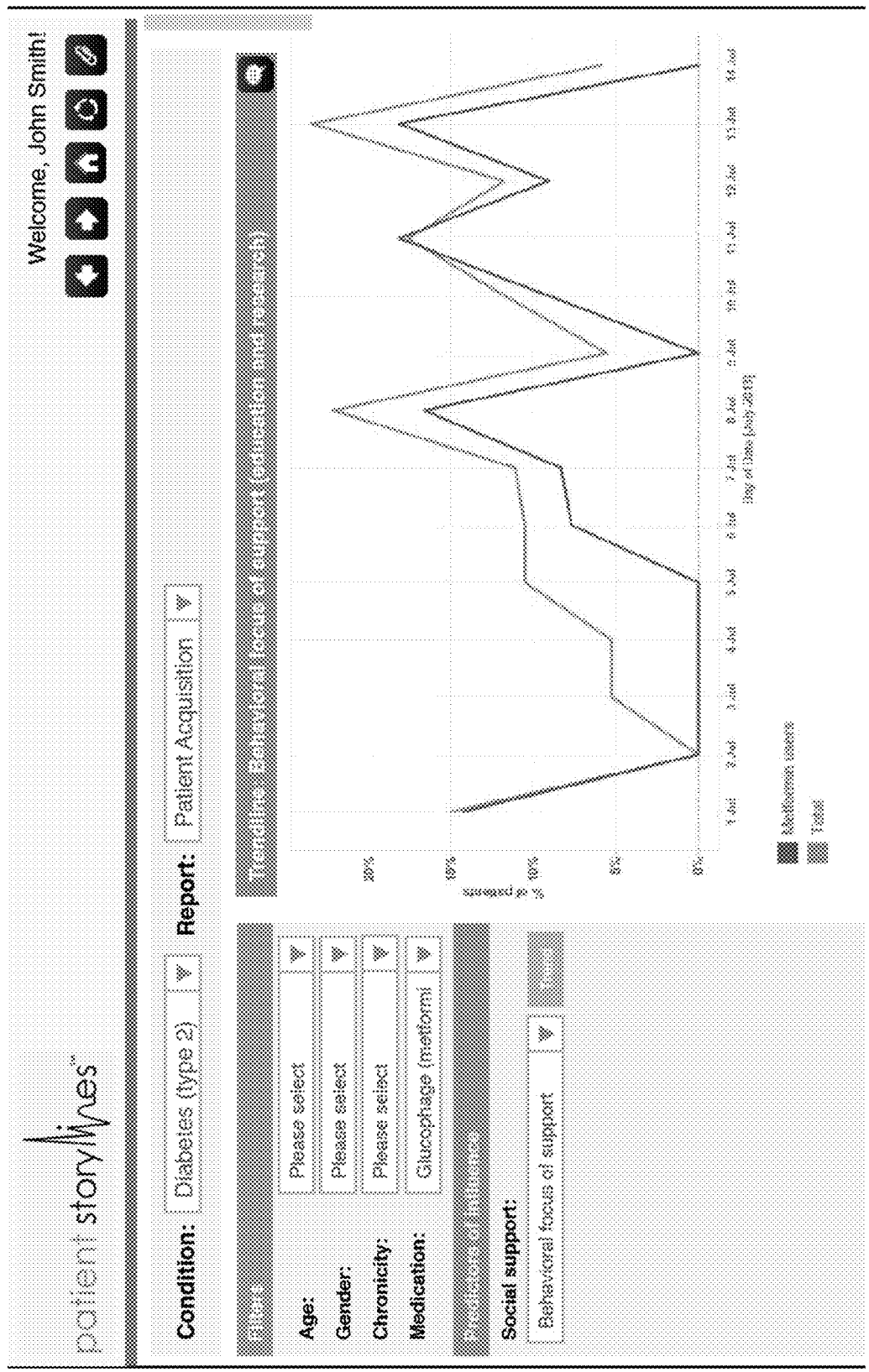

Application 100 can be further configured to send patients' responses and results to platform 14, which can in turn analyze aggregated patient responses and prepare actionable client output or patient reports (see e.g. FIGS. 23 and 24).

Exemplary Workflows

Exemplary workflows of application 100, in accordance with one or more embodiments, are presented below:

1. Social Engagement, Encouragement, Accountability and Feedback
    a. Part 1. Quest creation:
        i. Can be custom created by the patient, a Circle of Support member, or chosen from a list of available content
        ii. Step 1: Goal setting.
            1. E.g. for a "vital quest" for a patient where water retention is a worrisome sign, goal may be to maintain current weight.
        iii. Step 2: Task setting. What specifically will be done each day as part of the daily quest.
            1. E.g. take photo of scale each day.
        iv. Step 3: Publishing quest. Quest is sent to patient and ally list and posted to the quest grid board (see e.g. FIG. 7)
    b. Part 2. Populating the quest grid:
        i. Step 1. Weekly quest selection
            1. At the beginning of the week patients selects up to 9 quests or quest bundles to populate the 3×3 quest grid.
                a. Quests can still be dynamic from day to day, though the category may be fixed for the week
                b. E.g. a Circle of Support member quest can have a different set task generated each day for the patient, though the name/category on the grid may remain fixed
    c. Part 3. Selecting and completing a quest
        i. Step 1. Patients can choose a quest directly from the quest grid
        ii. Step 2. Patients follow the assigned steps and submit.
        iii. Step 3. Coins rewarded and points assigned to badge/trophy/ranking
            1. Amount of coins rewarded will increase as rank increases.
        iv. Step 4. Quest is sent to assigned ally for scoring.
        v. Step 5. Graphics on quest grid updated
    d. Part 4. Circle of Support member in receipt of quest and quest scoring.
        i. Step 1. Circle of Support members log into their web or mobile interface of application 100 and are presented with a list of patients with active quests awaiting scoring, active quests with worrisome values, or quests that have been dormant 2 or more days. Circle of Support members can see a patient's completed quest list as either a task list or a reflection of the patient's quest grid.
        ii. Step 2. Circle of Support members score quest good, great, or needs work with the option to add a brief message.
        iii. Step 3. Coins rewarded to ally and patient.
    e. Part 5. Quest updated on patient's grid with new graphic, additional coins reward to patient
    f. Part 6. Selecting a completed quest from the quest grid brings up the data visualization card
        i. Displays trend lines or report for that quest.
2. Games
    a. Coins can be used to play the built-in slots game
3. Gamification
    a. Completion of health quests rewards points towards badges, trophies, plaques, and rankings.
    b. Higher rankings increase coins rewarded from quests
4. Real World Incentives
    a. Coins can be redeemed for real world health related rewards
5. Education
    a. Quests can provide educational informational around medications, disease, health, and well-being.
6. Tracking
    a. Quests can interface directly with compatible devices or access app or device repository data accessible through the service API to automatically pull relevant data.
    b. Passive activity data can be collected through a combination of M7 motion sensors, gyroscope, ambient light sensors, and other equipment specific sensors. FIG. 25 demonstrates how sample data may be collected via various channels available to Application 100.
    c. Positive and negative scoring of photo based quests
    d. Emotional framing (positive, neutral, negative) of text based quests and messages through natural language processing.
7. EMR Interface
    a. Blue button compliant electronic medical records can be parsed and relevant data pulled into the application 100 or platform 14 through a request button within the application 100.
8. Reminders
    a. Tasks and medication adherence reminders can be sent through push notifications or SMS text.
9. Data Visualization a. Data condensed for easy interpretability with action ques.
10. Behavioral analytics and signal detection
   a. Data analyzed in real time for potential actionable events such as a physical fall, or symptoms crossing a threshold warranting follow-up with a medical professional
   b. Risk management of patients by likelihood of hospital readmission or adverse event
   c. Analysis of behavior change opportunities that would lead to higher likelihood of positive outcomes.

Figure 3:
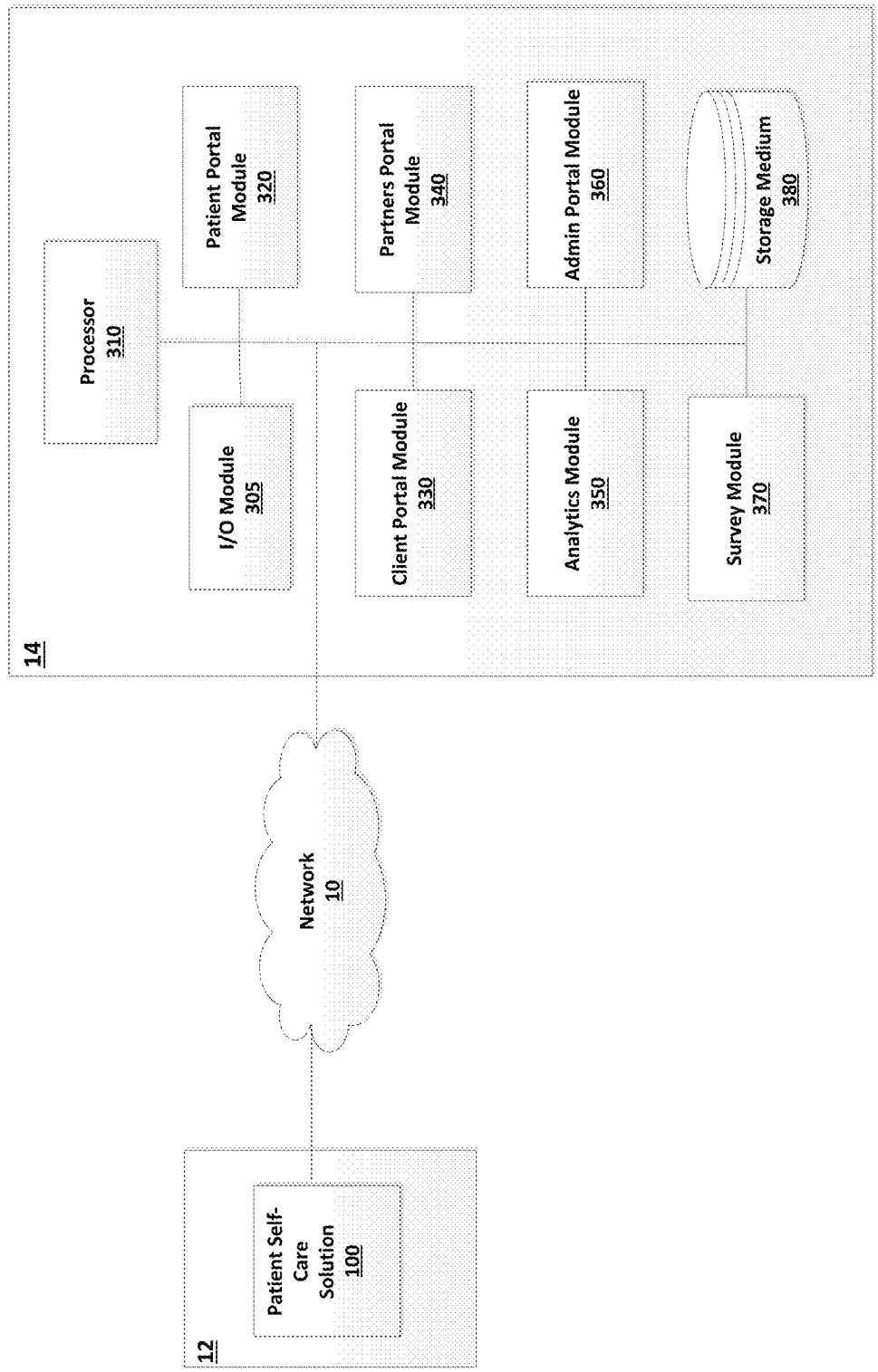
FIG. 3 is a high-level schematic diagram of a system of FIG. 1 or FIG. 2, in accordance with an embodiment.

As shown in FIG. 3, in an embodiment of the invention, platform 14 may include various modules including processor 310, I/O module 305, patient portal module 320, client portal module 330, partners portal module 340, analytics module 350, admin portal module 360, survey module 370, and a storage medium 380.

Platform 14 may be connected to application 100 on a mobile device 12. Platform 14 may also be connected to client portal interfaces hosted on computer device 24 (shown in FIG. 2) and to Circle of Support interfaces hosted on devices 16a-16d. The portals may be accessed on any computer device, including in HTML5 format and in a mobile-friendly way.

Figure 21:
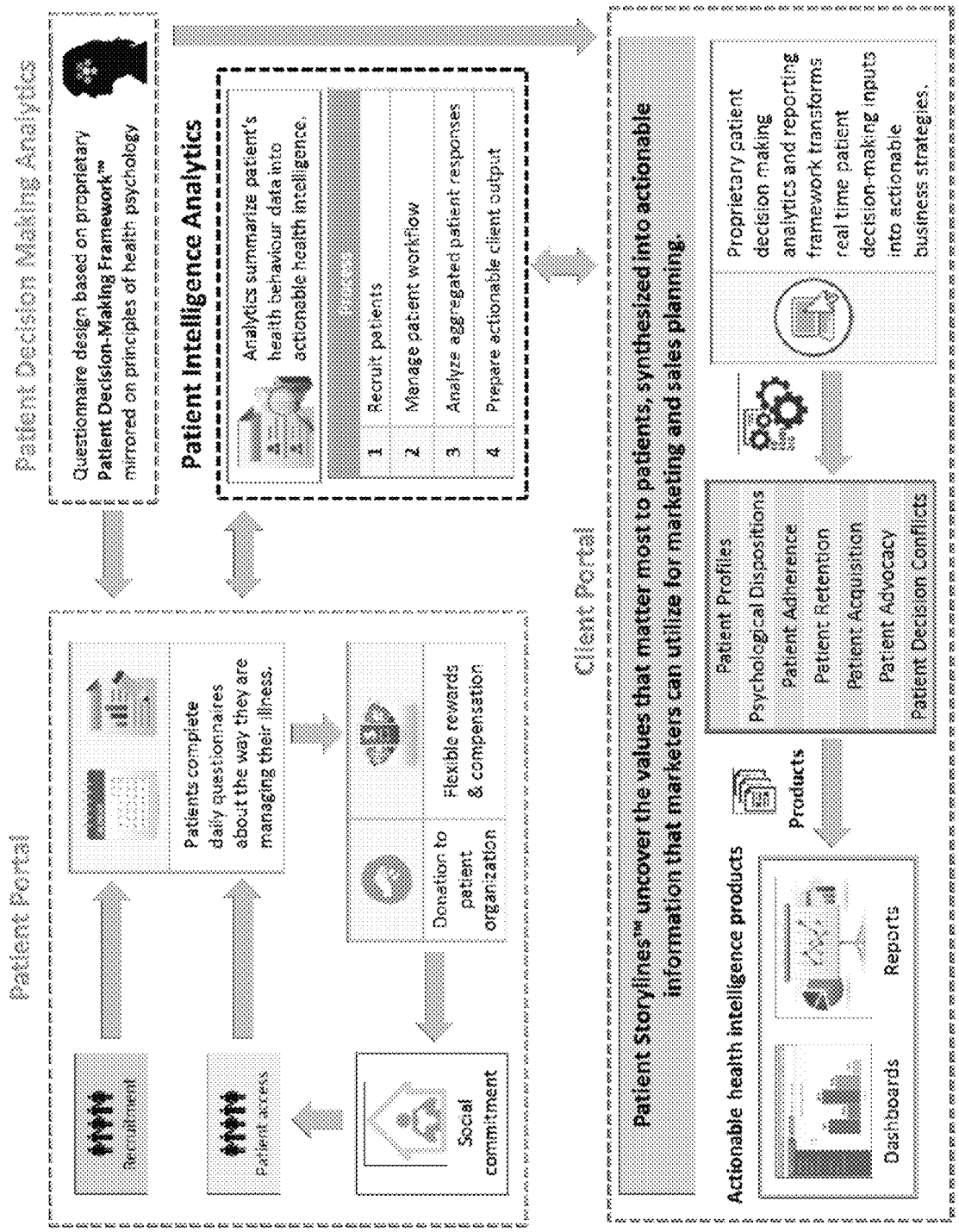
FIG. 21 illustrates an exemplary configuration of the system of FIG. 3, in accordance with an embodiment.

Platform 14 can present real-time, real-world, procedurally-generated ad hoc patient and Circle of Support surveys that can feed into customized research activities such as clinical studies, patient outcomes research, and intervention tests, as shown in FIG. 21. The Patient Intelligence Analytics component as shown in FIG. 21 may be implemented as part of analytics module 350, discussed below. The Patient Intelligence Analytics component may be configured to summarize patient's health behavior data into actionable health intelligence. An exemplary process of Patient Intelligence Analytics component can be: 1. recruit patients; 2. manage patient workflow; 3. analyze aggregated patient responses; and 4. prepare actionable client output.

The client output may then be synthesized into actionable information that marketers can utilize for marketing and sales planning. Patient portal 320 may facilitate the invitation and recruitment of patients 18 for the purpose of answering surveys or daily questionnaires. For example, patient portal 320 may receive inputs from patients 18 and create a corresponding patient profile and store the patient profile in database 380.

Figure 26:
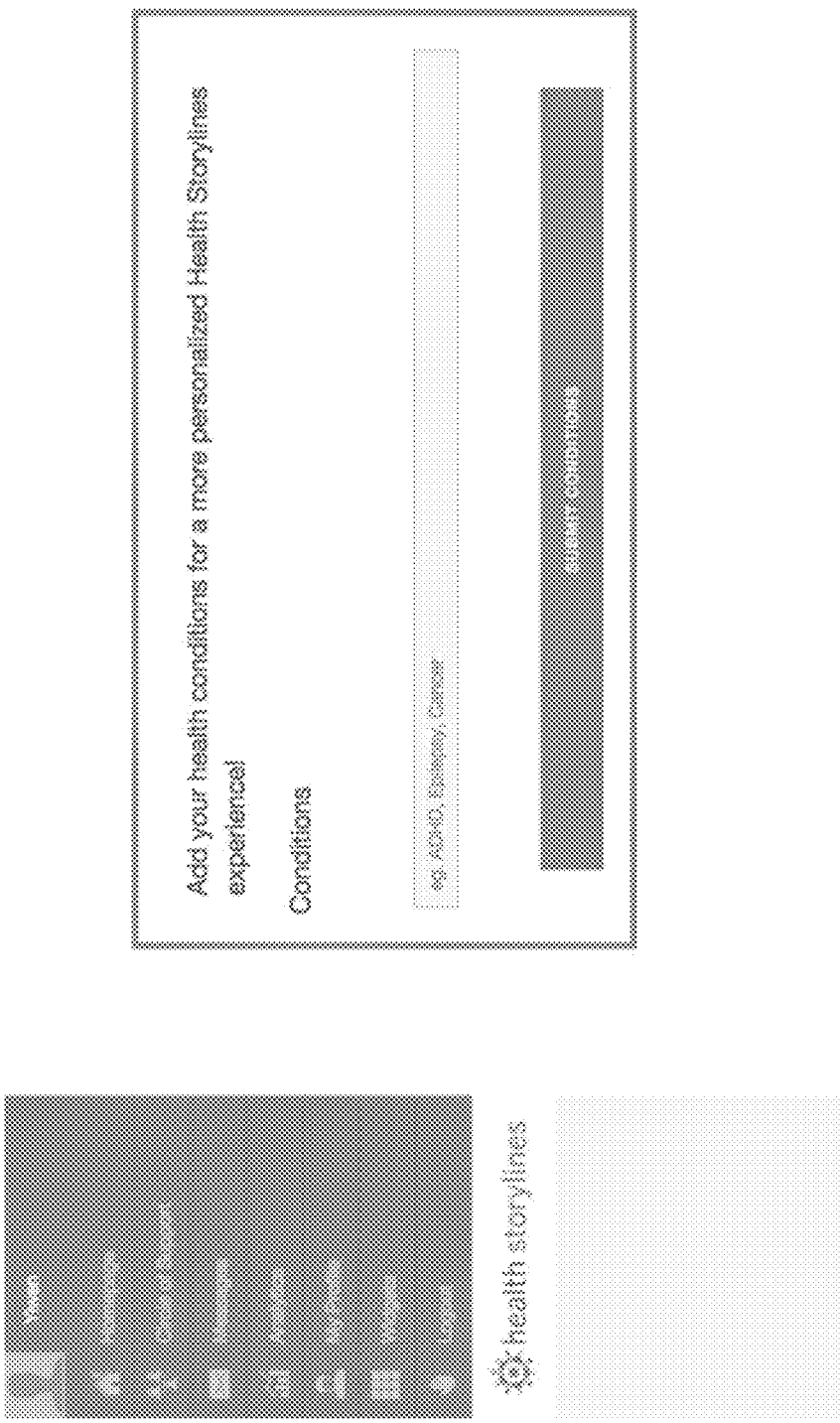
FIG. 26 illustrates an example user interface for enrolling a patient, in accordance with an embodiment.

FIG. 26 depicts an example interface presented to a patient as a part of an enrolment process. As shown, this interface may prompt the patient to enter various characteristics, e.g., one or more health conditions. This interface may also prompt the patient to other characteristics including, e.g., age, gender, primary health concerns, comorbidities, etc. Such characteristics are stored by platform 14 as part of a patient profile of the patient 18. Such characteristics may, for example, be used to match patients to particular widgets (Health Quests 26), to particular Circle of Support members, to particular other patients, etc.

Patient portal 320 may also offer extra features such as journal keeping, statistics based on patient history, statistics based on disease history without protected or other personal data shown across patients, and/or access to chat rooms.

Patient portal 320 may be configured to allow patient to manage his/her Circle of Support, e.g., by adding or removing users. Patient portal 320 may provide an interface configured to allow a patient to search for individuals to add to his/her Circle of Support, e.g., by using a name, e-mail address, or other suitable identifiers.

In an embodiment, patient portal 320 may automatically recommend individuals for users to add to his/her Circle of Support, e.g., based on generated patient insights. In one example, patient portal 320 may recommend individuals having similar symptoms or having the same medical condition. Patient portal 320 may suggest or filter recommendations based on demographic characteristics of patients (e.g., gender, age, etc.) or based on geographical proximity. In this way, patient portal 320 assists patients in building a Circle of Support comprising a group of patient peers who may assist in providing the care and support, or participate in an exchange of information relevant to the peer group. For example, peers may provide peer-to-peer mentoring, through sharing of learning objectives, sharing of learned behaviours (e.g., coping skills). Patients may also seek and receive advice relating to healthcare decisions from others in the group of patient peers.

Conveniently, patient portal 320 may help a patient expands his/her Circle of Support to extend beyond individuals known to the patient. This may ameliorate effects of isolation, and to promote a feeling of belongingness.

Patient portal 320 may provide an interface configured to allow a patient to define a relationship type for each member of his/her Circle of Support, and to set access levels for his/her data/insights according to relationship types. In this way, a patient may control dissemination of information (e.g., collected data and/or generated insights) within his/her Circle of Support.

Client portal 330 is configured to provide clients (e.g., pharmaceutical or clinical clients) access to a client dashboard for a variety of functionalities including:
1. Access collected data;
2. Export collected data to client-readable format (i.e. CSV)
3. Access reports generated; and/or
4. Ability to access statistical analysis data Partners portal module 340 is configured to provide dashboards for various users including Circle of Support members. For example, partners portal module 340 may allow such users to view collected data (e.g., entered by patients or by one or more widgets) and to view the analytics results (e.g., generated insights) provided by analytics module 350.

Figure 35:
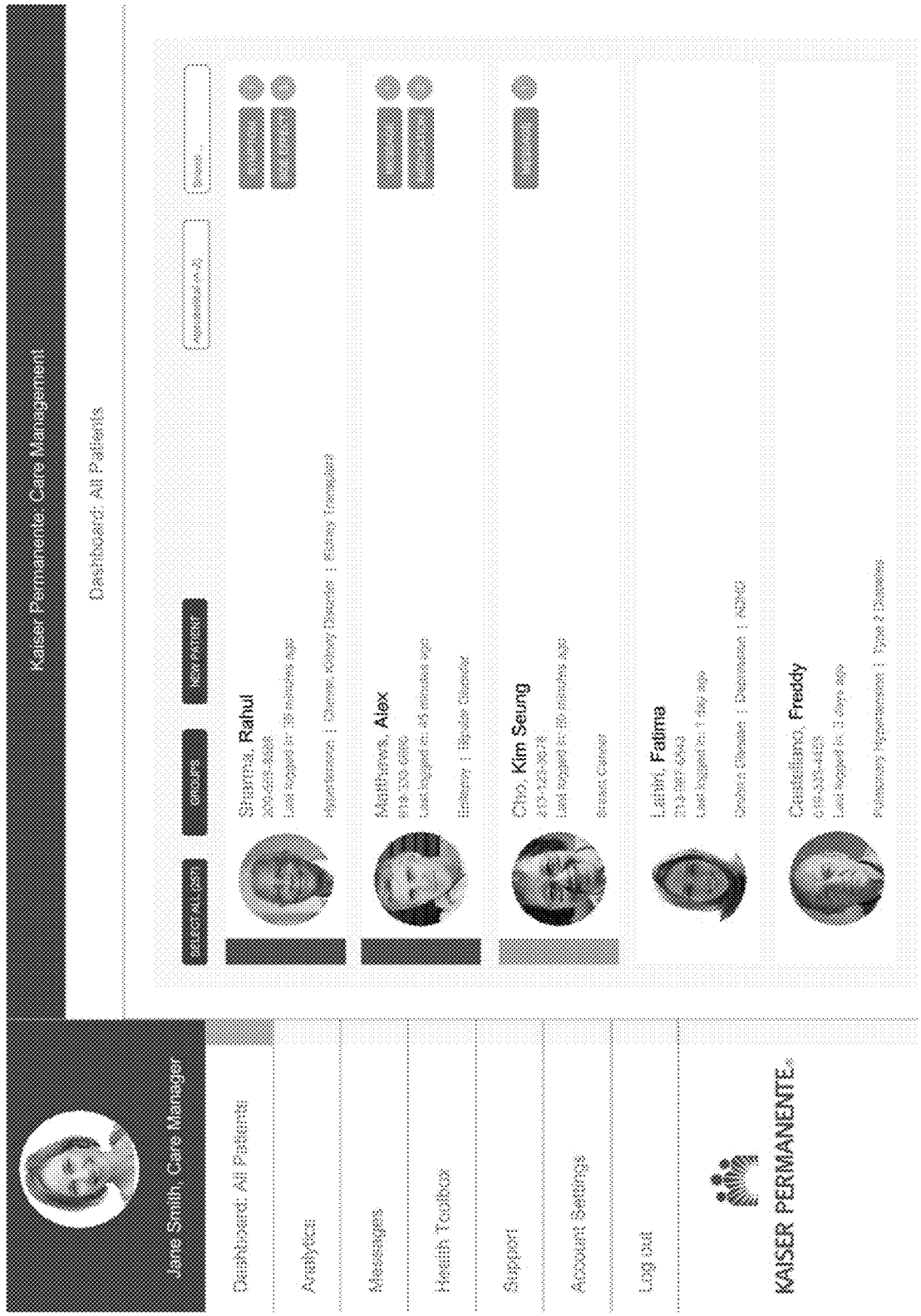

In an embodiment, partners portal module 340 may be configured to provide users designated as case managers with access to data and/or generated insights. In this embodiment, partners portal module 340 may be configured to present an interface allowing a case manager to add/remove patients 18 for which they have responsibility. As shown in FIG. 35, partners portal module 340 may also present a case manager with a listing of their associated patients in conjunction with status information. In this list, patients 18 may be ordered based on the urgency by which they require attention from a case manager. This urgency may be generated as an insight by analytics module 350 based on collected data. As shown, the urgency may be color-coded in the list of patients (e.g., with red designating very urgent, and orange designating somewhat urgent). The list may also include a reason for why attention from the case manager is needed, e.g., that the patient is not taking their medication, or that the patient has reported low moods over a period of time, that the patient has reported a symptom or side effect.

Figure 36:
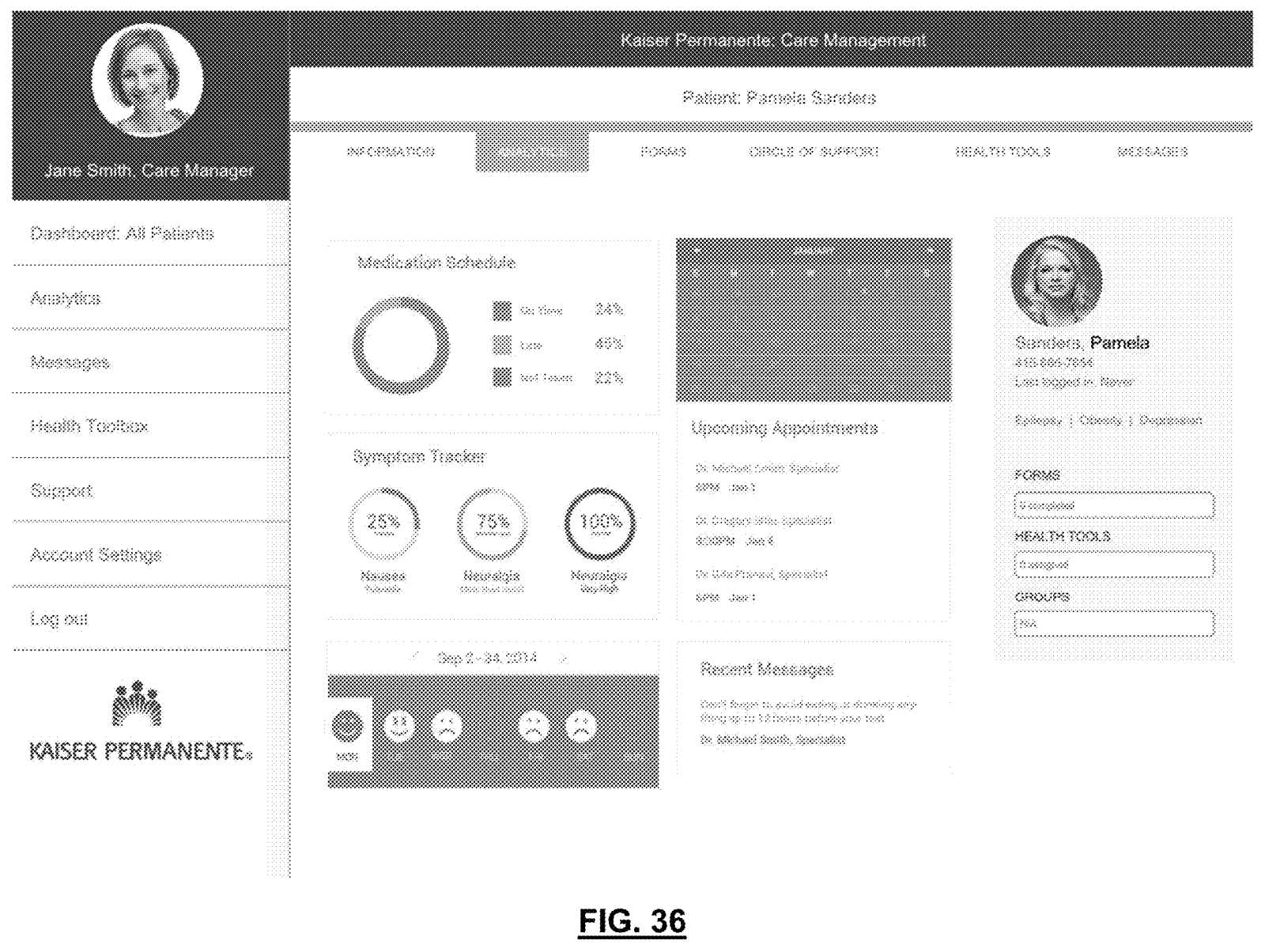

As shown in FIG. 36, a case manager may also access personalized reports generated for a particular patient 18. This report may include various patient data collected from the patient (e.g., by way of the widgets depicted in FIG. 27). Case managers may also assign particular widgets or Health Quests 26 to particular patients, or exchange messages with particular patients by way of partners portal module 340.

Survey module 370 is configured to present surveys to patients 18 to collect patient data. The surveys include a survey automatically generated by analytics module 350. Survey module 370 may engage a patient 18 in one or more studies or surveys at a time (a study may comprise one or more surveys). In an embodiment, patient can be given set time period (e.g. 1-3 days) to complete each survey. Survey module 370 may match surveys to patients based on one or more characteristics of the patient or based on generated insights.

Platform 14 includes an analytics module 350 to generate insights into patient behavior. Analytics may be applied to patient data collected for a particular patient 18. Analytics may also be applied to patient data collected and aggregated for a population of patients 18.

In an embodiment, analytics module 350 may be configured to examine real-time or near real-time data relating to patient's completion process of various Health Quests 26, and optionally communication data between the patient and a Circle of Support member, or between two or more Circle of Support members. For example, analytics module 350 may, through one or more data mining or machine learning techniques, can learn that a patient 18 is concerned with his or her weight, and may in turn recommend a nutrition diet based on a number of factors such as the patient's current weight and goal weight, the patient's typical meal plan, his or her health conditions.

In an embodiment, analytics module 350 may be configured to access one or more databases containing both historical and real-time data regarding other patients and their profiles. Analytics module 350 may be further configured to take the data regarding other patients and to apply data mining or machine learning techniques, in order to determine a best practice solution for a patient 18 based on the historical and/or real-time data related to other patients with similar conditions, weights, health objectives, and/or any other suitable factor. Such a determination of a best practice solution can be further based on scientifically validated principles, available from a data repository or determined by the same analytics utility based on one or more patients' records.

Furthermore, data collected through application 100 (or one or more widgets) can be time stamped, so that all the data, suggestions, best practice solution or recommendations may be analyzed and processed to generate a patient journey for patient 18.

In an embodiment, analytics module 350 may be configured to normalize the intelligent suggestions or recommendations in order to address variance of different patient journeys. For example during a recovery path for a specific disease, each patient may progress through a certain number of stages, but for different patients the period of time for each stage may vary. Many other types of variations are possible. Application 100 and/or platform 14 can determine, via data mining and/or machine learning techniques, for example the patient's current stage, and thereby can determine the appropriate information or suggestions (on an automated basis) on an appropriate timing that is more likely to promote the health objectives.

In an embodiment, analytics module 350 may apply learning algorithms to collected data to model adherence and patient outcomes. The models can be, in turn, used to understand new patient data being collected, triggering intervention when undesirable trends are detected and triggering rewards for positive trends. The patient rewards system automatically adapts by modifying point values awarded for various actions in real time or near real time, in order to provide the appropriate level of incentive.

For example, analytics module 350 may be configured to track, visualize and analyze (e.g., using statistical models) factors contributing to:
 i. Patient adherence
 ii. Healthy eating
 iii. Exercise behaviors
 iv. Knowledge retention
 v. Quality of communication
 vi. Symptom control Analytics module 350 may generate various insights relating to patient health such as, for example:
 i. Disease category understanding
 ii. Competitive insights
 iii. Patient profiles and segment sizing
 iv. Standard of care/messaging validation
 v. Behaviour tracking
 vi. Patient support needs
 vii. Outcomes monitoring
 viii. Medication adherence and compliance information
 ix. Common questions that patients ask health care professionals Analytics module 350 may be configured to generate documents including patient data for use by users, including patients, Circle of Support members, healthcare professionals, researchers, clients, etc.

For example, analytics module 350 may generate reports for patients, showing a snapshot of on-going and completed quests (e.g. "patient journey"). Trend lines and algorithmic assessments can help patients understand their place in a patient journey. Reports can include for example a history of rewards and recognitions (e.g. number of plaques collected), and a journal summary (trend line of emotions based on feedback). Such reports can motivate patients and Circle of Support members (specifically healthcare providers) to pursue self-care management for patient 18.

In an embodiment, analytics module 350 may be configured to generate at least part of a Subjective Objective Assessment Plan (SOAP) note for a physician (or another healthcare provider). For example, analytics module 350 may identify relevant SOAP templates based on generated patient insights, and then populate those templates according to collected data. The generated SOAP note (or portion thereof) may be provided to a physician (e.g., by way of partners portal module 340) for review and modification. In this way, manual data collection and entry steps associated with preparation of SOAP notes may be avoided, and SOAP notes may be prepared more efficiency. Further, human error associated with manual data collection and entry may be avoided.

In an embodiment, analytics module 350 may be configured to generate a personalized agenda for a patient for use in an upcoming appointment with the patient's physician (or another healthcare provider). The agenda may include patient data as collected by platform 14. For example, the agenda may include data regarding the patient's adherence to a drug regimen, data relating to tracked health metrics such as blood pressure or symptoms. In an embodiment, analytics module 350 may generate the agenda to include a visualization showing progress of a metric or symptom over time. For example, the visualization may show blood pressure tracked over a pre-defined period (e.g., one month) with trend lines. In an embodiment, analytics module 350 may generate the agenda to include data relevant to a pre-defined purpose or scope of the appointment. In an embodiment, analytics module 350 may generate the agenda to include data relevant to the particular expertise of the healthcare provider (e.g., in the case where the provider is a specialist physician). For example, the agenda may be generated to include patient data relating to heart health if the appointment is with a cardiologist.

In an embodiment, analytics module 350 may generate the agenda using medical terms (jargon) or other technical language intended for consumption by the healthcare professional. In this case, the agenda may be annotated or otherwise supplemented with plain-language translations that may be more readily understood by a patient. To this end, analytics module 350 may include a combination of dictionaries and look-up tables establishing mappings between technical language and plain language. Such dictionaries and look-up tables may be used to generate an agenda containing technical language and plain-language translated supplements.

Conveniently, generation of a personalized agenda in manners described above may empower patients by facilitating preparation for an appointment with a physician or other healthcare provider. Clarity of communication between patients and healthcare providers may be improved, which may have a beneficial impact on health outcomes for patients.

In an embodiment, the above noted dictionaries and look-up tables may be used in other aspects of components of platform 14. For example, these dictionaries and tables may be used to translate between technical language and plain language in communications between a patient and a Circle of Support member (e.g., a healthcare provider). In an embodiment, analytics module 350 may include a natural language interpreter configured to translate plain-language communication from a patient into technical language In one example, translation may be provided in messages between a patient and a healthcare provider transmitted through platform 14. In an embodiment, such translation may be performed in a manner transparent to both sender and recipient. In another example, translation may be applied to instructions in technical language from a healthcare provider.

In an embodiment, platform 14 may facilitate communication by patients using appropriate jargon or technical language in other ways. For example, platform 14 may implement an automated decision tree for selection of the appropriate language, e.g., by answering a sequence of questions regarding the patient's symptoms, desired treatment, desired outcome, or the like.

In an embodiment, platform 14 may include a speech-to-text engine to convert an audio communication from a patient or other user (e.g., a healthcare provider) for further processing to provide the above-noted translation.

In an embodiment, platform 14 may facilitate access to additional information relevant to the communication. For example, platform 14 may maintain identifiers of a plurality of journal articles (e.g., relating to a particular prescription drug) and may automatically insert links to such articles in communications engaged in by the patient. For example, when the patient receives a communication from a healthcare provider relating to a particular prescription drug, platform 14 may modify the communication to include a link to one or more articles regarding that prescription drug.

In an embodiment, analytics module 350 may perform analytics to generate one or more of the following insights:
  i. Real-time understanding of daily patient health behavior and decision making
  ii. Isolation of key influencers of patient behaviour
  iii. Extraction of interrelationships between influencers
  iv. An understanding of patients' decision making before and after point of transaction, which is not captured by current data analytics in the market
  v. A combination of quantitative and qualitative analytics that present both breadth and depth of data, customizable at the marketer's fingertips
  vi. Prediction of patient behaviors that remediate the biases caused by existing retrospective research and perceptual mapping.

Analytics module 350 can be further configured to:
  i. Use patient psychological dispositions generated from proprietary instrument to evaluate unique patient types to predict their day to day health behavior and decision-making;
  ii. Monitor and map out micro-level day-to-day changing trends amongst individuals as well as different patient clusters; and/or
  iii. Synthesize macro-level decision making conflicts for individuals as well as different patient clusters.

In an embodiment, analytics module 350 may analyze patient data collected for a population of patients 18 to identify groups of patients 18 with similar characteristics, similar health profiles (e.g., similar drugs being taken, similar health conditions, similar symptoms, etc.), or similar behavioural habits. Analytics module 350 may apply various clustering or grouping techniques to arrange patients 18 into such groups. Groups may overlap such that each patient 18 is classified into multiple groups. Different groups may be formed for different analytical purposes (e.g., patient quality of life analysis, medication adherence analysis, market access analysis, etc.). Once such groups have been created, analytics module 350 may generate insights into future behaviours or future responses to interventions based on data collected for the group. For example, analytics module 350 may predict behaviour for a particular patient or predict a response to intervention for a particular patient based on behaviours/responses logged for other patients in the same group.

Figure 37:
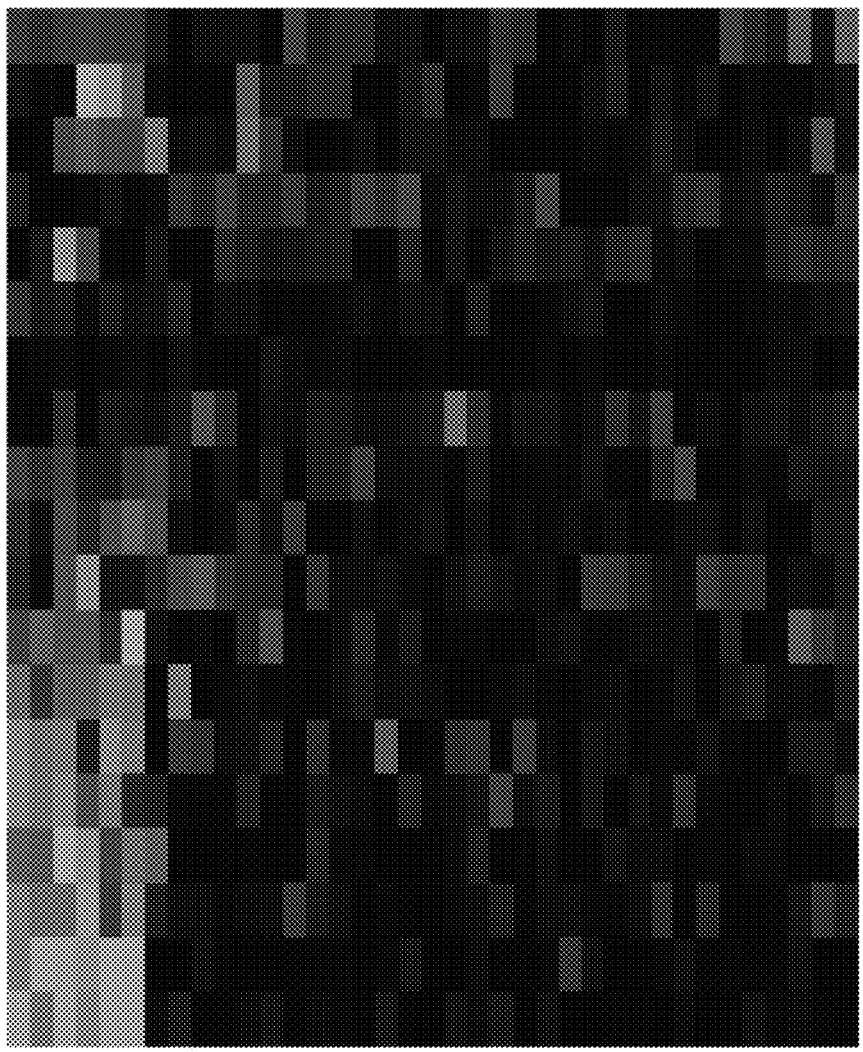
FIG. 37 is an example heat-map corresponding to behaviour signatures for patients, in accordance with an embodiment.

In an embodiment, analytics module 350 may generate an electronic signature (or fingerprint) based on data collected for a particular patient 18. The signature is unique to the particular patient 18 and encodes data collected for that patient 18 (e.g., behavioural data collected over time). FIG. 37 illustrates such fingerprints, in accordance with an embodiment. As shown, the fingerprint data is arranged into an array of heatmap cells similar to a DNA microarray. Each column may correspond to one type of patient behaviour/task, e.g., take morning pills, take noon pills, take afternoon pills, take Monday pills, take Tuesday pills, nutrition data being entered, wearable device data being logged, etc. Each row may correspond to a patient. The colour or intensity of each cell may correspond to a degree of completion or compliance for a particular behaviour/task for a particular patient 18. Once this fingerprint data has been generated, techniques applicable to DNA microarray analysis (e.g., probabilistic matrix factorization) may be applied to segment patients into clusters 18, and thereby define groups of patients 18.

In an embodiment, analytics module 350 may discover for example recovery trends based on aggregated patient data, and provide these trends on an automated basis to subscribers (e.g. patients, clients, health care professionals or partners) through one or more of the portals described herein.

Platform 14 may also include a data storage, collation and processing unit that can store, pre-process, prepare and process collected data. Platform 14 may further comprise a data administration unit. The data storage, collation and processing unit can be configured to persistently store the collected data.

The data storage, collation and processing unit may also conduct pre-processing of the collected data to aid the performance of report generation and execution. For example, where performance-intensive analytics are known to be run, the data storage, collation and processing unit could anticipate these runs, pre-fetch and pre-process the collected data to reduce the number of calculations necessary at execution.

The data storage, collation and processing unit, may in some embodiments be a data warehouse, a flat database or a relational database.

Examples of processing that may be done by the data storage, collation and processing unit include one or more of the following:

i. Receiving reference data from standards organizations or manual input (e.g. the maximum pressure may be set out or provided as an industry standard or a formulary guideline)

ii. Conducting queries of the collected data to run reports. These queries may be executed using methods known to a skilled user, such as SQL query language, SAS language, etc.

iii. Providing computational and analytics support for machine learning, application of heuristics-based approaches for independent variable identification in development of, for example, neural networks.

iv. Pre-processing collected data to pre-fetch data to improve execution performance.

v. Collating collected data from various sources and grouping the data.

vi. Providing tagging of data with metadata (e.g. date received, occurrence during an incident, related manufacturing stage, operator present, plant information, manufactured using instruction template 5 revision 6, manufacturing parameters exceeded).

vii. Adding unique identifiers to collected data to improve data integrity and performance for data record retrieval (e.g. the addition of primary and foreign keys).

viii. Adding associations between data points either automatically based upon a set of rules, or manually.

ix. Sort collected data according to date, identifiers, metatags.

Figure 22:
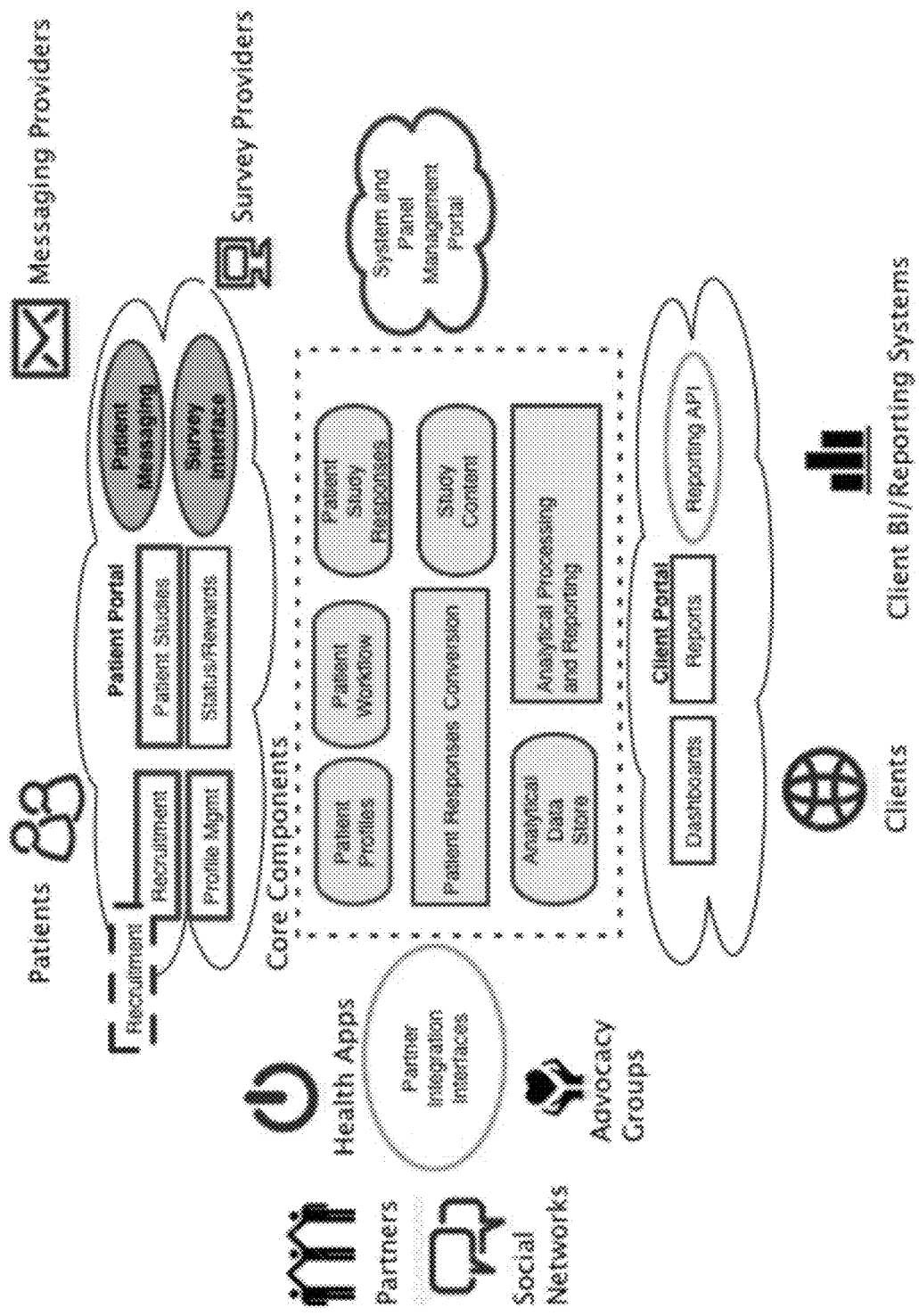
FIG. 22 illustrates another exemplary configuration of the system of FIG. 3, in accordance with an embodiment.

A possible configuration of platform 14 in accordance with another embodiment of the invention is shown in FIG. 22.

The operation of platform 14 to generate insights, and to influence patient behaviour may be further described with reference to particular examples provided below.

In one example, platform 14 may be used to promote patient adherence (e.g., to drug regimens). Patient adherence is as low as 50% across disease states, and non-adherence has been implicated in over 20% of re-hospitalizations, costing healthcare organizations billions in un-reimbursed dollars. Thus, improving patient adherence may improve patient health and reduce healthcare costs.

In this example, patient data may be collected using the medication tracker widget (FIG. 28). The collected data may be analyzed to determine one or more of: patients' medication usage habits (such as time of day), dose and frequency adherence, reasons for non-adherence, medication switch/add-on dynamics, barriers and drivers of medication adoption, purchase behaviour (by brand), etc. Data may also be collected using the symptom tracker widget, and symptom data and medication data may be correlated to generate insights regarding adverse events, drug efficacy, etc.

Platform 14 may improve adherence by providing reminders to track medication, reminders to refill prescription, countdown timers, etc. Platform 14 may also automatically notify one or more Circle of Support members upon determining that a patient is not taking medication. For example, platform 14 may automatically generate a message to be sent by a Circle of Support member, to remind or encourage a patient 18 to take certain medication.

Platform 14 may also automatically provide medical information to patients 18 and Circle of Support members to improve adherence by improving medical knowledge overall, e.g., regarding particular medications, side effects information, what to do, etc, disease-specific information to increase health literacy, patient illness perception, and self-efficacy. For example, platform 14 may provide this information in the form of automatically generated messages sent to patients 18 and Circle of Support members, e.g., by way of application 100.

The collected data may also be used to measure and drive improved patient adherence for a specific brand, to understand other components of the patient experience that impacts adherence, so that support programs can be developed accordingly to drive behaviour change.

The collected data may also be used to more generally monitor patients' drug use. For example, the collected data may be used to measure and track patients' treatment decision-making dynamics around adoption, switch, and drop-off, add-on, off-label, alternative therapies, barriers and drivers.

In another example, platform 14 may be used to monitor patient outcomes. Outcomes analysis seeks to understand the end results of particular health care practices and interventions. End results include effects that people experience and care about, such as change in the ability to function. In particular, for individuals with chronic conditions—where cure is not always possible—end results include quality of life as well as mortality. By linking the care people receive to the outcomes they experience, outcomes analysis has become a key component of developing better ways to monitor and improve the quality of care.

In this example, patient data may be collected by way of the medication tracker widget, the symptoms widget (e.g., to track side effects), the journal widget (e.g., to track quality of life), and other widgets configured to track/monitor other components of health such as mood, vitals, etc.

Examples of outcomes that may be determined by analyzing the patient data include mortality, physiologic measures (e.g. blood pressure), clinical events (e.g. stroke), symptoms (e.g. breathing difficulty), functional measures (e.g. health survey), patients' experiences with care (e.g. feedback on health care provider experience).

Such outcomes may be used to measure and drive improved patient outcomes, to provide data for clinical trials, and/or to understand other components of the patient experience that impacts patient outcomes, so that support programs can be developed accordingly.

In yet another example, platform 14 may be used to measure and/or promote market access. Market access is the process to ensure that all appropriate patients who would benefit from a drug get rapid and maintained access to the drug.

In this example, data may be collected by way of the journal widget (FIG. 32). This data may be analyzed to determine patients' quality of life, behaviours, decision conflicts, and experiences, and overall health, illness impact on quality of life, which may include the following aspects: active living, social functioning, types of health-promoting behaviours, coping style, and to evaluate the patient's psychological dispositions. Data may also be collected by way of the mood tracker widget (FIG. 30), and this data may be analyzed to determine a patient's daily ups and downs, psychosocial aspect of illness, impact of illness on emotions, impact of emotions on medication usage, quality of life, etc., sources of stressors and burden, and so on. Collectively, these insights may be used to measure the value of a new therapy against older/existing treatments and its impact on patient values (e.g. quality of life, psychosocial impact, etc.). Such insights may be used as evidence on the benefits of drug in review for market access submission purposes.

In a further example, platform 14 may be used to measure and/or promote a patient's quality of life. In particular, utilization of the journal widget and the other widgets described herein allow allows patients to chronicle their day-to-day experiences with their condition, including with directed questions that are designed to extract specific information. For example, data collected by way of the journalizing widget may be used to determine patients' quality of life, behaviours, decision conflicts, and experiences, and overall health, illness impact on quality of life, which may include the following aspects: active living, social functioning, types of health-promoting behaviours, coping style, and to evaluate a patient's psychological dispositions. Data collected by way of the mood tracker may be used to determine a patient's daily ups and downs, psychosocial aspect of illness, impact of illness on emotions, impact of emotions on medication usage, quality of life, etc., sources of stressors and burden, and so on. Collectively, these insights may be used to generate insight into patient's overall quality of life.

FIGS. 23*a*-23*f* illustrate sample patient reports generated by analytics module 350 and may be displayed to patients 18 (or Circle of Support members) via a patient portal or to clients 24 via a client portal.

FIGS. 24*a*-24*d* demonstrate sample Aggregated Reports generated by analytics module 350 and may be displayed to clients 24 via a client portal.

Patient data may be pre-processed to remove necessary or appropriate confidential information prior to being processed into any report.

The reports may be available to various subscribers (e.g. patients, clients, health care professionals or partners) of platform 14.

In an embodiment, platform 14 may include a suitable combination of mechanisms for protecting the privacy and/or security of collected data and generated insights. For example, platform 14 may store data/insights in storage medium in encrypted form, and/or use encrypted transmissions for communicating data/insights. In an embodiment, the mechanisms may be tailored to meet privacy and/or security requirements in a particular health setting, or to meet privacy and/or security requirements set out by particular government regulations. For example, a specific form or degree of encryption (e.g., 128 bit) may be used to meet these requirements.

The functionality described herein may also be accessed as an Internet service, for example by accessing the functions or features described from any manner of computer device, by the computer device accessing a server computer, a server farm or cloud service configured to implement said functions or features.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. A processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including an EGM, A Web TV, a Personal Digital Assistant (PDA), a smart phone, a tablet or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards and pointing devices, such as mice, touch pads, and digitizing tablets. As another example, a computer may receive input information through speech recognition or in other audible formats.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

The system and method may be embodied as a tangible, non-transitory computer readable storage medium (or multiple computer readable storage media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer-readable storage media) encoded with one or more programs that, when executed on one or more computers or other processors, perform methods that implement the various embodiments discussed above. The computer readable medium or media can be transportable, such that the program or programs stored thereon can be loaded onto one or more different computers or other processors to implement various aspects as discussed above. As used herein, the term "non-transitory computer-readable storage medium" encompasses only a computer-readable medium that can be considered to be a manufacture (i.e., article of manufacture) or a machine.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods as described herein need not reside on a single computer or processor, but may be distributed in a modular fashion amongst a number of different computers or processors to implement various aspects.

Computer-executable instructions may be in many forms, such as program modules, executed by one or more computers or other devices. Generally, program modules include routines, programs, objects, components, data structures, etc, that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Depending on the particular implementation and various associated factors such as the resources of the communications device, wireless network parameters, and other factors, different implementation architectures may be used for the present invention.

It should also be understood that the computer server may be implemented as one or more servers in any possible server architecture or configuration including for example in a distributed server architecture, a server farm, or a cloud based computing environment.

Wherever the system is described as receiving input from the user of the communications device, it is to be understood that the input may be received through activation of a physical key on the communications device, through interaction with a touch screen display of the communications device, through a voice command received at the communications device and processed by the system, through a user gesture observed and processed at the communications device, through physically moving the communications device in a predetermined gesture pattern including shaking the communications device, through receiving data from another local or remote communications device associated with the user, or through any other sensory interaction with the communications device or otherwise controlling the communications device.

The present system and method may be practiced in various embodiments. A suitably configured computer device, and associated communications networks, devices, software and firmware may provide a platform for enabling one or more embodiments as described above.

Figure 38:
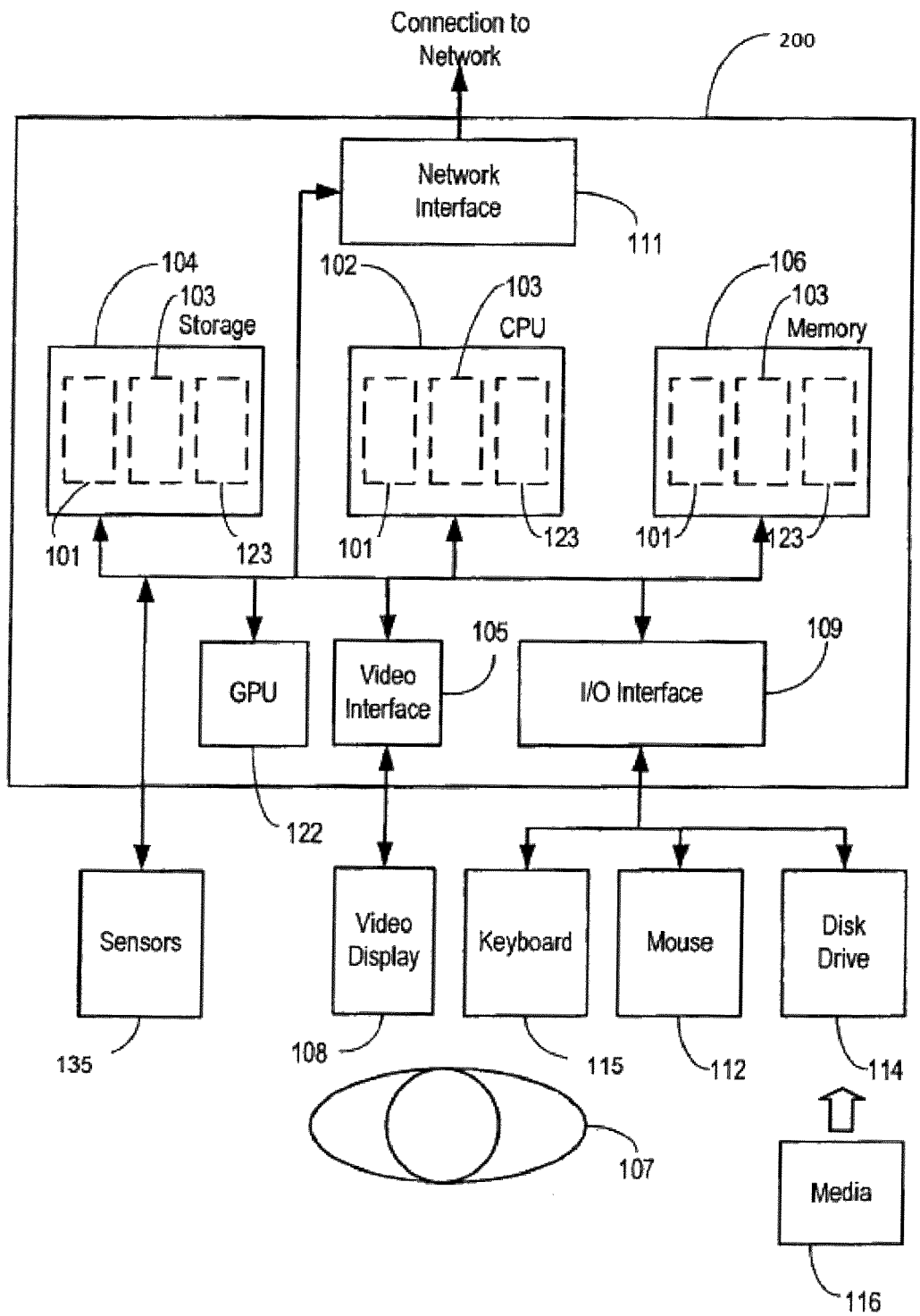
FIG. 38 is a block diagram of a computer system that may be adapted to function as the system of FIG. 3, in accordance with an embodiment.

By way of example, FIG. 38 shows an example computer device 200 that may include a central processing unit ("CPU") 102 connected to a storage unit 104 and to a random access memory 106. The CPU 102 may process an operating system 101, application program 103, and data 123. The operating system 101, application program 103, and data 123 may be stored in storage unit 104 and loaded into memory 106, as may be required. Computer device 200 may further include a graphics processing unit (GPU) 122 which is operatively connected to CPU 102 and to memory 106 to offload intensive image processing calculations from CPU 102 and run these calculations in parallel with CPU 102. An operator 107 may interact with the computer device 100 using a video display 108 connected by a video interface 105, and various input/output devices such as a keyboard 115, mouse 112, and disk drive or solid state drive 114 connected by an I/O interface 109. In known manner, the mouse 112 may be configured to control movement of a cursor in the video display 108, and to operate various graphical user interface (GUI) controls appearing in the video display 108 with a mouse button. The disk drive or solid state drive 114 may be configured to accept computer readable media 116. The computer device 200 may form part of a network via a network interface 111, allowing the computer device 200 to communicate with other suitably configured data processing systems (not shown). One or more different types of sensors 135 may be used to receive input from various sources.

The present system and method may be practiced on virtually any manner of computer device including a desktop computer, laptop computer, tablet computer or wireless handheld. The present system and method may also be implemented as a computer-readable/useable medium that includes computer program code to enable one or more computer devices to implement each of the various process steps in a method in accordance with the present invention. In case of more than computer devices performing the entire operation, the computer devices are networked to distribute the various steps of the operation. It is understood that the terms computer-readable medium or computer useable medium comprises one or more of any type of physical embodiment of the program code. In particular, the computer-readable/useable medium can comprise program code embodied on one or more portable storage articles of manufacture (e.g. an optical disc, a magnetic disk, a tape, etc.), on one or more data storage portioned of a computing device, such as memory associated with a computer and/or a storage system.

The mobile application of the present invention may be implemented as a web service, where the mobile device includes a link for accessing the web service, rather than a native application.

The functionality described may be implemented to any mobile platform, including the iOS™ platform, ANDROID™, WINDOWS™ or BLACKBERRY™.

The embodiments described herein involve computing devices, servers, receivers, transmitters, processors, memory, display, networks particularly configured to implement various acts. The embodiments described herein are directed to electronic machines adapted for processing and transforming electromagnetic signals which represent various types of information. The embodiments described herein pervasively and integrally relate to machines, and their uses; and the embodiments described herein have no meaning or practical applicability outside their use with computer hardware, machines, a various hardware components.

Substituting the computing devices, servers, receivers, transmitters, processors, memory, display, networks particularly configured to implement various acts for non-physical hardware, using mental steps for example, may substantially affect the way the embodiments work.

Such computer hardware limitations are clearly essential elements of the embodiments described herein, and they cannot be omitted or substituted for mental means without having a material effect on the operation and structure of the embodiments described herein. The computer hardware is essential to the embodiments described herein and is not merely used to perform steps expeditiously and in an efficient manner.

While illustrated in the block diagrams as groups of discrete components communicating with each other via distinct electrical data signal connections, the present embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching example embodiments.

It will be appreciated by those skilled in the art that other variations of the embodiments described herein may also be practiced without departing from the scope of the invention. Other modifications are therefore possible.

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances, without departing from the scope of the invention, which is to be limited only by the claims.

What is claimed is:

1. A computer-implemented method for generating insights relating to patient health using a social networking platform interconnecting a patient with a plurality of care givers, the method comprising:
   receiving at least one characteristic of the patient, the at least one characteristic comprising a health condition of the patient;
   providing, on a user interface at a first computing device, options to one or more of the plurality of care givers to customize at least one customized computer application for use by the patient to solicit and collect patient data from the patient, wherein a visual appearance of the at least one customized computer application is customized to the patient;
   providing the at least one customized computer application to a portal accessible by the patient;
   displaying, on a user interface at a second computing device, the at least one customized computer application by way of the social networking platform and the portal;
   receiving, at the at least one customized computer application, first patient data reflective of the health condition of the patient;
   transmitting, by way of at the social networking platform, a communication from at least one of the care givers to the patient, wherein the transmitting comprising translating, by at least one of a dictionary and/or a look-up table, technical language in the communication to plain language, wherein the technical language includes at least one medical term;
   receiving, by way of the social networking platform, second patient data reflective of the health condition of the patient, the second patient data responsive to the transmitted communication;
   analyzing, using at least one processor, the first and second patient data to determine at least one insight relating to health of the patient, wherein the at least one insight comprises an insight reflecting the patient's adherence to a medication regimen; and
   generating, using the at least one processor, a report for presenting the at least one insight.

2. The method of claim 1, further comprising: processing, at the at least one processor, the first patient data to generate a recommendation for a communication from the at least one care giver to the patient.

3. The method of claim 1, further comprising: matching, at the at least one processor, at least one further care giver to the patient based on at least the health condition of the patient.

4. The method of claim 1, wherein the transmitting comprises applying speech-to-text conversion to the communication.

5. The method of claim 1, further comprising: offering an incentive to the patient for entering the first patient data.

6. The method of claim 1, wherein one or both of the first patient data and the second patient data comprises a report that the patient has taken a particular medication.

7. The method of claim 1, wherein one or both of the first patient data and the second patient data comprises a report of a particular mood of the patient.

8. The method of claim 1, wherein one or both of the first patient data and the second patient data comprises a health metric of the patient.

9. The method of claim 8, wherein the health metric comprises a measurement of the patient's weight or the patient's blood pressure.

10. The method of claim 1, wherein the at least one insight comprises an insight reflecting the patient's quality of life.

11. The method of claim 1, wherein the at least one insight comprises an insight reflecting clinical efficacy of a medication taken by the patient.

12. The method of claim 1, wherein the at least one characteristic further comprises at least one of an age, a gender, and a geographic location of the patient.

13. The method of claim 1, wherein the report comprises a Subjective Objective Assessment Plan note.

14. The method of claim 1, wherein the report comprises an agenda for an appointment between the patient and a health care provider.

15. The method of claim 1, wherein the plurality of care givers comprises at least one of a health care professional and a family member of the patient.

16. The method of claim 1, further comprising receiving third patient data generated by an electronic device.

17. The method of claim 16, wherein the electronic device is a radio-frequency identification tag.

18. The method of claim 1, wherein the generating comprises classifying the patient into at least one group of patients.

19. The method of claim 18, wherein the classifying comprises generating a behavioural fingerprint for the patient.

20. A system for generating insights relating to patient health, the system comprising:
- a social networking platform interconnecting a patient with a plurality of care givers;
- a first computing device;
- a second computing device; and
- at least one processor configured to:
  - receive at least one characteristic of the patient, the at least one characteristic comprising a health condition of the patient;
  - provide, on a user interface at the first computing device, options to one or more of the plurality of care givers to customize at least one customized computer application for use by the patient to solicit and collect patient data from the patient, wherein a visual appearance of the at least one customized computer application is customized to the patient;
  - provide the at least one customized computer application to a portal accessible by the patient;
  - display, on a user interface at the second computing device, the at least one customized computer application by way of the social networking platform and the portal;
  - receive, at the at least one customized computer application, first patient data reflective of the health condition of the patient;
  - transmit, by way of at the social networking platform, a communication from at least one of the care givers to the patient, wherein the transmitting comprises translating, by at least one of a dictionary and/or a look-up table, technical language in the communication to plain language, wherein the technical language includes at least one medical term;
  - receive, by way of the social networking platform, second patient data reflective of the health condition of the patient, the second patient data responsive to the transmitted communication;
  - analyze the first and second patient data to determine at least one insight relating to health of the patient, wherein the at least one insight comprises an insight reflecting the patient's adherence to a medication regimen; and
  - generate a report for presenting the at least one insight.

21. The system of claim 20, wherein the at least customized of computer application comprises a computer application configured as a game.

* * * * *